US012391756B2

(12) United States Patent
Liu et al.

(10) Patent No.: US 12,391,756 B2
(45) Date of Patent: Aug. 19, 2025

(54) BINDING MOLECULE SPECIFIC FOR CD39 AND USE THEREOF

(71) Applicant: JACOBIO PHARMACEUTICALS CO., LTD., Beijing (CN)

(72) Inventors: Qinghao Liu, Beijing (CN); Wenlai Zhou, Beijing (CN); Haiyan Yang, Beijing (CN); Hongling Wang, Beijing (CN); Yajing Wang, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 751 days.

(21) Appl. No.: 17/774,170

(22) PCT Filed: Nov. 4, 2020

(86) PCT No.: PCT/CN2020/126351
§ 371 (c)(1),
(2) Date: May 4, 2022

(87) PCT Pub. No.: WO2021/088838
PCT Pub. Date: May 14, 2021

(65) Prior Publication Data
US 2022/0411498 A1 Dec. 29, 2022

(30) Foreign Application Priority Data

Nov. 5, 2019 (WO) ................ PCT/CN2019/115505

(51) Int. Cl.
*C07K 16/28* (2006.01)
*A61P 35/00* (2006.01)

(52) U.S. Cl.
CPC .......... *C07K 16/2803* (2013.01); *A61P 35/00* (2018.01); *C07K 2317/24* (2013.01); *C07K 2317/52* (2013.01); *C07K 2317/56* (2013.01); *C07K 2317/622* (2013.01)

(58) Field of Classification Search
CPC ..................... C07K 16/2803; C07K 2317/622
See application file for complete search history.

(56) References Cited

U.S. PATENT DOCUMENTS

2019/0284295 A1\* 9/2019 Chappel ............... G01N 33/573

FOREIGN PATENT DOCUMENTS

| CN | 110382544 | 10/2019 |
|---|---|---|
| WO | 2016073845 | 5/2016 |
| WO | 2017089334 | 6/2017 |
| WO | 2017157948 | 9/2017 |
| WO | 2018065552 | 4/2018 |
| WO | 2019027935 | 2/2019 |
| WO | 2019068907 | 4/2019 |
| WO | 2019096900 | 5/2019 |
| WO | 2019178269 | 9/2019 |

\* cited by examiner

*Primary Examiner* — Janet L Epps-Smith
*Assistant Examiner* — Nada Ahmed Mahmou Elmansy
(74) *Attorney, Agent, or Firm* — Baratta Law PLLC; Lawrence A. Baratta, Jr.

(57) ABSTRACT

Provided is a binding molecule specifically for CD39 and the use thereof. Specifically, provided is an antibody that binds to CD39 and inhibits the activity of CD39 or an antigen binding part thereof, the use of the antibody or the antigen binding part thereof in the treatment of diseases, a nucleic acid molecule encoding the antibody or the antigen binding part thereof, an expression vector for expressing the antibody or the antigen binding part thereof, a host cell, and a preparation method.

20 Claims, 9 Drawing Sheets
Specification includes a Sequence Listing.

293T/17-HuCD39

SEQUENCE LISTING

<160> NUMBER OF SEQ ID NOS: 79

<210> SEQ ID NO 1
<211> LENGTH: 452
<212> TYPE: PRT
<213> ORGANISM: Homo sapiens

<400> SEQUENCE: 1

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365
```

```
Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
                420                 425                 430

Thr Pro Leu Ser His Ser Thr Tyr Val Ala His His His His His His
            435                 440                 445

His His His His
    450

<210> SEQ ID NO 2
<211> LENGTH: 532
<212> TYPE: PRT
<213> ORGANISM: Macaca fascicularis

<400> SEQUENCE: 2

Met Leu Phe Asp Ser Ile Leu Ser Thr Val Gly Leu Ser Lys Leu Val
1               5                   10                  15

Ser Val Val Ser Ser Pro Ala Ala Ala Leu Ser Lys Ser Asn Val Lys
                20                  25                  30

Thr Phe Cys Ser Lys Asn Ile Leu Ala Ile Leu Gly Phe Ser Ser Ile
            35                  40                  45

Ile Ala Val Ile Ala Leu Leu Ala Val Gly Leu Thr Gln Asn Lys Ala
        50                  55                  60

Leu Pro Glu Asn Ile Lys Tyr Gly Ile Val Leu Asp Ala Gly Ser Ser
65                  70                  75                  80

His Thr Ser Leu Tyr Ile Tyr Lys Trp Pro Ala Glu Lys Glu Asn Asp
                85                  90                  95

Thr Gly Val Val His Gln Val Glu Glu Cys Arg Val Lys Gly Pro Gly
            100                 105                 110

Ile Ser Lys Tyr Val Gln Lys Val Asn Glu Ile Gly Ile Tyr Leu Thr
        115                 120                 125

Asp Cys Met Glu Arg Ala Arg Glu Val Ile Pro Arg Ser Gln His Gln
    130                 135                 140

Glu Thr Pro Val Tyr Leu Gly Ala Thr Ala Gly Met Arg Leu Leu Arg
145                 150                 155                 160

Met Glu Ser Glu Glu Leu Ala Asp Arg Val Leu Asp Val Val Glu Arg
                165                 170                 175

Ser Leu Ser Asn Tyr Pro Phe Asp Phe Gln Gly Ala Arg Ile Ile Thr
            180                 185                 190

Gly Gln Glu Glu Gly Ala Tyr Gly Trp Ile Thr Ile Asn Tyr Leu Leu
        195                 200                 205

Gly Lys Phe Ser Gln Lys Thr Arg Trp Phe Ser Ile Val Pro Tyr Glu
    210                 215                 220

Thr Asn Asn Gln Glu Thr Phe Gly Ala Leu Asp Leu Gly Gly Ala Ser
225                 230                 235                 240

Thr Gln Ile Thr Phe Val Pro Gln Asn Gln Thr Thr Glu Ser Pro Asp
                245                 250                 255

Asn Ala Leu Gln Phe Arg Leu Tyr Gly Lys Asp Tyr Asn Val Tyr Thr
            260                 265                 270

His Ser Phe Leu Cys Tyr Gly Lys Asp Gln Ala Leu Trp Gln Lys Leu
        275                 280                 285
```

```
Ala Lys Asp Ile Gln Val Ala Ser Asn Glu Ile Leu Arg Asp Pro Cys
    290                 295                 300

Phe His Pro Gly Tyr Lys Val Val Asn Val Ser Asp Leu Tyr Lys
305                 310                 315                 320

Thr Pro Cys Thr Lys Arg Phe Glu Met Thr Leu Pro Phe Gln Gln Phe
                325                 330                 335

Glu Ile Gln Gly Ile Gly Asn Tyr Gln Gln Cys His Gln Ser Val Leu
            340                 345                 350

Glu Leu Phe Asn Thr Ser Tyr Cys Pro Tyr Ser Gln Cys Ala Phe Asn
        355                 360                 365

Gly Ile Phe Leu Pro Pro Leu Gln Gly Asp Phe Gly Ala Phe Ser Ala
    370                 375                 380

Phe Tyr Phe Val Met Asn Phe Leu Asn Leu Thr Ser Glu Lys Val Ser
385                 390                 395                 400

Gln Glu Lys Val Thr Glu Met Met Lys Lys Phe Cys Ser Gln Pro Trp
                405                 410                 415

Glu Glu Ile Lys Thr Ser Tyr Ala Gly Val Lys Glu Lys Tyr Leu Ser
            420                 425                 430

Glu Tyr Cys Phe Ser Gly Thr Tyr Ile Leu Ser Leu Leu Leu Gln Gly
        435                 440                 445

Tyr His Phe Thr Ala Asp Ser Trp Glu His Ile His Phe Ile Gly Lys
    450                 455                 460

Ile Gln Gly Ser Asp Ala Gly Trp Thr Leu Gly Tyr Met Leu Asn Leu
465                 470                 475                 480

Thr Asn Met Ile Pro Ala Glu Gln Pro Leu Ser Thr Pro Leu Ser His
                485                 490                 495

Ser Thr Tyr Val Phe Leu Met Val Leu Phe Ser Leu Val Leu Val Ile
            500                 505                 510

Val Ala Ile Ile Gly Leu Leu Ile Phe His Lys Pro Ser Tyr Phe Trp
    515                 520                 525

Lys Asp Met Val
    530

<210> SEQ ID NO 3
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 3

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Met Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Ala Ser Leu Arg Ser Glu Asp Thr Ala Met Tyr Tyr Cys
                85                  90                  95

Ala Arg Asp Leu Tyr Tyr Asp His Val Leu Asp Tyr Trp Gly Gln Gly
            100                 105                 110
```

```
Thr Thr Leu Thr Val Ser Ser
        115

<210> SEQ ID NO 4
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 4
gaggtgcagc tggtggagtc tgggggaggc ttagtgaagc ctggagggtc cctgaaactc      60
tcctgtgcag cctctggatt cactttcagt gactatggaa tgcactgggt tcgtcaggct     120
ccagagaagg ggctggagtg ggttgcatac attagtagtg gcagtagtat catgtactat     180
gcagacacag tgaagggccg attcaccatc tccagagaca atgccaagaa caccctgttc     240
ctgcaaatgg ccagtctgag gtctgaggac acggccatgt attattgtgc aagggacctc     300
tactatgatc acgtccttga ctactggggc caaggcacca ctctcacagt ctcctca       357

<210> SEQ ID NO 5
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 5

Asp Tyr Gly Met His
1               5

<210> SEQ ID NO 6
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 6

Tyr Ile Ser Ser Gly Ser Ser Ile Met Tyr Tyr Ala Asp Thr Val Lys
1               5                   10                  15

Gly

<210> SEQ ID NO 7
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 7

Asp Leu Tyr Tyr Asp His Val Leu Asp Tyr
1               5                   10

<210> SEQ ID NO 8
<211> LENGTH: 107
<212> TYPE: PRT
<213> ORGANISM: Artificial Sequence
<220> FEATURE:
<223> OTHER INFORMATION: synthetic peptide

<400> SEQUENCE: 8

Asp Ile Gln Met Thr Gln Ser Pro Ser Ser Leu Ser Ala Ser Leu Gly
1               5                   10                  15
```

Glu Arg Val Ser Leu Thr Cys Arg Ala Ser Gln Ile Arg Gly Tyr
            20                  25                  30

Leu Ile Trp Leu Gln Gln Lys Pro Gly Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Thr Ser Tyr Pro Arg
                85                  90                  95

Thr Phe Gly Gly Gly Thr Lys Leu Glu Ile Lys
            100                 105

<210> SEQ ID NO 9
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 9
gacatccaga tgacccagtc tccatcctcc ttatctgcct ctctgggaga aagagtcagt    60
ctcacttgtc gggcaagtca ggaaattcgt ggttacttaa tttggcttca gcagaaacca   120
ggtggaacta ttaaacgcct gatctacgcc gcatccactt tagattctgg tgtcccaaag   180
aggttcagtg gcagtaggtc tgggtcagat tattctctca ccatcagcag ccttgagtct   240
gaagattttg cagactatta ctgtctacaa tatactagtt atcctcggac gttcggtgga   300
ggcaccaagc tggaaatcaa a                                             321

<210> SEQ ID NO 10
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 10

Arg Ala Ser Gln Glu Ile Arg Gly Tyr Leu Ile
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 11

Ala Ala Ser Thr Leu Asp Ser
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 12

Leu Gln Tyr Thr Ser Tyr Pro Arg Thr
1               5

```
<210> SEQ ID NO 13
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 13

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Met Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Ala Ser Leu Arg Ser Glu Asp Thr Ala Met Tyr Tyr Cys
                85                  90                  95

Ala Arg Asp Leu Tyr Tyr Asp His Val Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445
```

<210> SEQ ID NO 14
<211> LENGTH: 1335
<212> TYPE: DNA
<213> ORGANISM: Artificial Sequence
<220> FEATURE:
<223> OTHER INFORMATION: synthetic polynucleotide

<400> SEQUENCE: 14

```
gaggtgcagc tggtggagtc tgggggaggc ttagtgaagc ctggagggtc cctgaaactc      60
tcctgtgcag cctctggatt cactttcagt gactatggaa tgcactgggt tcgtcaggct     120
ccagagaagg ggctggagtg ggttgcatac attagtagtg gcagtagtat catgtactat     180
gcagacacag tgaagggccg attcaccatc tccagagaca tgccaagaa caccctgttc      240
ctgcaaatgg ccagtctgag gtctgaggac acggccatgt attattgtgc aagggaccctc    300
tactatgatc acgtccttga ctactggggc caaggcacca ctctcacagt ctcctcagct     360
agcaccaagg gacccctccgt gtttcctctg gctccttgct ccagatctac ctccgagtct    420
accgccgctc tggttgtct ggtgaaggac tacttccccg agccagtgac cgtgtcttgg      480
aacagcggag ctctgacatc cggagtgcac accttttccag ccgtgctgca gtcttccggc   540
ctgtattctc tgtcctccgt ggtgaccgtg ccttcttcca acttcggcac ccagacctac    600
acttgcaacg tggaccacaa gcccctccaac accaaggtgg acaagaccgt ggagcgcaag   660
tgttgcgtcg agtgccctcc ttgcccagct cctccagtgg ccggaccttc tgtgtttctg    720
ttccccccta gcctaagga cacctgatg atctccccgga ccccagaagt gacttgcgtg    780
gtggtggacg tgtctcacga ggaccccgag gtgcagttca attggtacgt ggacggcgtg    840
gaggtgcaca cgctaagac caagcccagg gaggagcagt tcaactccac cttccgggtg     900
gtgtcagtgc tgacagtggt gcaccaggat tggctgaacg gcaaggagta caagtgcaag    960
gtgtccaaca agggcctgcc agctcctatc gagaagacca tctccaagac caagggccag   1020
cccagagagc ctcaggtgta cactgcct ccttcccggg aggagatgac caagaaccag    1080
gtgtccctga cttgcctcgt gaagggattc taccctcccg acatcgcagt cgagtgggaa    1140
tccaacggcc agcccgagaa caactacaag accaccctc ctatgctgga ctccgacggc    1200
tccttcttcc tgtactccaa gctgaccgtg gacaagtccc gttggcagca gggcaacgtg   1260
ttctcttgca gcgtgatgca cgaggccctg cacaaccact acacccagaa gagcctgtcc    1320
ctgtctcccg gcaag                                                     1335
```

<210> SEQ ID NO 15
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 15

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Arg Gly Tyr
            20                  25                  30

Leu Ile Trp Leu Gln Gln Lys Pro Gly Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Thr Ser Tyr Pro Arg
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 16
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 16
gacatccaga tgacccagtc tccatcctcc ttatctgcct ctctgggaga aagagtcagt      60
ctcacttgtc gggcaagtca ggaaattcgt ggttacttaa tttggcttca gcagaaacca     120
ggtggaacta ttaaacgcct gatctacgcc gcatccactt tagattctgg tgtcccaaag     180
aggttcagtg gcagtaggtc tgggtcagat tattctctca ccatcagcag ccttgagtct     240
gaagattttg cagactatta ctgtctacaa tatactagtt atcctcggac gttcggtgga     300
ggcaccaagc tggaaatcaa agaaccgtg gccgctcctt ccgtgttcat cttccctccc      360
tccgacgagc agctgaagag cggaacagcc tctgtcgtgt gcctcctgaa caacttctac     420
ccccgggagg ccaaggtcca gtggaaggtg gacaacgctc tgcagagcgg caactctcag     480
gagagcgtga cagagcagga ctccaaggac tccacctact ccctgtcttc caccctgacc     540
ctgtctaagg ccgactacga gaagcacaag gtgtacgctt gcgaggtgac acaccaggga     600
ctgtcctctc cagtgaccaa gtccttcaac cgcggcgagt gt                        642

<210> SEQ ID NO 17

<211> LENGTH: 119
<212> TYPE: PRT
<213> ORGANISM: Artificial Sequence
<220> FEATURE:
<223> OTHER INFORMATION: synthetic polypeptide

<400> SEQUENCE: 17

```
Glu Val Gln Leu Val Glu Ser Gly Gly Gly Leu Val Lys Pro Gly Gly
1               5                   10                  15

Ser Leu Lys Leu Pro Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Leu Tyr Tyr Asp His Val Leu Asp Tyr Trp Gly Gln Gly
            100                 105                 110

Thr Thr Leu Thr Val Ala Ser
        115
```

<210> SEQ ID NO 18
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 18

```
gaggtgcagc tggtggagtc tgggggaggc ttagtgaagc ctggagggtc cctgaaactc      60
ccctgtgcag cctctggatt cactttcagt gactatggaa tgcactgggt tcgtcaggct     120
ccagagaagg ggctggagtg ggttgcatac attagtagtg gcagtagtat catctactat     180
gcagacacag tgaagggccg attcaccatc tccagagaca atgccaagaa caccctgttc     240
ctgcaaatga ccagtctgag gtctgaggac acggccatgt attactgtgc aagggacctc     300
tactatgatc acgtccttga ctattggggc caaggcacca ctctcacagt cgcctca       357
```

<210> SEQ ID NO 19
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 19

```
Asp Tyr Gly Met His
1               5
```

<210> SEQ ID NO 20
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 20

```
Tyr Ile Ser Ser Gly Ser Ser Ile Ile Tyr Tyr Ala Asp Thr Val Lys
1               5                   10                  15
```

Gly

<210> SEQ ID NO 21
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 21

Asp Leu Tyr Tyr Asp His Val Leu Asp Tyr
1               5                   10

<210> SEQ ID NO 22
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 22

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ile Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Asn Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 23
<211> LENGTH: 321
<212> TYPE: DNA
<213> ORGANISM: Artificial Sequence
<220> FEATURE:
<223> OTHER INFORMATION: synthetic nucleotide

<400> SEQUENCE: 23
gacatccaga tgacccagtc tccatcctcc ttatctgcct ctctgggaga aagagtcagt    60
ctcacttgtc gggcaagtca ggaaattagt ggttacttaa tctggcttca gcagaaacca   120
gatggaacta ttaaacgcct gatctacgcc gcatccactt tagattctgg tgtcccaaaa   180
aggttcagtg gcaataggtc tgggtcagat tattctctca ccatcagcag ccttgagtct   240
gaagattttg cagactatta ctgtctacaa tatgctagtt atcctcggac gttcggtgga   300
ggcaccaagc tggaaatcaa a                                              321

<210> SEQ ID NO 24
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 24

```
Arg Ala Ser Gln Glu Ile Ser Gly Tyr Leu Ile
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 25

```
Ala Ala Ser Thr Leu Asp Ser
1               5
```

<210> SEQ ID NO 26
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 26

```
Leu Gln Tyr Ala Ser Tyr Pro Arg Thr
1               5
```

<210> SEQ ID NO 27
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 27

```
Glu Val Gln Leu Val Glu Ser Gly Gly Gly Leu Val Lys Pro Gly Gly
1               5                   10                  15

Ser Leu Lys Leu Pro Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Leu Tyr Tyr Asp His Val Leu Asp Tyr Trp Gly Gln Gly
            100                 105                 110

Thr Thr Leu Thr Val Ala Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
```

```
                  210                 215                 220
    Cys Pro Pro Cys Pro Ala Pro Pro Val Ala Gly Pro Ser Val Phe Leu
    225                 230                 235                 240

Phe Pro Pro Lys Pro Lys Asp Thr Leu Met Ile Ser Arg Thr Pro Glu
                    245                 250                 255

Val Thr Cys Val Val Val Asp Val Ser His Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Phe Arg Val Val Ser Val Leu
                290                 295                 300

Thr Val Val His Gln Asp Trp Leu Asn Gly Lys Glu Tyr Lys Cys Lys
    305                 310                 315                 320

Val Ser Asn Lys Gly Leu Pro Ala Pro Ile Glu Lys Thr Ile Ser Lys
                    325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Met Leu Asp Ser Asp Gly
    385                 390                 395                 400

Ser Phe Phe Leu Tyr Ser Lys Leu Thr Val Asp Lys Ser Arg Trp Gln
                    405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 28
<211> LENGTH: 1335
<212> TYPE: DNA
<213> ORGANISM: Artificial Sequence
<220> FEATURE:
<223> OTHER INFORMATION: synthetic polynucleotide

<400> SEQUENCE: 28
gaggtgcagc tggtggagtc tgggggaggc ttagtgaagc ctggagggtc cctgaaactc      60
ccctgtgcag cctctggatt cactttcagt gactatggaa tgcactgggt tcgtcaggct     120
ccagagaagg ggctggagtg ggttgcatac attagtagtg gcagtagtat catctactat     180
gcagacacac tgaagggccg attcaccatc tccagagaca tgccaagaa caccctgttc      240 ctgcaaatga ccagtctgag gtctgaggac acggccatgt attactgtgc aagggacctc     300
tactatgatc acgtccttga ctattggggc caaggcacca ctctcacagt cgcctcagct     360
agcaccaagg gaccctccgt gtttcctctg gctccttgct ccagatctac ctccgagtct     420
accgccgctc tgggttgtct ggtgaaggac tacttccccg agccagtgac cgtgtcttgg     480
aacagcggag ctctgacatc cggagtgcac acctttccag ccgtgctgca gtcttccggc     540
ctgtattctc tgtcctccgt ggtgaccgtg ccttcttcca acttcggcac ccagacctac     600
acttgcaacg tggaccacaa gcctccaac accaaggtgg acaagaccgt ggagcgcaag     660
tgttgcgtcg agtgccctcc ttgcccagct cctccagtgg ccggaccttc tgtgtttctg     720 ttcccccta agcctaagga caccctgatg atctcccgga ccccagaagt gacttgcgtg     780
```

```
gtggtggacg tgtctcacga ggaccccgag gtgcagttca attggtacgt ggacggcgtg    840
gaggtgcaca acgctaagac caagcccagg gaggagcagt tcaactccac cttccgggtg    900
gtgtcagtgc tgacagtggt gcaccaggat tggctgaacg gcaaggagta caagtgcaag    960
gtgtccaaca agggcctgcc agctcctatc gagaagacca tctccaagac caagggccag   1020
cccagagagc tcaggtgtac acactgcct ccttcccggg aggagatgac caagaaccag   1080
gtgtccctga cttgcctcgt gaagggattc taccccctccg acatcgcagt cgagtgggaa   1140
tccaacggcc agcccgagaa caactacaag accacccctc ctatgctgga ctccgacggc   1200
tccttcttcc tgtactccaa gctgaccgtg gacaagtccc gttggcagca gggcaacgtg   1260
ttctcttgca gcgtgatgca cgaggccctg cacaaccact acacccagaa gagcctgtcc   1320
ctgtctcccg gcaag                                                    1335
```

<210> SEQ ID NO 29
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 29

```
Asp Ile Gln Met Thr Gln Ser Pro Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ile Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Asn Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 642
<212> TYPE: DNA
<213> ORGANISM: Artificial Sequence
<220> FEATURE:

<223> OTHER INFORMATION: synthetic polynucleotide

<400> SEQUENCE: 30

```
gacatccaga tgacccagtc tccatcctcc ttatctgcct ctctgggaga aagagtcagt    60
ctcacttgtc gggcaagtca ggaaattagt ggttacttaa tctggcttca gcagaaacca   120
gatggaacta ttaaacgcct gatctacgcc gcatccactt tagattctgg tgtcccaaaa   180
aggttcagtg caataggtc tgggtcagat tattctctca ccatcagcag ccttgagtct    240
gaagattttg cagactatta ctgtctacaa tatgctagtt atcctcggac gttcggtgga   300
ggcaccaagc tggaaatcaa agaaccgtg gccgctcctt ccgtgttcat cttccctccc    360
tccgacgagc agctgaagag cggaacagcc tctgtcgtgt gcctcctgaa caacttctac   420
ccccgggagg ccaaggtcca gtggaaggtg acaacgctc tgcagagcgg caactctcag    480
gagagcgtga cagagcagga ctccaaggac tccacctact ccctgtcttc caccctgacc   540
ctgtctaagg ccgactacga gaagcacaag gtgtacgctt gcgaggtgac acaccaggga   600
ctgtcctctc cagtgaccaa gtccttcaac cgcggcgagt gt                      642
```

<210> SEQ ID NO 31
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 31

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Val Ile Tyr Tyr Val Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Asp Leu Tyr Tyr Asp His Val Leu Asp Ser Trp Gly Gln Gly
            100                 105                 110

Thr Thr Leu Thr Val Ser Ser
        115
```

<210> SEQ ID NO 32
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 32

```
gaggtgcagc tggtggagtc tgggggaggc ttagtgaagc ctggagggtc cctgaaactc    60
tcctgtgcag cctctggatt cactttcagt gactatggaa tgcactgggt tcgtcaggct   120
ccagagaagg ggctggagtg ggttgcatac attagtagcg gcagtagtgt catctactat   180
gtagacacag tgaagggccg attcaccatc tccagagaca tgccaagaa caccctgttc    240
ctgcaaatga ccagtctgag gtctgaggac acggccatgt attactgtgc aagggacctc   300
```

```
tactatgatc acgtccttga ctcctggggc caaggcacca ctctcacagt ctcctca    357
```

<210> SEQ ID NO 33
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 33

Asp Tyr Gly Met His
1               5

<210> SEQ ID NO 34
<211> LENGTH: 17
<212> TYPE: PRT
<213> ORGANISM: Artificial Sequence
<220> FEATURE:
<223> OTHER INFORMATION: synthetic polynucleotide

<400> SEQUENCE: 34

Tyr Ile Ser Ser Gly Ser Ser Val Ile Tyr Tyr Val Asp Thr Val Lys
1               5                   10                  15

Gly

<210> SEQ ID NO 35
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 35

Asp Leu Tyr Tyr Asp His Val Leu Asp Ser
1               5                   10

<210> SEQ ID NO 36
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 36

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Gly Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105

<210> SEQ ID NO 37
<211> LENGTH: 321
<212> TYPE: DNA

```
<213> ORGANISM: Artificial Sequence
<220> FEATURE:
<223> OTHER INFORMATION: synthetic polynucleotide

<400> SEQUENCE: 37
gacatccaga tgacccagtc tccatcctcc ttatctgcct ctctgggaga aagagtcagt    60
ctcacttgtc gggcaagtca ggaaattggt ggttacttaa gctggcttca gcagaaacca   120
gatggaacta ttaaacgcct gatctacgcc gcatccactt tagattctgg tgtcccaaaa   180
aggttcagtg gcagtaggtc tgggtcagat tattctctca ccatcagcag ccttgagtct   240
gaagattttg cagactatta ctgtctacaa tatgctagtt atcctcggac gttcggtgga   300
ggcaccaagc tggaaatcaa a                                             321

<210> SEQ ID NO 38
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 38

Arg Ala Ser Gln Glu Ile Gly Gly Tyr Leu Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 39

Ala Ala Ser Thr Leu Asp Ser
1               5

<210> SEQ ID NO 40
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 40

Leu Gln Tyr Ala Ser Tyr Pro Arg Thr
1               5

<210> SEQ ID NO 41
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 41

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Val Ile Tyr Tyr Val Asp Thr Val
    50                  55                  60
```

```
Lys Gly Arg Phe Thr Ile Ser Arg Asp Asn Ala Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Asp Leu Tyr Tyr Asp His Val Leu Asp Ser Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 42
<211> LENGTH: 1335
<212> TYPE: DNA
<213> ORGANISM: Artificial Sequence
<220> FEATURE:
<223> OTHER INFORMATION: synthetic polynucleotide
```

<400> SEQUENCE: 42

```
gaggtgcagc tggtggagtc tgggggaggc ttagtgaagc ctggagggtc cctgaaactc    60
tcctgtgcag cctctggatt cactttcagt gactatggaa tgcactgggt tcgtcaggct   120
ccagagaagg ggctggagtg ggttgcatac attagtagcg gcagtagtgt catctactat   180
gtagacacag tgaagggccg attcaccatc tccagagaca atgccaagaa caccctgttc   240
ctgcaaatga ccagtctgag gtctgaggac acggccatgt attactgtgc aagggacctc   300
tactatgatc acgtccttga ctcctggggc caaggcacca ctctcacagt ctcctcagct   360
agcaccaagg gaccctccgt gtttcctctg gctccttgct ccagatctac ctccgagtct   420
accgccgctc tgggttgtct ggtgaaggac tacttccccg agccagtgac cgtgtcttgg   480
aacagcggag ctctgacatc cggagtgcac acctttccag ccgtgctgca gtcttccggc   540
ctgtattctc tgtcctccgt ggtgaccgtg ccttcttcca acttcggcac ccagacctac   600
acttgcaacg tggaccacaa gcccccaaac accaaggtgg acaagaccgt ggagcgcaag   660
tgttgcgtcg agtgccctcc ttgcccagct cctccagtgg ccggaccttc tgtgtttctg   720
ttccccccta agcctaagga caccctgatg atctcccgga ccccagaagt gacttgcgtg   780
gtggtggacg tgtctcacga ggaccccgag gtgcagttca attggtacgt ggacggcgtg   840
gaggtgcaca cgctaagac caagcccagg gaggagcagt tcaactccac cttccgggtg   900
gtgtcagtgc tgacagtggt gcaccaggat tggctgaacg gcaaggagta caagtgcaag   960
gtgtccaaca agggcctgcc agctcctatc gagaagacca ctccaagac caagggccag  1020
cccagagagc ctcaggtgta cacactgcct ccttcccggg aggagatgac caagaaccag  1080
gtgtccctga cttgcctcgt gaagggattc taccctcg acatcgcagt cgagtgggaa  1140
tccaacggcc agcccgagaa caactacaag accacccctc ctatgctgga ctccgacggc  1200
tccttcttcc tgtactccaa gctgaccgtg gacaagtccc gttggcagca gggcaacgtg  1260
ttctcttgca gcgtgatgca cgaggccctg cacaaccact acacccagaa gagcctgtcc  1320
ctgtctcccg gcaag                                                   1335
```

<210> SEQ ID NO 43
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 43

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Gly Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 44
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 44

```
gacatccaga tgacccagtc tccatcctcc ttatctgcct ctctgggaga aagagtcagt      60
ctcacttgtc gggcaagtca ggaaattggt ggttacttaa gctggcttca gcagaaacca     120
gatggaacta ttaaacgcct gatctacgcc gcatccactt tagattctgg tgtcccaaaa     180
aggttcagtg gcagtaggtc tgggtcagat tattctctca ccatcagcag ccttgagtct     240
gaagattttg cagactatta ctgtctacaa tatgctagta tcctcggac gttcggtgga     300 ggcaccaagc tggaaatcaa agaaccgtg gccgctcctt ccgtgttcat cttccctccc      360
tccgacgagc agctgaagag cggaacagcc tctgtcgtgt gcctcctgaa caacttctac     420
ccccgggagg ccaaggtcca gtggaaggtg gacaacgctc tgcagagcgg caactctcag     480
gagagcgtga cagagcagga ctccaaggac tccacctact ccctgtcttc caccctgacc     540
ctgtctaagg ccgactacga aagcacaag gtgtacgctt gcgaggtgac acaccaggga     600
ctgtcctctc cagtgaccaa gtccttcaac cgcggcgagt gt                        642
```

<210> SEQ ID NO 45
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 45

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Arg Tyr Tyr Ala Asp Thr Val
    50                  55                  60

Lys Gly Arg Phe Thr Ile Ser Arg Asp Asn Ala Lys Asn Thr Leu Phe
65                  70                  75                  80
```

```
Leu Gln Met Thr Ser Leu Arg Ser Glu Asp Thr Ala Ile Tyr Tyr Cys
                85                  90                  95

Ala Arg Asp Leu Tyr Tyr Asp His Val Leu Asp Tyr Trp Gly Gln Gly
            100                 105                 110

Thr Thr Leu Thr Val Ser Ser
        115
```

<210> SEQ ID NO 46
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 46

```
gaggtgcagc tggtggagtc tggggggaggc ttagtgaagc ctggagggtc cctgaaactc      60
tcctgtgcag cctctggatt cactttcagt gactatggaa tgcattgggt tcgtcaggct     120
ccagagaagg ggctggagtg ggttgcatac attagtagtg gcagtagtat ccgctactat     180
gcagacacag tgaagggccg attcaccatc tccagagaca tgccaagaa caccctgttc       240 ctgcaaatga ccagtctgcg gtctgaggac acggccatat attactgtgc aagggacctc     300
tactatgatc acgtccttga ctactggggc caaggcacca ctctcacagt ctcctca        357
```

<210> SEQ ID NO 47
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 47

```
Asp Tyr Gly Met His
1               5
```

<210> SEQ ID NO 48
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 48

```
Tyr Ile Ser Ser Gly Ser Ser Ile Arg Tyr Tyr Ala Asp Thr Val Lys
1               5                   10                  15

Gly
```

<210> SEQ ID NO 49
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 49

```
Asp Leu Tyr Tyr Asp His Val Leu Asp Tyr
1               5                   10
```

<210> SEQ ID NO 50
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 50

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Val Ser Gly Tyr
            20                  25                  30

Leu Asn Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Val Glu Ile Lys
            100                 105

<210> SEQ ID NO 51
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 51

```
gacatccaga tgacccagtc tccatcctcc ttatctgcct ctctgggaga aagagtcagt      60
ctcacttgtc gggcaagtca ggaagttagt ggttacttaa actggcttca gcagaagcca     120
gatggaacta ttaaacgcct gatctacgcc gcatccactt tagattctgg tgtcccaaag     180
aggttcagtg gcagtaggtc tgggtcagat tattctctca ccatcagcag ccttgagtct     240
gaagattttg cagactatta ctgtctacaa tatgctagtt atcctcggac gttcggtgga     300
ggtaccaagg tggaaatcaa g                                               321
```

<210> SEQ ID NO 52
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 52

Arg Ala Ser Gln Glu Val Ser Gly Tyr Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 53

Ala Ala Ser Thr Leu Asp Ser
1               5

<210> SEQ ID NO 54
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 54

Leu Gln Tyr Ala Ser Tyr Pro Arg Thr
1               5

<210> SEQ ID NO 55
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 55

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Ile Arg Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Asp Leu Tyr Tyr Asp His Val Leu Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

```
Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 56
<211> LENGTH: 1335
<212> TYPE: DNA
<213> ORGANISM: Artificial Sequence
<220> FEATURE:
<223> OTHER INFORMATION: synthetic polynucleotide

<400> SEQUENCE: 56
```

| | | | | | |
|---|---|---|---|---|---|
| gaggtgcagc | tggtggagtc | tgggggaggc | ttagtgaagc | ctggagggtc | cctgaaactc | 60 |
| tcctgtgcag | cctctggatt | cactttcagt | gactatggaa | tgcattgggt | tcgtcaggct | 120 |
| ccagagaagg | ggctggagtg | ggttgcatac | attagtagtg | gcagtagtat | ccgctactat | 180 |
| gcagacacag | tgaagggccg | attcaccatc | tccagagaca | atgccaagaa | caccctgttc | 240 |
| ctgcaaatga | ccagtctgcg | gtctgaggac | acggccatat | attactgtgc | aagggacctc | 300 |
| tactatgatc | acgtccttga | ctactggggc | caaggcacca | ctctcacagt | ctcctcagct | 360 |
| agcaccaagg | gaccctccgt | gtttcctctg | gctccttgct | ccagatctac | tccgagtctt | 420 |
| accgccgctc | tgggttgtct | ggtgaaggac | tactttcccg | agccagtgac | cgtgtcttgg | 480 |
| aacagcggag | ctctgacatc | cggagtgcac | acctttccag | ccgtgctgca | gtcttccggc | 540 |
| ctgtattctc | tgtcctccgt | ggtgaccgtg | ccttcttcca | acttcggcac | ccagacctac | 600 |
| acttgcaacg | tggaccacaa | gccctccaac | accaaggtgg | acaagaccgt | ggagcgcaag | 660 |
| tgttgcgtcg | agtgccctcc | ttgcccagct | cctccagtgg | ccggaccttc | tgtgtttctg | 720 |
| ttccccccta | agcctaagga | caccctgatg | atctcccgga | ccccagaagt | gacttgcgtg | 780 |
| gtggtggacg | tgtctcacga | ggaccccgag | gtgcagttca | attggtacgt | ggacggcgtg | 840 |
| gaggtgcaca | acgctaagac | caagcccagg | gaggagcagt | tcaactccac | cttccgggtg | 900 |
| gtgtcagtgc | tgacagtggt | gcaccaggat | tggctgaacg | gcaaggagta | caagtgcaag | 960 |
| gtgtccaaca | agggcctgcc | agctcctatc | gagaagacca | tctccaagac | caagggccag | 1020 |
| cccagagagc | ctcaggtgta | cactctgcct | ccttcccggg | aggagatgac | caagaaccag | 1080 |
| gtgtccctga | cttgcctcgt | gaagggattc | taccctccg | acatcgcagt | cgagtgggaa | 1140 |
| tccaacggcc | agcccgagaa | caactacaag | accacccctc | ctatgctgga | ctccgacggc | 1200 |
| tccttcttcc | tgtactccaa | gctgaccgtg | gacaagtccc | gttggcagca | gggcaacgtg | 1260 |
| ttctcttgca | gcgtgatgca | cgaggccctg | cacaaccact | acacccagaa | gagcctgtcc | 1320 |
| ctgtctcccg | gcaag | | | | | 1335 |

<210> SEQ ID NO 57

```
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 57

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Val Ser Gly Tyr
            20                  25                  30

Leu Asn Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 58
gacatccaga tgacccagtc tccatcctcc ttatctgcct ctctgggaga aagagtcagt      60
ctcacttgtc gggcaagtca ggaagttagt ggttacttaa actggcttca gcagaagcca    120
gatggaacta ttaaacgcct gatctacgcc gcatccactt tagattctgg tgtcccaaag    180
aggttcagtg gcagtaggtc tgggtcagat tattctctca ccatcagcag ccttgagtct    240
gaagattttg cagactatta ctgtctacaa tatgctagtt atcctcggac gttcggtgga    300
ggtaccaagg tggaaatcaa agaaccgtg gccgctcctt ccgtgttcat cttccctccc    360
tccgacgagc agctgaagag cggaacagcc tctgtcgtgt gcctcctgaa caacttctac    420
ccccgggagg ccaaggtcca gtggaaggtg gacaacgctc tgcagagcgg caactctcag    480
gagagcgtga cagagcagga ctccaaggac tccacctact ccctgtcttc caccctgacc    540
ctgtctaagg ccgactacga aagcacaag gtgtacgctt gcgaggtgac acaccaggga    600
```

```
ctgtcctctc cagtgaccaa gtccttcaac cgcggcgagt gt 642
```

```
<210> SEQ ID NO 59
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 59

Ala Ala Ser Thr Leu Glu Ser
1 5
```

```
<210> SEQ ID NO 60
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 60

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asp Tyr
20 25 30

Gly Met His Trp Val Arg Gln Ala Pro Gly Lys Gly Leu Glu Trp Val
35 40 45

Ala Tyr Ile Ser Ser Gly Ser Ser Ile Met Tyr Tyr Ala Asp Thr Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Leu Tyr Tyr Asp His Val Leu Asp Tyr Trp Gly Gln Gly
100 105 110

Thr Thr Val Thr Val Ser Ser
115
```

```
<210> SEQ ID NO 61
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 61
caagtgcagc tcgtcgaaag cggaggaggc gtggtgcagc ccggaaggtc tctgagactg 60
agctgtgctg ccagcggctt cactttcagc gactacggca tgcactgggt cagacaagcc 120
cccggcaagg gactggaatg ggtcgcttac atcagctccg gcagcagcat catgtactac 180
gccgacacag tgaagggaag gttcacaatc tctagggaca acagcaagaa cacactctat 240
```

```
ctgcagatga actccctcag agccgaggat acagctgtgt actactgcgc tagggatctg 300
tactacgacc acgtgctcga ttactggggc caaggcacaa cagtgacagt gagcagc 357
```

```
<210> SEQ ID NO 62
<211> LENGTH: 107
<212> TYPE: PRT
<213> ORGANISM: Artificial Sequence
<220> FEATURE:
<223> OTHER INFORMATION: synthetic polypeptide
```

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Val Ser Gly Tyr
            20                  25                  30

Leu Asn Trp Leu Gln Gln Lys Pro Gly Lys Ala Ile Lys Arg Leu Ile
        35                  40                  45

Tyr Ala Ala Ser Thr Leu Glu Ser Gly Val Pro Ser Arg Phe Ser Gly
50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Arg
                85                  90                  95

Thr Phe Gly Gln Gly Thr Lys Val Glu Ile Lys
            100                 105

<210> SEQ ID NO 63
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 63
gacatccaga tgactcagag cccaagctct ctgagcgcca gcgtgggaga tagggtcaca      60
atcacttgta gggccagcca agaggtgagc ggctatctga attggctcca gcagaaaccc     120
ggcaaggcca tcaagagact gatctatgcc gccagcactc tggagtccgg agtgccatct     180
aggttcagcg gcagcagaag cggcagcgac tacactctca caatcagctc cctccagcca     240
gaagacttcg ccacttacta ctgtctgcag tatgccagct acccaaggac tttcggacag     300
ggtaccaagg tggagatcaa a                                                321

<210> SEQ ID NO 64
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Tyr Ile Ser Ser Gly Ser Ser Ile Met Tyr Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Tyr Asp His Val Leu Asp Tyr Trp Gly Gln Gly
            100                 105                 110

Thr Thr Val Thr Val Ser Ser Ala Ser Thr Lys Gly Pro Ser Val Phe
        115                 120                 125

```
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 65
<211> LENGTH: 1335
<212> TYPE: DNA
<213> ORGANISM: Artificial Sequence
<220> FEATURE:
<223> OTHER INFORMATION: synthetic polynucleotide

<400> SEQUENCE: 65
caagtgcagc tcgtcgaaag cggaggaggc gtggtgcagc ccggaaggtc tctgagactg      60
agctgtgctg ccagcggctt cactttcagc gactacggca tgcactgggt cagacaagcc     120
cccggcaagg gactggaatg ggtcgcttac atcagctccg gcagcagcat catgtactac     180
gccgacacag tgaagggaag gttcacaatc tctagggaca cagcaagaa cacactctat      240
```

```
ctgcagatga actccctcag agccgaggat acagctgtgt actactgcgc tagggatctg    300
tactacgacc acgtgctcga ttactggggc caaggcacaa cagtgacagt gagcagcgct    360
agcaccaagg gaccctccgt gtttcctctg gctccttgct ccagatctac ctccgagtct    420
accgccgctc tgggttgtct ggtgaaggac tacttccccg agccagtgac cgtgtcttgg    480
aacagcggag ctctgacatc cggagtgcac acctttccag ccgtgctgca gtcttccggc    540
ctgtattctc tgtcctccgt ggtgaccgtg ccttcttcca acttcggcac ccagacctac    600
acttgcaacg tggaccacaa gccctccaac accaaggtgg acaagaccgt ggagcgcaag    660
tgttgcgtcg agtgccctcc ttgcccagct cctccagtgg ccggaccttc tgtgtttctg    720
ttccccccta agcctaagga caccctgatg atctcccgga ccccagaagt gacttgcgtg    780
gtggtggacg tgtctcacga ggaccccgag gtgcagttca attggtacgt ggacggcgtg    840
gaggtgcaca acgctaagac caagcccagg gaggagcagt tcaactccac cttccgggtg    900
gtgtcagtgc tgacagtggt gcaccaggat tggctgaacg gcaaggagta caagtgcaag    960
gtgtccaaca agggcctgcc agctcctatc gagaagacca tctccaagac caagggccag   1020
cccagagagc tcaggtgtta cactgctgcc ccttcccggg aggagatgac caagaaccag   1080
gtgtccctga cttgcctcgt gaagggattc taccctccg acatcgcagt cgagtgggaa    1140
tccaacggcc agcccgagaa caactacaag accacccctc ctatgctgga ctccgacggc   1200
tccttcttcc tgtactccaa gctgaccgtg gacaagtccc gttggcagca gggcaacgtg   1260
ttctcttgca gcgtgatgca cgaggccctg cacaaccact acacccagaa gagcctgtcc   1320
ctgtctcccg gcaag                                                    1335
```

<210> SEQ ID NO 66
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Val Ser Gly Tyr
                20                  25                  30

Leu Asn Trp Leu Gln Gln Lys Pro Gly Lys Ala Ile Lys Arg Leu Ile
            35                  40                  45

Tyr Ala Ala Ser Thr Leu Glu Ser Gly Val Pro Ser Arg Phe Ser Gly
        50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser 165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 67
gacatccaga tgactcagag cccaagctct ctgagcgcca gcgtgggaga tagggtcaca      60
atcacttgta gggccagcca agaggtgagc ggctatctga attggctcca gcagaaaccc     120
ggcaaggcca tcaagagact gatctatgcc gccagcactc tggagtccgg agtgccatct     180
aggttcagcg gcagcagaag cggcagcgac tacactctca caatcagctc cctccagcca     240
gaagacttcg ccacttacta ctgtctgcag tatgccagct acccaaggac tttcggacag     300
ggtaccaagg tggagatcaa agaaccgtg gccgctcctt ccgtgttcat cttccctccc      360
tccgacgagc agctgaagag cggaacagcc tctgtcgtgt gcctcctgaa caacttctac     420
ccccgggagg ccaaggtcca gtggaaggtg acaacgctc tgcagagcgg caactctcag      480
gagagcgtga cagagcagga ctccaaggac tccacctact ccctgtcttc caccctgacc     540
ctgtctaagg ccgactacga aagcacaag gtgtacgctt gcgaggtgac acaccaggga      600
ctgtcctctc cagtgaccaa gtccttcaac cgcggcgagt gt                        642

<210> SEQ ID NO 68
<211> LENGTH: 107
<212> TYPE: PRT
<213> ORGANISM: Artificial Sequence
<220> FEATURE:
<223> OTHER INFORMATION: synthetic polynucleotide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Arg Gly Tyr
            20                  25                  30

Leu Ile Trp Leu Gln Gln Lys Pro Gly Lys Ala Ile Lys Arg Leu Ile
        35                  40                  45

Tyr Ala Ala Ser Thr Leu Glu Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Thr Ser Tyr Pro Arg
                85                  90                  95

Thr Phe Gly Gln Gly Thr Lys Val Glu Ile Lys
            100                 105

<210> SEQ ID NO 69
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 69
gacatccaga tgacacagtc ccctagctct ctgtccgcca gcgtgggaga tagggtgaca        60
atcacttgta gggccagcca agagattagg ggctatctga tctggctgca gcagaaaccc       120
ggcaaggcca tcaagaggct gatctacgcc gccagcactc tggagagcgg agtcccaagc       180
agattttccg gcagccgctc cggcagcgat tacactctca caatcagctc tctgcagcca       240
gaggacttcg ccacttacta ctgtctgcag tacacaagct acccaaggac attcggccaa       300
ggcactaagg tggagatcaa a                                                 321

<210> SEQ ID NO 70
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Arg Gly Tyr
            20                  25                  30

Leu Ile Trp Leu Gln Gln Lys Pro Gly Lys Ala Ile Lys Arg Leu Ile
        35                  40                  45

Tyr Ala Ala Ser Thr Leu Glu Ser Gly Val Pro Ser Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Thr Ser Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 71

```
gacatccaga tgacacagtc ccctagctct ctgtccgcca gcgtgggaga tagggtgaca    60
atcacttgta gggccagcca agagattagg ggctatctga tctggctgca gcagaaaccc   120
ggcaaggcca tcaagaggct gatctacgcc gccagcactc tggagagcgg agtcccaagc   180
agattttccg gcagccgctc cggcagcgat tacactctca caatcagctc tctgcagcca   240
gaggacttcg ccacttacta ctgtctgcag tacacaagct acccaaggac attcggccaa   300
ggcactaagg tggagatcaa agaaccgtg gccgctcctt ccgtgttcat cttccctccc   360
tccgacgagc agctgaagag cggaacagcc tctgtcgtgt gcctcctgaa caacttctac   420
ccccgggagg ccaaggtcca gtggaaggtg gacaacgctc tgcagagcgg caactctcag   480
gagagcgtga cagagcagga ctccaaggac tccacctact ccctgtcttc caccctgacc   540
ctgtctaagg ccgactacga aagcacaag gtgtacgctt gcgaggtgac acaccaggga   600
ctgtcctctc cagtgaccaa gtccttcaac cgcggcgagt gt                      642
```

<210> SEQ ID NO 72
<211> LENGTH: 119
<212> TYPE: PRT
<213> ORGANISM: Artificial Sequence
<220> FEATURE:
<223> OTHER INFORMATION: synthetic polypeptide

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Ile Met Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Tyr Tyr Asp His Val Leu Asp Tyr Trp Gly Gln Gly
            100                 105                 110

Thr Leu Leu Thr Val Ser Ser
        115

<210> SEQ ID NO 73
<211> LENGTH: 357
<212> TYPE: DNA
<213> ORGANISM: Artificial Sequence
<220> FEATURE:
<223> OTHER INFORMATION: synthetic polynucleotide

<400> SEQUENCE: 73

```
gaggtgcagc tggtggagag cggcggcggc ctggtgcagc ccggcggcag cctgagactg    60
agctgcgccg ccagcggctt caccttcagc gactacggca tgcactgggt gagacaggcc   120
cccggcaagg gcctggagtg ggtgagctac atcagcagcg gcagcagcat catgtactac   180
gccgacaccg tgaagggcag attcaccatc agcagagaca acgccaagaa cagcctgtac   240
ctgcagatga acagcctgag agccgaggac accgccgtgt actactgcgc cagagacctg   300
tactacgacc acgtgctgga ctactggggc cagggcaccc tgctgaccgt gagcagc      357
```

```
<210> SEQ ID NO 74
<211> LENGTH: 107
<212> TYPE: PRT
<213> ORGANISM: Artificial Sequence
<220> FEATURE:
<223> OTHER INFORMATION: synthetic polypeptide

<400> SEQUENCE: 74
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Arg Gly Tyr
            20                  25                  30

Leu Ile Trp Leu Gln Gln Lys Pro Gly Gly Ala Ile Lys Arg Leu Ile
        35                  40                  45

Tyr Ala Ala Ser Thr Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Thr Ser Tyr Pro Arg
                85                  90                  95

Thr Phe Gly Gly Gly Thr Lys Val Glu Ile Lys
            100                 105

```
<210> SEQ ID NO 75
<211> LENGTH: 321
<212> TYPE: DNA
<213> ORGANISM: Artificial Sequence
<220> FEATURE:
<223> OTHER INFORMATION: synthetic polynucleotide

<400> SEQUENCE: 75
```

| | |
|---|---|
| gacatccaga tgacccagag ccccagcagc ctgagcgcca gcgtgggcga cagagtgacc | 60 |
| atcacctgca gagccagcca ggagatcaga ggctacctga tctggctgca gcagaagccc | 120 |
| ggcggcgcca tcaagagact gatctacgcc gccagcaccc tggagagcgg cgtgcccagc | 180 |
| agattcagcg gcagcagaag cggcaccgac ttcaccctga ccatcagcag cctgcagccc | 240 |
| gaggacttcg ccacctacta ctgcctgcag tacaccagct accccagaac cttcggcggc | 300 |
| ggtaccaagg tggagatcaa g | 321 |

```
<210> SEQ ID NO 76
<211> LENGTH: 445
<212> TYPE: PRT
<213> ORGANISM: Artificial Sequence
<220> FEATURE:
<223> OTHER INFORMATION: synthetic polypeptide

<400> SEQUENCE: 76
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Ser Ile Met Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

```
Ala Arg Asp Leu Tyr Tyr Asp His Val Leu Asp Tyr Trp Gly Gln Gly
            100                 105                 110

Thr Leu Leu Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 77
<211> LENGTH: 1335
<212> TYPE: DNA
<213> ORGANISM: Artificial Sequence
<220> FEATURE:
<223> OTHER INFORMATION: synthetic polynucleotide

<400> SEQUENCE: 77
gaggtgcagc tggtggagag cggcggcggc ctggtgcagc ccggcggcag cctgagactg      60
```

```
agctgcgccg ccagcggctt caccttcagc gactacggca tgcactgggt gagacaggcc    120
cccggcaagg gcctggagtg ggtgagctac atcagcagcg gcagcagcat catgtactac    180
gccgacaccg tgaagggcag attcaccatc agcagagaca cgccaagaa  cagcctgtac    240
ctgcagatga acagcctgag agccgaggac accgccgtgt actactgcgc cagagacctg    300
tactacgacc acgtgctgga ctactgggc caggggcacccc tgctgaccgt gagcagcgct    360
agcaccaagg gcccctccgt gtttcctctg gctccttgct ccagatctac ctccgagtct    420
accgccgctc tgggttgtct ggtgaaggac tacttccccg agccagtgac cgtgtcttgg    480
aacagcggag ctctgacatc cggagtgcac acctttccag ccgtgctgca gtcttccggc    540
ctgtattctc tgtcctccgt ggtgaccgtg ccttcttcca acttcggcac ccagacctac    600
acttgcaacg tggaccacaa gcccctccaac accaaggtgg acaagaccgt ggagcgcaag    660
tgttgcgtcg agtgccctcc ttgcccagct cctccagtgg ccggaccttc tgtgtttctg    720
ttccccccta agcctaagga caccctgatg atctcccgga ccccagaagt gacttgcgtg    780
gtggtggacg tgtctcacga ggaccccgag gtgcagttca attggtacgt ggacggcgtg    840
gaggtgcaca acgctaagac caagcccagg gaggagcagt tcaactccac cttccgggtg    900
gtgtcagtgc tgacagtggt gcaccaggat tggctgaacg gcaaggagta caagtgcaag    960
gtgtccaaca agggcctgcc agctcctatc gagaagacca tctccaagac caagggccag   1020
cccagagagc ctcaggtgta cactgcct cc cttcccggg aggagatgac caagaaccag   1080
gtgtccctga cttgcctcgt gaagggattc taccccctcc gacatcgcagt cgagtgggaa   1140
tccaacggcc agcccgagaa caactacaag accacccctc ctatgctgga ctccgacggc   1200
tccttcttcc tgtactccaa gctgaccgtg acaagtccc gttggcagca gggcaacgtg   1260
ttctcttgca gcgtgatgca cgaggccctg cacaaccact acacccagaa gagcctgtcc   1320
ctgtctcccg gcaag                                                    1335
```

<210> SEQ ID NO 78
<211> LENGTH: 214
<212> TYPE: PRT
<213> ORGANISM: Artificial Sequence
<220> FEATURE:
<223> OTHER INFORMATION: synthetic polypeptide

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Arg Gly Tyr
            20                  25                  30

Leu Ile Trp Leu Gln Gln Lys Pro Gly Gly Ala Ile Lys Arg Leu Ile
        35                  40                  45

Tyr Ala Ala Ser Thr Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Thr Ser Tyr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                   130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 79
<211> LENGTH: 642
<212> TYPE: DNA
<213> ORGANISM: Artificial Sequence
<220> FEATURE:
<223> OTHER INFORMATION: synthetic polynucleotide

<400> SEQUENCE: 79
gacatccaga tgacccagag ccccagcagc ctgagcgcca gcgtgggcga cagagtgacc      60
atcacctgca gagccagcca ggagatcaga ggctacctga tctggctgca gcagaagccc    120
ggcggcgcca tcaagagact gatctacgcc gccagcaccc tggagagcgg cgtgcccagc    180
agattcagcg gcagcagaag cggcaccgac ttcaccctga ccatcagcag cctgcagccc    240
gaggacttcg ccacctacta ctgcctgcag tacaccagct accccagaac cttcggcggc    300
ggtaccaagg tggagatcaa gagaaccgtg gccgctcctt ccgtgttcat cttccctccc    360
tccgacgagc agctgaagag cggaacagcc tctgtcgtgt gcctcctgaa caacttctac    420 ccccggggagg ccaaggtcca gtggaaggtg gacaacgctc tgcagagcgg caactctcag    480
gagagcgtga cagagcagga ctccaaggac tccacctact ccctgtcttc caccctgacc    540
ctgtctaagg ccgactacga gaagcacaag gtgtacgctt gcgaggtgac acaccaggga    600
ctgtcctctc cagtgaccaa gtccttcaac cgcggcgagt gt                        642
```

BINDING MOLECULE SPECIFIC FOR CD39 AND USE THEREOF

CROSS-REFERENCE TO RELATED APPLICATIONS

This application is a U.S. National Phase application of Int'l Appl. No. PCT/CN2020/126351, filed Nov. 4, 2020, which claims priority to Int'l Appl. No. PCT/CN2019/115505, filed Nov. 5, 2019, each of which are incorporated herein by reference in their entireties.

TECHNICAL FIELD

This invention relates to an antibody or antigen-binding fragment thereof specifically binds to CD39, and to use of the antibody or antigen-binding fragment thereof of this invention in the treatment of a disease, and to a treatment method using the antibody or antigen-binding fragment thereof of this invention.

BACKGROUND ART

CD39 is a membrane protein that hydrolyzes ATP and ADP in a $Ca^{2+}$ and $Mg^{2+}$ fashion to yield AMP. Human CD39 has 510 amino acids, predicted with seven N-linked glycosylation sites, 11 Cys residues, and two transmembrane regions. CD39 is composed of two transmembrane domains, a small cytoplasmic domain comprising the $NH_2$— and COOH— terminal segments, and a large extracellular hydrophobic domain consisting of five highly conserved domains, known as apyrase conserved regions (ACR) 1-5, which are pivotal for the catabolic activity of the enzyme. The amino acid sequences of ACR1 and ACR5 contain a phosphate-binding motif (DXG), which is critical for stabilizing the interaction between the enzyme and its nucleotide substrate during phosphate cleavage. In addition, two ACR residues, i.e., Glu 174 of ACR 3 and Ser 218 of ACR 4 are also necessary for enzyme function. CD39 becomes catalytically active when located on the cell surface, and its glycosylation is crucial for correct protein folding, membrane targeting, and enzyme activity (Antonioli L et al (2013), Trends Mol Med, 19(6):355-367).

CD39 is constitutively expressed in spleen, thymus, lung, and placenta, and in these organs, it is associated primarily with endothelial cells and immune cell populations, such as B cells, natural killer (NK) cells, dendritic cells, Langerhans cells, monocytes, macrophages, mesangial cell, neutrophils and regulatory T cells (Tregs). The expression of CD39 is regulated by several pro-inflammatory cytokines, oxidative stress and hypoxia through the transcription factors Sp1, Stat3, and zinc finger protein growth factor independent-1 transcription factor (Antonioli L et al (2013), Trends Mol Med, 19(6):355-367).

Under physiological conditions, purine medium ATP mainly exists in the cytoplasm, with a concentration of about 1~10 mM; while the extracellular ATP concentration is at a low level, 10~100 nM; and when the body appears disorder, such as inflammation, ischemia, malignant tumors and the like, ATP in the cytoplasm is released to the outside of the cell in a large amount, triggering an immune response as a sensory signal and an outgoing signal. After ATP is released to the outside of the cell, it is hydrolyzed by extracellular CD39 into ADP and AMP, and an immunosuppressive adenosine is produced from AMP under the synergistic action of CD37. In this process, CD39 is rate-limiting enzyme (Faas M M et al. (2017), Mol Aspects Med, 55:9-19). CD39 and CD73 can regulate the function of several immune cells, including lymphocytes, neutrophils, monocytes/macrophages, and dendritic cells and so on (Antonioli L et al (2013), Trends Mol Med, 19(6):355-367). In the tumor microenvironment, CD39 is highly expressed on the surface of Treg cells, and CD39 is gradually recognized as a specific marker molecule on the surface of Treg cells (Gu J et al (2017), Cell Mol Immunol, 14(6):521-528). Adenosine derived from Treg cells acts on A2A receptors on the surface of lymphocytes (Sundstrom P S H et al (2016), Cancer Immunol Res, 4(3):183-193; Ma S R et al (2017), Mol Cancer, 16(1):99) to inhibit the proliferation, migration and anti-tumor effects of effector T cells; and inhibit the cytotoxicity of NK cells and the production of cytokines, and mediate a series of immunosuppressive effects (Lokshin A et al (2006), Cancer Res, 66(15):7758-7765; Hu G et al (2017), Oncoimmunology, 6(2): e1277305).

CD39 is highly expressed in many malignant tumors (Allard B et al (2017), Immunol Rev, 276(1):121-144; Bastid J et al (2013), Oncogene, 32(14):1743-1751). Compared with normal tissues, the expression level of CD39 in tumor tissues such as kidney, lung, ovary, pancreas, thyroid and so on is significantly increased, suggesting that the abnormally high expression of CD39 is associated with the development of malignant tumors (Bastid J et al. (2015), Cancer Immunol Res, 3(3): 254-265). In addition, changes in the CD39/CD73 system may disrupt potentially complex mechanisms, such as immune tolerance of autoantigens driven by Treg, and thus contribute to the development of some autoimmune diseases (Karen M. Dwyer et al. (2007), Purinergic Signal, 3(1-2): 171-180).

Currently, there is no drug for an inhibitor against the CD39 target in the market. There is an urgent need for research and development of a CD39 inhibitor and development of a treatment method for a disease related to CD39.

SUMMARY OF INVENTION

The invention provides an antibody or antigen-binding fragment specifically binding to CD39 and use thereof in the treatment of a disease.

In one respect, the invention provides an antibody or antigen-binding fragment thereof comprising a heavy chain variable region that comprises HCDR1, HCDR2, HCDR3; and a light chain variable region that comprises LCDR1, LCDR2, LCDR3, wherein:
  (a) the HCDR1 comprises an amino acid sequence selected from a group consisting of SEQ ID NOs: 5, 19, 33 and/or 47, and conservative modifications thereof;
  (b) the HCDR2 comprises an amino acid sequence selected from a group consisting of SEQ ID NOs: 6, 20, 34 and/or 48, and conservative modifications thereof;
  (c) the HCDR3 comprises an amino acid sequence selected from a group consisting of SEQ ID NOs: 7, 21, 35 and/or 49, and conservative modifications thereof;
  (d) the LCDR1 comprises an amino acid sequence selected from a group consisting of SEQ ID NOs: 10, 24, 38 and/or 52, and conservative modifications thereof;
  (e) the LCDR2 comprises an amino acid sequence selected from a group consisting of SEQ ID NOs: 11, 25, 39, 53 and/or 59, and conservative modifications thereof; and
  (f) the LCDR3 comprises an amino acid sequence selected from a group consisting of SEQ ID NOs: 12, 26, 40 and/or 54, and conservative modifications thereof.

In some embodiments, the antibody or antigen-binding fragment thereof comprises:
1) (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 11, and (f) LCDR3 comprising SEQ ID NO: 12;
2) (a) HCDR1 comprising SEQ ID NO: 19, (b) HCDR2 comprising SEQ ID NO: 20, (c) HCDR3 comprising SEQ ID NO: 21, (d) LCDR1 comprising SEQ ID NO: 24, (e) LCDR2 comprising SEQ ID NO: 25, and (f) LCDR3 comprising SEQ ID NO: 26;
3) (a) HCDR1 comprising SEQ ID NO: 33, (b) HCDR2 comprising SEQ ID NO: 34, (c) HCDR3 comprising SEQ ID NO: 35, (d) LCDR1 comprising SEQ ID NO: 38, (e) LCDR2 comprising SEQ ID NO:39, and (f) LCDR3 comprising SEQ ID NO: 40;
4) (a) HCDR1 comprising SEQ ID NO: 47, (b) HCDR2 comprising SEQ ID NO: 48, (c) HCDR3 comprising SEQ ID NO: 49, (d) LCDR1 comprising SEQ ID NO: 52, (e) LCDR2 comprising SEQ ID NO: 53, and (f) LCDR3 comprising SEQ ID NO: 54;
5) (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 52, (e) LCDR2 comprising SEQ ID NO: 59, and (f) LCDR3 comprising SEQ ID NO: 54; and/or
6) (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 59, and (f) LCDR3 comprising SEQ ID NO: 12.

In some embodiments, the antibody or antigen-binding fragment thereof comprises: (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 11, and (f) LCDR3 comprising SEQ ID NO: 12.

In some embodiments, the antibody or antigen-binding fragment thereof comprises: (a) HCDR1 comprising SEQ ID NO: 19, (b) HCDR2 comprising SEQ ID NO: 20, (c) HCDR3 comprising SEQ ID NO: 21, (d) LCDR1 comprising SEQ ID NO: 24, (e) LCDR2 comprising SEQ ID NO:25, and (f) LCDR3 comprising SEQ ID NO: 26.

In some embodiments, the antibody or antigen-binding fragment thereof comprises: (a) HCDR1 comprising SEQ ID NO: 33, (b) HCDR2 comprising SEQ ID NO: 34, (c) HCDR3 comprising SEQ ID NO: 35, (d) LCDR1 comprising SEQ ID NO: 38, (e) LCDR2 comprising SEQ ID NO: 39, and (f) LCDR3 comprising SEQ ID NO: 40.

In some embodiments, the antibody or antigen-binding fragment thereof comprises: (a) HCDR1 comprising SEQ ID NO: 47, (b) HCDR2 comprising SEQ ID NO: 48, (c) HCDR3 comprising SEQ ID NO: 49, (d) LCDR1 comprising SEQ ID NO: 52, (e) LCDR2 comprising SEQ ID NO: 53, and (f) LCDR3 comprising SEQ ID NO: 54.

In some embodiments, the antibody or antigen-binding fragment thereof comprises: (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 52, (e) LCDR2 comprising SEQ ID NO: 59, and (f) LCDR3 comprising SEQ ID NO: 54.

In some embodiments, the antibody or antigen-binding fragment thereof comprises: (a) HCDR1 comprising SEQ ID NO: 5, (b) HCDR2 comprising SEQ ID NO: 6, (c) HCDR3 comprising SEQ ID NO: 7, (d) LCDR1 comprising SEQ ID NO: 10, (e) LCDR2 comprising SEQ ID NO: 59, and (f) LCDR3 comprising SEQ ID NO:12.

In some embodiments, the antibody or antigen-binding fragment thereof comprises:
(i) the heavy chain variable region (VH) comprising an amino acid sequence with at least 85% identity to an amino acid sequence selected from a group consisting of SEQ ID NOs: 3, 17, 31, 45, 60 and/or 72, and conservative modifications thereof; and
(ii) the light chain variable region (VL) comprising an amino acid sequence with at least 85% identity to an amino acid sequence selected from a group consisting of SEQ ID NOs: 8, 22, 36, 50, 62, 68 and/or 74, and conservative modifications thereof.

In some embodiments, the heavy chain variable region comprises an amino acid sequence with at least 90%, at least 95%, at least 96%, at least 97%, at least 98%, at least 99%, or 100% identity to the heavy chain variable region selected from (i); and the light chain variable region comprises an amino acid sequence with at least 90%, at least 95%, at least 96%, at least 97%, at least 98%, at least 99%, or 100% identity to the light chain variable region selected from (ii).

In some embodiments, the antibody or antigen-binding fragment thereof comprises:
1) a heavy chain variable region (VH) that comprises an amino acid sequence with at least 85% identity to an amino acid sequence of SEQ ID NO: 3, and a light chain variable region (VL) that comprises an amino acid sequence with at least 85% identity to an amino acid sequence of SEQ ID NO: 8;
2) a heavy chain variable region (VH) that comprises an amino acid sequence with at least 85% identity to an amino acid sequence of SEQ ID NO: 17, and a light chain variable region (VL) that comprises an amino acid sequence with at least 85% identity to an amino acid sequence of SEQ ID NO: 22;
3) a heavy chain variable region (VH) that comprises an amino acid sequence with at least 85% identity to an amino acid sequence of SEQ ID NO: 31, and a light chain variable region (VL) that comprises an amino acid sequence with at least 85% identity to an amino acid sequence of SEQ ID NO: 36;
4) a heavy chain variable region (VH) that comprises an amino acid sequence with at least 85% identity to an amino acid sequence of SEQ ID NO: 45, and a light chain variable region (VL) that comprises an amino acid sequence with at least 85% identity to an amino acid sequence of SEQ ID NO: 50;
5) a heavy chain variable region (VH) that comprises an amino acid sequence with at least 85% identity to an amino acid sequence of SEQ ID NO: 60, and a light chain variable region (VL) that comprises an amino acid sequence with at least 85% identity to an amino acid sequence of SEQ ID NO: 62;
6) a heavy chain variable region (VH) that comprises an amino acid sequence with at least 85% identity to an amino acid sequence of SEQ ID NO: 60, and a light chain variable region (VL) that comprises an amino acid sequence with at least 85% identity to an amino acid sequence of SEQ ID NO: 68; and/or
7) a heavy chain variable region (VH) that comprises an amino acid sequence with at least 85% identity to an amino acid sequence of SEQ ID NO: 72, and a light chain variable region (VL) that comprises an amino acid sequence with at least 85% identity to an amino acid sequence of SEQ ID NO: 74.

In some embodiments, the heavy chain variable region and the light chain variable region comprise an amino acid sequence with at least 90%, at least 95%, at least 96%, at least 97%, at least 98%, at least 99%, or 100% identity to the heavy chain variable region and the light chain variable region selected from 1)-7), respectively.

In some embodiments, the heavy chain constant region of the antibody is an IgG.

In some embodiments, the heavy chain constant region of the antibody is selected from IgG1, IgG2 or IgG4.

In some embodiments, the antibody is a monoclonal antibody, a chimeric antibody, a humanized antibody, a human engineered antibody, a human antibody, Fv, a single chain antibody (scFv), Fab, Fab', Fab'-SH or F(ab')2.

In some embodiments, the antibody or antigen-binding fragment thereof comprises a heavy chain and a light chain, wherein:
(I) the heavy chain comprises an amino acid sequence with at least 85% identity to an amino acid sequence selected from a group of SEQ ID NOs: 13, 27, 41, 55, 64 and/or 76, and conservative modifications thereof; and
(II) the light chain comprises an amino acid sequence with at least 85% identity to an amino acid sequence selected from a group of SEQ ID NOs: 15, 29, 43, 57, 66, 70 and/or 78, and conservative modifications thereof.

In some embodiments, the heavy chain comprises an amino acid sequence with at least 90%, at least 95%, at least 96%, at least 97%, at least 98%, at least 99%, or 100% identity to the heavy chain selected from (I); and the light chain comprises an amino acid sequence with at least 90%, at least 95%, at least 96%, at least 97%, at least 98%, at least 99%, or 100% identity to the light chain selected from (II).

In some embodiments, the antibody or antigen-binding fragment thereof comprises:
1) a heavy chain that comprises an amino acid sequence with at least 85% identity to an amino acid sequence of SEQ ID NO: 13, and a light chain that comprises an amino acid sequence with at least 85% identity to an amino acid sequence of SEQ ID NO: 15;
2) a heavy chain that comprises an amino acid sequence with at least 85% identity to an amino acid sequence of SEQ ID NO:27, and a light chain that comprises an amino acid sequence with at least 85% identity to an amino acid sequence of SEQ ID NO: 29;
3) a heavy chain that comprises an amino acid sequence with at least 85% identity to an amino acid sequence of SEQ ID NO: 41, and a light chain that comprises an amino acid sequence with at least 85% identity to an amino acid sequence of SEQ ID NO: 43;
4) a heavy chain that comprises an amino acid sequence with at least 85% identity to an amino acid sequence of SEQ ID NO: 55, and a light chain that comprises an amino acid sequence with at least 85% identity to an amino acid sequence of SEQ ID NO: 57;
5) a heavy chain that comprises an amino acid sequence with at least 85% identity to an amino acid sequence of SEQ ID NO: 64, and a light chain that comprises an amino acid sequence with at least 85% identity to an amino acid sequence of SEQ ID NO: 66;
6) a heavy chain that comprises an amino acid sequence with at least 85% identity to an amino acid sequence of SEQ ID NO: 64, and a light chain that comprises an amino acid sequence with at least 85% identity to an amino acid sequence of SEQ ID NO: 70; and/or
7) a heavy chain that comprises an amino acid sequence with at least 85% identity to an amino acid sequence of SEQ ID NO: 76, and a light chain that comprises an amino acid sequence with at least 85% identity to an amino acid sequence of SEQ ID NO: 78.

In some embodiments, the heavy chain and the light chain comprise an amino acid sequence with at least 90%, at least 95%, at least 96%, at least 97%, at least 98%, at least 99%, or 100% identity to the heavy chain and the light chain selected from 1)-7), respectively.

In another respect, the invention provides an antibody or antigen-binding fragment thereof that comprises a heavy chain variable region (VH) consisting of SEQ ID NO: 3 and a light chain variable region (VL) consisting of SEQ ID NO: 8.

In yet another respect, the invention provides an antibody or antigen-binding fragment thereof that comprises a heavy chain variable region (VH) consisting of SEQ ID NO: 17 and a light chain variable region (VL) consisting of SEQ ID NO: 22.

In still yet another respect, the invention provides an antibody or antigen-binding fragment thereof that comprises a heavy chain variable region (VH) consisting of SEQ ID NO: 31 and a light chain variable region (VL) consisting of SEQ ID NO: 36.

In one respect, the invention provides an antibody or antigen-binding fragment thereof that comprises a heavy chain variable region (VH) consisting of SEQ ID NO: 45 and a light chain variable region (VL) consisting of SEQ ID NO: 50.

In another respect, the invention provides an antibody or antigen-binding fragment thereof that comprises a heavy chain variable region (VH) consisting of SEQ ID NO: 60 and a light chain variable region (VL) consisting of SEQ ID NO: 62.

In yet another respect, the invention provides an antibody or antigen-binding fragment thereof that comprises a heavy chain variable region (VH) consisting of SEQ ID NO: 60 and a light chain variable region (VL) consisting of SEQ ID NO: 68.

In still yet another respect, the invention provides an antibody or antigen-binding fragment thereof, which comprises a heavy chain variable region (VH) consisting of SEQ ID NO: 72 and a light chain variable region (VL) consisting of SEQ ID NO: 74.

In some embodiments, the antibody or antigen-binding fragment thereof is an antagonist of CD39.

In some embodiments, the CD39 is human CD39 or machin CD39.

In some embodiments, the antibody or antigen-binding fragment thereof may reduce the ATP enzyme (ATPase) activity of CD39.

In one respect, the invention provides a nucleic acid composition, which comprises:
(I) a first nucleic acid comprising a nucleotide sequence selected from a group consisting of SEQ ID NOs: 4, 18, 32, 46, 61 and/or 73; and
(II) a second nucleic acid comprising a nucleotide sequence selected from a group consisting of SEQ ID NOs: 9, 23, 37, 51, 63, 69 and/or 75.

In some embodiments, the nucleic acid composition comprises:
1) the first nucleic acid comprising SEQ ID NO: 4 and the second nucleic acid comprising SEQ ID NO: 9;
2) the first nucleic acid comprising SEQ ID NO: 18 and the second nucleic acid comprising SEQ ID NO: 23;

3) the first nucleic acid comprising SEQ ID NO: 32 and the second nucleic acid comprising SEQ ID NO: 37;
4) the first nucleic acid comprising SEQ ID NO: 46 and the second nucleic acid comprising SEQ ID NO: 51;
5) the first nucleic acid comprising SEQ ID NO: 61 and the second nucleic acid comprising SEQ ID NO: 63;
6) the first nucleic acid comprising SEQ ID NO: 61 and the second nucleic acid comprising SEQ ID NO: 69; and/or
7) the first nucleic acid comprising SEQ ID NO: 73 and the second nucleic acid comprising SEQ ID NO: 75.

In another respect, the invention provides an expression vector composition, which comprises:
(I) a first expression vector comprising a nucleotide sequence selected from a group consisting of SEQ ID NOs: 4, 18, 32, 46, 61 and/or 73; and
(II) a second expression vector comprising a nucleotide sequence selected from a group consisting of SEQ ID NO: 9, 23, 37, 51, 63, 69 and/or 75.

In some embodiments, the expression vector composition comprises:
1) a first expression vector comprising a nucleotide sequence of SEQ ID NO: 4 and a second expression vector comprising a nucleotide sequence of SEQ ID NO: 9;
2) a first expression vector comprising a nucleotide sequence of SEQ ID NO: 18 and a second expression vector comprising a nucleotide sequence of SEQ ID NO: 23;
3) a first expression vector comprising a nucleotide sequence of SEQ ID NO: 32 and a second expression vector comprising a nucleotide sequence of SEQ ID NO: 37; or
4) a first expression vector comprising a nucleotide sequence of SEQ ID NO: 46 and a second expression vector comprising a nucleotide sequence of SEQ ID NO: 51;
5) a first expression vector comprising a nucleotide sequence of SEQ ID NO: 61 and a second expression vector comprising a nucleotide sequence of SEQ ID NO: 63;
6) a first expression vector comprising a nucleotide sequence of SEQ ID NO: 61 and a second expression vector comprising a nucleotide sequence of SEQ ID NO: 69; and/or
7) a first expression vector comprising a nucleotide sequence of SEQ ID NO: 73 and a second expression vector comprising a nucleotide sequence of SEQ ID NO: 75.

In yet another respect, the invention provides an expression vector, which comprises:
(I) a first nucleic acid sequence comprising a nucleotide sequence selected from a group consisting of SEQ ID NO: 4, 18, 32, 46, 61 and/or 73; and
(II) a second nucleic acid sequence comprising a nucleotide sequence selected from a group consisting of SEQ ID NO: 9, 23, 37, 51, 63, 69 and/or 75.

In some embodiments, the expression vector comprises:
1) a first nucleic acid sequence comprising a nucleotide sequence of SEQ ID NO: 4 and a second nucleic acid sequence comprising a nucleotide sequence of SEQ ID NO: 9;
2) a first nucleic acid sequence comprising a nucleotide sequence of SEQ ID NO: 18 and a second nucleic acid sequence comprising a nucleotide sequence of SEQ ID NO: 23;
3) a first nucleic acid sequence comprising a nucleotide sequence of SEQ ID NO: 32 and a second nucleic acid sequence comprising a nucleotide sequence of SEQ ID NO: 37;
4) a first nucleic acid sequence comprising a nucleotide sequence of SEQ ID NO: 46 and a second nucleic acid sequence comprising a nucleotide sequence of SEQ ID NO: 51;
5) a first nucleic acid sequence comprising a nucleotide sequence of SEQ ID NO: 61 and a second nucleic acid sequence comprising a nucleotide sequence of SEQ ID NO: 63;
6) a first nucleic acid sequence comprising a nucleotide sequence of SEQ ID NO: 61 and a second nucleic acid sequence comprising a nucleotide sequence of SEQ ID NO: 69; and/or
7) a first nucleic acid sequence comprising a nucleotide sequence of SEQ ID NO: 73 and a second nucleic acid sequence comprising a nucleotide sequence of SEQ ID NO: 75.

In still yet another respect, the invention provides a nucleic acid composition, which comprises:
(I) a first nucleic acid comprising a nucleotide sequence selected from a group consisting of SEQ ID NOs: 14, 28, 42, 56, 65 and/or 77; and
(II) a second nucleic acid comprising a nucleotide sequence selected from a group consisting of SEQ ID NOs: 16, 30, 44, 58, 67, 71 and/or 79.

In some embodiments, the nucleic acid composition comprises:
1) the first nucleic acid comprising a nucleotide sequence of SEQ ID NO: 14 and the second nucleic acid comprising a nucleotide sequence of SEQ ID NO: 16;
2) the first nucleic acid comprising a nucleotide sequence of SEQ ID NO: 28 and the second nucleic acid comprising a nucleotide sequence of SEQ ID NO: 30;
3) the first nucleic acid comprising a nucleotide sequence of SEQ ID NO: 42 and the second nucleic acid comprising a nucleotide sequence of SEQ ID NO: 44;
4) the first nucleic acid comprising a nucleotide sequence of SEQ ID NO: 56 and the second nucleic acid comprising a nucleotide sequence of SEQ ID NO: 58;
5) the first nucleic acid comprising a nucleotide sequence of SEQ ID NO: 65 and the second nucleic acid comprising a nucleotide sequence of SEQ ID NO: 67;
6) the first nucleic acid comprising a nucleotide sequence of SEQ ID NO: 65 and the second nucleic acid comprising a nucleotide sequence of SEQ ID NO: 71; and/or
7) the first nucleic acid comprising a nucleotide sequence of SEQ ID NO: 77 and the second nucleic acid comprising a nucleotide sequence of SEQ ID NO: 79.

In one respect, the invention provides an expression vector composition, which comprises:
(I) a first expression vector comprising a nucleotide sequence selected from a group consisting of SEQ ID NOs: 14, 28, 42, 56, 65 and/or 77; and
(II) a second expression vector comprising a nucleotide sequence selected from a group consisting of SEQ ID NOs: 16, 30, 44, 58, 67, 71 and/or 79.

In some embodiments, the expression vector composition comprises:
1) a first expression vector comprising a nucleotide sequence of SEQ ID NO: 14 and a second expression vector comprising a nucleotide sequence of SEQ ID NO: 16;

2) a first expression vector comprising a nucleotide sequence of SEQ ID NO: 28 and a second expression vector comprising a nucleotide sequence of SEQ ID NO: 30;
3) a first expression vector comprising a nucleotide sequence of SEQ ID NO: 42 and a second expression vector comprising a nucleotide sequence of SEQ ID NO: 44; or
4) a first expression vector comprising a nucleotide sequence of SEQ ID NO: 56 and a second expression vector comprising a nucleotide sequence of SEQ ID NO: 58;
5) a first expression vector comprising a nucleotide sequence of SEQ ID NO: 65 and a second expression vector comprising a nucleotide sequence of SEQ ID NO: 67;
6) a first expression vector comprising a nucleotide sequence of SEQ ID NO: 65 and a second expression vector comprising a nucleotide sequence of SEQ ID NO: 71; and/or
7) a first expression vector comprising a nucleotide sequence of SEQ ID NO: 77 and a second expression vector comprising a nucleotide sequence of SEQ ID NO: 79.

In another respect, the invention provides an expression vector, which comprises:
(I) a first nucleic acid sequence comprising a nucleotide sequence selected from a group consisting of SEQ ID NOs: 14, 28, 42, 56, 65 and/or 77; and
(II) a second nucleic acid sequence comprising a nucleotide sequence selected from a group consisting of SEQ ID NOs: 16, 30, 44, 58, 67, 71 and/or 79.

In some embodiment, the expression vector comprises:
1) a first nucleic acid sequence comprising a nucleotide sequence of SEQ ID NO: 14 and a second nucleic acid sequence comprising a nucleotide sequence of SEQ ID NO: 16;
2) a first nucleic acid sequence comprising a nucleotide sequence of SEQ ID NO: 28 and a second nucleic acid sequence comprising a nucleotide sequence of SEQ ID NO: 30;
3) a first nucleic acid sequence comprising a nucleotide sequence of SEQ ID NO: 42 and a second nucleic acid sequence comprising a nucleotide sequence of SEQ ID NO: 44;
4) a first nucleic acid sequence comprising a nucleotide sequence of SEQ ID NO: 56 and a second nucleic acid sequence comprising a nucleotide sequence of SEQ ID NO: 58;
5) a first nucleic acid sequence comprising a nucleotide sequence of SEQ ID NO: 65 and a second nucleic acid sequence comprising a nucleotide sequence of SEQ ID NO: 67;
6) a first nucleic acid sequence comprising a nucleotide sequence of SEQ ID NO: 65 and a second nucleic acid sequence comprising a nucleotide sequence of SEQ ID NO: 71; and/or
7) a first nucleic acid sequence comprising a nucleotide sequence of SEQ ID NO: 77 and a second nucleic acid sequence comprising a nucleotide sequence of SEQ ID NO:79.

In yet another respect, the invention provides a nucleic acid composition, which comprises:
(I) a first nucleic acid comprising a nucleotide sequence encoding a heavy chain variable region (VH) as represented by an amino acid sequence of SEQ ID NOs: 3, 17, 31, 45, 60 and/or 72; and (II) a second nucleic acid comprising a nucleotide sequence encoding a light chain variable region (VL) as represented by an amino acid sequence of SEQ ID NOs: 8, 22, 36, 50, 62, 68 and/or 74.

In some embodiments, the nucleic acid composition comprises:
1) the first nucleic acid encoding a heavy chain variable region (VH) as represented by an amino acid sequence of SEQ ID NO: 3 and the second nucleic acid encoding a light chain variable region (VL) as represented by an amino acid sequence of SEQ ID NO: 8;
2) the first nucleic acid encoding a heavy chain variable region (VH) as represented by an amino acid sequence of SEQ ID NO: 17 and the second nucleic acid encoding a light chain variable region (VL) as represented by an amino acid sequence of SEQ ID NO: 22;
3) the first nucleic acid encoding a heavy chain variable region (VH) as represented by an amino acid sequence of SEQ ID NO: 31 and the second nucleic acid encoding a light chain variable region (VL) as represented by an amino acid sequence of SEQ ID NO: 36;
4) the first nucleic acid encoding a heavy chain variable region (VH) as represented by an amino acid sequence of SEQ ID NO: 45 and the second nucleic acid encoding a light chain variable region (VL) as represented by an amino acid sequence of SEQ ID NO: 50;
5) the first nucleic acid encoding a heavy chain variable region (VH) as represented by an amino acid sequence of SEQ ID NO: 60 and the second nucleic acid encoding a light chain variable region (VL) as represented by an amino acid sequence of SEQ ID NO: 62;
6) the first nucleic acid encoding a heavy chain variable region (VH) as represented by an amino acid sequence of SEQ ID NO: 60 and the second nucleic acid encoding a light chain variable region (VL) as represented by an amino acid sequence of SEQ ID NO: 68; and/or
7) the first nucleic acid encoding a heavy chain variable region (VH) as represented by an amino acid sequence of SEQ ID NO: 72 and the second nucleic acid encoding a light chain variable region (VL) as represented by an amino acid sequence of SEQ ID NO: 74.

In some embodiments, the nucleic acid composition comprises:
1) the first nucleic acid as represented by SEQ ID NO: 4 which encodes a heavy chain variable region (VH) as represented by an amino acid sequence of SEQ ID NO: 3 and the second nucleic acid as represented by SEQ ID NO: 9 which encodes a light chain variable region (VL) as represented by an amino acid sequence of SEQ ID NO: 8;
2) the first nucleic acid as represented by SEQ ID NO: 18 which encodes a heavy chain variable region (VH) as represented by an amino acid sequence of SEQ ID NO: 17 and the second nucleic acid as represented by SEQ ID NO: 23 which encodes a light chain variable region (VL) as represented by an amino acid sequence of SEQ ID NO: 22;
3) the first nucleic acid as represented by SEQ ID NO: 32 which encodes a heavy chain variable region (VH) as represented by an amino acid sequence of SEQ ID NO: 31 and the second nucleic acid as represented by SEQ ID NO: 37 which encodes a light chain variable region (VL) as represented by an amino acid sequence of SEQ ID NO: 36;
4) the first nucleic acid as represented by SEQ ID NO: 46 which encodes a heavy chain variable region (VH) as represented by an amino acid sequence of SEQ ID NO:

45 and the second nucleic acid as represented by SEQ ID NO: 51 which encodes a light chain variable region (VL) as represented by an amino acid sequence of SEQ ID NO: 50;

5) the first nucleic acid as represented by SEQ ID NO: 61 which encodes a heavy chain variable region (VH) as represented by an amino acid sequence of SEQ ID NO: 60 and the second nucleic acid as represented by SEQ ID NO: 63 which encodes a light chain variable region (VL) as represented by an amino acid sequence of SEQ ID NO: 62;

6) the first nucleic acid as represented by SEQ ID NO: 61 which encodes a heavy chain variable region (VH) as represented by an amino acid sequence of SEQ ID NO: 60 and the second nucleic acid as represented by SEQ ID NO: 69 which encodes a light chain variable region (VL) as represented by an amino acid sequence of SEQ ID NO: 68; and/or 7) the first nucleic acid as represented by SEQ ID NO: 73 which encodes a heavy chain variable region (VH) as represented by an amino acid sequence of SEQ ID NO: 72 and the second nucleic acid as represented by SEQ ID NO: 75 which encodes a light chain variable region (VL) as represented by an amino acid sequence of SEQ ID NO: 74.

In still yet another respect, the invention provides an expression vector composition, which comprises:

(I) a first expression vector comprising a nucleotide sequence encoding a heavy chain variable region (VH) as represented by an amino acid sequence selected from SEQ ID NOs: 3, 17, 31, 45, 60 and/or 72; and (II) a second expression vector comprising a nucleotide sequence encoding a light chain variable region (VL) as represented by an amino acid sequence selected from SEQ ID NOs: 8, 22, 36, 50, 62, 68 and/or 74.

In some embodiments, the expression vector composition comprises:

1) the first expression vector comprising a nucleotide sequence which encodes a heavy chain variable region (VH) as represented by an amino acid sequence of SEQ ID NO: 3 and the second expression vector comprising a nucleotide sequence which encodes a light chain variable region (VL) as represented by an amino acid sequence of SEQ ID NO: 8;

2) the first expression vector comprising a nucleotide sequence which encodes a heavy chain variable region (VH) as represented by an amino acid sequence of SEQ ID NO: 17 and the second expression vector comprising a nucleotide sequence which encodes a light chain variable region (VL) as represented by an amino acid sequence of SEQ ID NO: 22;

3) the first expression vector comprising a nucleotide sequence which encodes a heavy chain variable region (VH) as represented by an amino acid sequence of SEQ ID NO: 31 and the second expression vector comprising a nucleotide sequence which encodes a light chain variable region (VL) as represented by an amino acid sequence of SEQ ID NO: 36;

4) the first expression vector comprising a nucleotide sequence which encodes a heavy chain variable region (VH) as represented by an amino acid sequence of SEQ ID NO: 45 and the second expression vector comprising a nucleotide sequence which encodes a light chain variable region (VL) as represented by an amino acid sequence of SEQ ID NO: 50;

5) the first expression vector comprising a nucleotide sequence which encodes a heavy chain variable region (VH) as represented by an amino acid sequence of SEQ ID NO: 60 and the second expression vector comprising a nucleotide sequence which encodes a light chain variable region (VL) as represented by an amino acid sequence of SEQ ID NO: 62;

6) the first expression vector comprising a nucleotide sequence which encodes a heavy chain variable region (VH) as represented by an amino acid sequence of SEQ ID NO: 60 and the second expression vector comprising a nucleotide sequence which encodes a light chain variable region (VL) as represented by an amino acid sequence of SEQ ID NO: 68; and/or 7) the first expression vector comprising a nucleotide sequence which encodes a heavy chain variable region (VH) as represented by an amino acid sequence of SEQ ID NO: 72 and the second expression vector comprising a nucleotide sequence which encodes a light chain variable region (VL) as represented by an amino acid sequence of SEQ ID NO: 74.

In some embodiment, the expression vector composition comprises:

1) the first expression vector comprising a nucleotide sequence as represented by SEQ ID NO: 4 which encodes a heavy chain variable region (VH) as represented by an amino acid sequence of SEQ ID NO: 3 and the second expression vector comprising a nucleotide sequence as represented by SEQ ID NO: 9 which encodes a light chain variable region (VL) as represented by an amino acid sequence of SEQ ID NO: 8;

2) the first expression vector comprising a nucleotide sequence as represented by SEQ ID NO: 18 which encodes a heavy chain variable region (VH) as represented by an amino acid sequence of SEQ ID NO: 17 and the second expression vector comprising a nucleotide sequence as represented by SEQ ID NO: 23 which encodes a light chain variable region (VL) as represented by an amino acid sequence of SEQ ID NO: 22;

3) the first expression vector comprising a nucleotide sequence as represented by SEQ ID NO: 32 which encodes a heavy chain variable region (VH) as represented by an amino acid sequence of SEQ ID NO: 31 and the second expression vector comprising a nucleotide sequence as represented by SEQ ID NO: 37 which encodes a light chain variable region (VL) as represented by an amino acid sequence of SEQ ID NO: 36;

4) the first expression vector comprising a nucleotide sequence as represented by SEQ ID NO: 46 which encodes a heavy chain variable region (VH) as represented by an amino acid sequence of SEQ ID NO: 45 and the second expression vector comprising a nucleotide sequence as represented by SEQ ID NO: 51 which encodes a light chain variable region (VL) as represented by an amino acid sequence of SEQ ID NO: 50;

5) the first expression vector comprising a nucleotide sequence as represented by SEQ ID NO: 61 which encodes a heavy chain variable region (VH) as represented by an amino acid sequence of SEQ ID NO: 60 and the second expression vector comprising a nucleotide sequence as represented by SEQ ID NO: 63 which encodes a light chain variable region (VL) as represented by an amino acid sequence of SEQ ID NO: 62;

6) the first expression vector comprising a nucleotide sequence as represented by SEQ ID NO: 61 which encodes a heavy chain variable region (VH) as represented by an amino acid sequence of SEQ ID NO: 60 and the second expression vector comprising a nucleotide sequence as represented by SEQ ID NO: 69 which encodes a light chain variable region (VL) as represented by an amino acid sequence of SEQ ID NO: 68; and/or
7) the first expression vector comprising a nucleotide sequence as represented by SEQ ID NO: 73 which encodes a heavy chain variable region (VH) as represented by an amino acid sequence of SEQ ID NO: 72 and the second expression vector comprising a nucleotide sequence as represented by SEQ ID NO: 75 which encodes a light chain variable region (VL) as represented by an amino acid sequence of SEQ ID NO: 74.

In one respect, the invention provides an expression vector, which comprises:
(I) a first nucleic acid sequence comprising a nucleotide sequence encoding a heavy chain variable region (VH) as represented by an amino acid sequence selected from SEQ ID NOs: 3, 17, 31, 45, 60 and/or 72; and
(II) a second nucleic acid sequence comprising a nucleotide sequence encoding a light chain variable region (VL) as represented by an amino acid sequence selected from SEQ ID NOs: 8, 22, 36, 50, 62, 68 and/or 74.

In some embodiment, the expression vector comprises:
1) the first nucleic acid sequence comprising a nucleotide sequence encoding a heavy chain variable region (VH) as represented by an amino acid sequence of SEQ ID NO: 3 and the second nucleic acid sequence comprising a nucleotide sequence encoding a light chain variable region (VL) as represented by an amino acid sequence of SEQ ID NO: 8;
2) the first nucleic acid sequence comprising a nucleotide sequence encoding a heavy chain variable region (VH) as represented by an amino acid sequence of SEQ ID NO: 17 and the second nucleic acid sequence comprising a nucleotide sequence encoding a light chain variable region (VL) as represented by an amino acid sequence of SEQ ID NO: 22;
3) the first nucleic acid sequence comprising a nucleotide sequence encoding a heavy chain variable region (VH) as represented by an amino acid sequence of SEQ ID NO: 31 and the second nucleic acid sequence comprising a nucleotide sequence encoding a light chain variable region (VL) as represented by an amino acid sequence of SEQ ID NO: 36;
4) the first nucleic acid sequence comprising a nucleotide sequence encoding a heavy chain variable region (VH) as represented by an amino acid sequence of SEQ ID NO: 45 and the second nucleic acid sequence comprising a nucleotide sequence encoding a light chain variable region (VL) as represented by an amino acid sequence of SEQ ID NO: 50;
5) the first nucleic acid sequence comprising a nucleotide sequence encoding a heavy chain variable region (VH) as represented by an amino acid sequence of SEQ ID NO: 60 and the second nucleic acid sequence comprising a nucleotide sequence encoding a light chain variable region (VL) as represented by an amino acid sequence of SEQ ID NO: 62;
6) the first nucleic acid sequence comprising a nucleotide sequence encoding a heavy chain variable region (VH) as represented by an amino acid sequence of SEQ ID NO: 60 and the second nucleic acid sequence comprising a nucleotide sequence encoding a light chain variable region (VL) as represented by an amino acid sequence of SEQ ID NO: 68; and/or
7) the first nucleic acid sequence comprising a nucleotide sequence encoding a heavy chain variable region (VH) as represented by an amino acid sequence of SEQ ID NO: 72 and the second nucleic acid sequence comprising a nucleotide sequence encoding a light chain variable region (VL) as represented by an amino acid sequence of SEQ ID NO: 74.

In some embodiments, the expression vector comprises:
1) the first nucleic acid sequence comprising a nucleotide sequence as represented by SEQ ID NO: 4 which encodes a heavy chain variable region (VH) as represented by an amino acid sequence of SEQ ID NO: 3 and the second nucleic acid sequence comprising a nucleotide sequence as represented by SEQ ID NO: 9 which encodes a light chain variable region (VL) as represented by an amino acid sequence of SEQ ID NO: 8;
2) the first nucleic acid sequence comprising a nucleotide sequence as represented by SEQ ID NO: 18 which encodes a heavy chain variable region (VH) as represented by an amino acid sequence of SEQ ID NO: 17 and the second nucleic acid sequence comprising a nucleotide sequence as represented by SEQ ID NO: 23 which encodes a light chain variable region (VL) as represented by an amino acid sequence of SEQ ID NO: 22;
3) the first nucleic acid sequence comprising a nucleotide sequence as represented by SEQ ID NO: 32 which encodes a heavy chain variable region (VH) as represented by an amino acid sequence of SEQ ID NO: 31 and the second nucleic acid sequence comprising a nucleotide sequence as represented by SEQ ID NO: 37 which encodes a light chain variable region (VL) as represented by an amino acid sequence of SEQ ID NO: 36;
4) the first nucleic acid sequence comprising a nucleotide sequence as represented by SEQ ID NO: 46 which encodes a heavy chain variable region (VH) as represented by an amino acid sequence of SEQ ID NO: 45 and the second nucleic acid sequence comprising a nucleotide sequence as represented by SEQ ID NO: 51 which encodes a light chain variable region (VL) as represented by an amino acid sequence of NO: 50;
5) the first nucleic acid sequence comprising a nucleotide sequence as represented by SEQ ID NO: 61 which encodes a heavy chain variable region (VH) as represented by an amino acid sequence of SEQ ID NO: 60 and the second nucleic acid sequence comprising a nucleotide sequence as represented by SEQ ID NO: 63 which encodes a light chain variable region (VL) as represented by an amino acid sequence of SEQ ID NO: 62;
6) the first nucleic acid sequence comprising a nucleotide sequence as represented by SEQ ID NO: 61 which encodes a heavy chain variable region (VH) as represented by an amino acid sequence of SEQ ID NO: 60 and the second nucleic acid sequence comprising a nucleotide sequence as represented by SEQ ID NO: 69 which encodes a light chain variable region (VL) as represented by an amino acid sequence of SEQ ID NO: 68; and/or
7) the first nucleic acid sequence comprising a nucleotide sequence as represented by SEQ ID NO: 73 which encodes a heavy chain variable region (VH) as represented by an amino acid sequence of SEQ ID NO: 72 and the second nucleic acid sequence comprising a nucleotide sequence as represented by SEQ ID NO: 75 which encodes a light chain variable region (VL) as represented by an amino acid sequence of SEQ ID NO: 74.

In another respect, the invention provides a nucleic acid composition that comprises:
(I) a first nucleic acid comprising a nucleotide sequence encoding a heavy chain as represented by an amino acid sequence of SEQ ID NOs: 13, 27, 41, 55, 64 and/or 76; and
(II) a second nucleic acid comprising a nucleotide sequence encoding a light chain as represented by an amino acid sequence of SEQ ID NOs: 15, 29, 43, 57, 66, 70 and/or 78.

In some embodiment, the nucleic acid composition comprises:
1) the first nucleic acid encoding a heavy chain as represented by an amino acid sequence of SEQ ID NO: 13 and the second nucleic acid encoding a light chain as represented by an amino acid sequence of SEQ ID NO: 15;
2) the first nucleic acid encoding a heavy chain as represented by an amino acid sequence of SEQ ID NO: 27 and the second nucleic acid encoding a light chain as represented by an amino acid sequence of SEQ ID NO: 29;
3) the first nucleic acid encoding a heavy chain as represented by an amino acid sequence of SEQ ID NO: 41 and the second nucleic acid encoding a light chain as represented by an amino acid sequence of SEQ ID NO: 43;
4) the first nucleic acid encoding a heavy chain as represented by an amino acid sequence of SEQ ID NO: 55 and the second nucleic acid encoding a light chain as represented by an amino acid sequence of SEQ ID NO: 57;
5) the first nucleic acid encoding a heavy chain as represented by an amino acid sequence of SEQ ID NO: 64 and the second nucleic acid encoding a light chain as represented by an amino acid sequence of SEQ ID NO: 66;
6) the first nucleic acid encoding a heavy chain as represented by an amino acid sequence of SEQ ID NO: 64 and the second nucleic acid encoding a light chain as represented by an amino acid sequence of SEQ ID NO: 70; and/or
7) the first nucleic acid encoding a heavy chain as represented by an amino acid sequence of SEQ ID NO: 76 and the second nucleic acid encoding a light chain as represented by an amino acid sequence of SEQ ID NO: 78.

In some embodiments, the nucleic acid composition comprises:
1) the first nucleic acid as represented by SEQ ID NO: 14 which encodes a heavy chain as represented by an amino acid sequence of SEQ ID NO: 13 and the second nucleic acid as represented by SEQ ID NO: 16 which encodes a light chain as represented by an amino acid sequence of SEQ ID NO: 15;
2) the first nucleic acid as represented by SEQ ID NO: 28 which encodes a heavy chain as represented by an amino acid sequence of SEQ ID NO: 27 and the second nucleic acid as represented by SEQ ID NO: 30 which encodes a light chain as represented by an amino acid sequence of SEQ ID NO: 29;
3) the first nucleic acid as represented by SEQ ID NO: 42 which encodes a heavy chain as represented by an amino acid sequence of SEQ ID NO: 41 and the second nucleic acid as represented by SEQ ID NO: 44 which encodes a light chain as represented by an amino acid sequence of SEQ ID NO: 43;
4) the first nucleic acid as represented by SEQ ID NO: 56 which encodes a heavy chain as represented by an amino acid sequence of SEQ ID NO: 55 and the second nucleic acid as represented by SEQ ID NO: 58 which encodes a light chain as represented by an amino acid sequence of SEQ ID NO: 57;
5) the first nucleic acid as represented by SEQ ID NO: 65 which encodes a heavy chain as represented by an amino acid sequence of SEQ ID NO: 64 and the second nucleic acid as represented by SEQ ID NO: 67 which encodes a light chain as represented by an amino acid sequence of SEQ ID NO: 66;
6) the first nucleic acid as represented by SEQ ID NO: 65 which encodes a heavy chain as represented by an amino acid sequence of SEQ ID NO: 64 and the second nucleic acid as represented by SEQ ID NO: 71 which encodes a light chain as represented by an amino acid sequence of SEQ ID NO: 70; and/or
7) the first nucleic acid as represented by SEQ ID NO: 77 which encodes a heavy chain as represented by an amino acid sequence of SEQ ID NO: 76 and the second nucleic acid as represented by SEQ ID NO: 79 which encodes a light chain as represented by an amino acid sequence of SEQ ID NO: 78.

In yet another respect, the invention provides an expression vector composition, which comprises:
(I) a first expression vector comprising a nucleotide sequence encoding a heavy chain as represented by an amino acid sequence selected from SEQ ID NOs: 13, 27, 41, 55, 64 and/or 76; and
(II) a second expression vector comprising a nucleotide sequence encoding a light chain as represented by an amino acid sequence selected from SEQ ID NOs: 15, 29, 43, 57, 66, 70 and/or 78.

In some embodiments, the expression vector composition comprises:
1) the first expression vector comprising a nucleotide sequence which encodes a heavy chain as represented by an amino acid sequence of SEQ ID NO: 13 and the second expression vector comprising a nucleotide sequence which encodes a light chain as represented by an amino acid sequence of SEQ ID NO: 15;
2) the first expression vector comprising a nucleotide sequence which encodes a heavy chain as represented by an amino acid sequence of SEQ ID NO: 27 and the second expression vector comprising a nucleotide sequence which encodes a light chain as represented by an amino acid sequence of SEQ ID NO: 29;
3) the first expression vector comprising a nucleotide sequence which encodes a heavy chain as represented by an amino acid sequence of SEQ ID NO: 41 and the second expression vector comprising a nucleotide sequence which encodes a light chain as represented by an amino acid sequence of SEQ ID NO: 43;
4) the first expression vector comprising a nucleotide sequence which encodes a heavy chain as represented by an amino acid sequence of SEQ ID NO: 55 and the second expression vector comprising a nucleotide sequence which encodes a light chain as represented by an amino acid sequence of SEQ ID NO: 57;
5) the first expression vector comprising a nucleotide sequence which encodes a heavy chain as represented by an amino acid sequence of SEQ ID NO: 64 and the second expression vector comprising a nucleotide sequence which encodes a light chain as represented by an amino acid sequence of SEQ ID NO: 66;

6) the first expression vector comprising a nucleotide sequence which encodes a heavy chain as represented by an amino acid sequence of SEQ ID NO: 64 and the second expression vector comprising a nucleotide sequence which encodes a light chain as represented by an amino acid sequence of SEQ ID NO: 70; and/or
7) the first expression vector comprising a nucleotide sequence which encodes a heavy chain as represented by an amino acid sequence of SEQ ID NO: 76 and the second expression vector comprising a nucleotide sequence which encodes a light chain as represented by an amino acid sequence of SEQ ID NO: 78.

In some embodiments, the expression vector composition comprises:
1) the first expression vector comprising a nucleotide sequence as represented by SEQ ID NO: 14 which encodes a heavy chain as represented by an amino acid sequence of SEQ ID NO: 13 and the second expression vector comprising a nucleotide sequence as represented by SEQ ID NO: 16 which encodes a light chain as represented by an amino acid sequence of SEQ ID NO: 15;
2) the first expression vector comprising a nucleotide sequence as represented by SEQ ID NO: 28 which encodes a heavy chain as represented by an amino acid sequence of SEQ ID NO: 27 and the second expression vector comprising a nucleotide sequence as represented by SEQ ID NO: 30 which encodes a light chain as represented by an amino acid sequence of SEQ ID NO: 29;
3) the first expression vector comprising a nucleotide sequence as represented by SEQ ID NO: 42 which encodes a heavy chain as represented by an amino acid sequence of SEQ ID NO: 41 and the second expression vector comprising a nucleotide sequence as represented by SEQ ID NO: 44 which encodes a light chain as represented by an amino acid sequence of SEQ ID NO: 43;
4) the first expression vector comprising a nucleotide sequence as represented by SEQ ID NO: 56 which encodes a heavy chain as represented by an amino acid sequence of SEQ ID NO: 55 and the second expression vector comprising a nucleotide sequence as represented by SEQ ID NO: 58 which encodes a light chain as represented by an amino acid sequence of SEQ ID NO: 57;
5) the first expression vector comprising a nucleotide sequence as represented by SEQ ID NO: 65 which encodes a heavy chain as represented by an amino acid sequence of SEQ ID NO: 64 and the second expression vector comprising a nucleotide sequence as represented by SEQ ID NO: 67 which encodes a light chain as represented by an amino acid sequence of SEQ ID NO: 66;
6) the first expression vector comprising a nucleotide sequence as represented by SEQ ID NO: 65 which encodes a heavy chain as represented by an amino acid sequence of SEQ ID NO: 64 and the second expression vector comprising a nucleotide sequence as represented by SEQ ID NO: 71 which encodes a light chain as represented by an amino acid sequence of SEQ ID NO: 70; and/or
7) the first expression vector comprising a nucleotide sequence as represented by SEQ ID NO: 77 which encodes a heavy chain as represented by an amino acid sequence of SEQ ID NO: 76 and the second expression vector comprising a nucleotide sequence as represented by SEQ ID NO: 79 which encodes a light chain as represented by an amino acid sequence of SEQ ID NO: 78.

In still yet another respect, the invention provides an expression vector, which comprises:
(I) a first nucleic acid sequence comprising a nucleotide sequence encoding a heavy chain as represented by an amino acid sequence selected from SEQ ID NOs: 13, 27, 41, 55, 64 and/or 76; and
(II) a second nucleic acid sequence comprising a nucleotide sequence encoding a light chain as represented by an amino acid sequence selected from SEQ ID NOs: 15, 29, 43, 57, 66, 70 and/or 78.

In some embodiment, the expression vector comprises:
1) the first nucleic acid sequence comprising a nucleotide sequence encoding a heavy chain as represented by an amino acid sequence of SEQ ID NO: 13 and the second nucleic acid sequence comprising a nucleotide sequence encoding a light chain as represented by an amino acid sequence of SEQ ID NO: 15;
2) the first nucleic acid sequence comprising a nucleotide sequence encoding a heavy chain as represented by an amino acid sequence of SEQ ID NO: 27 and the second nucleic acid sequence comprising a nucleotide sequence encoding a light chain as represented by an amino acid sequence of SEQ ID NO: 29;
3) the first nucleic acid sequence comprising a nucleotide sequence encoding a heavy chain as represented by an amino acid sequence of SEQ ID NO: 41 and the second nucleic acid sequence comprising a nucleotide sequence encoding a light chain as represented by an amino acid sequence of SEQ ID NO: 43;
4) the first nucleic acid sequence comprising a nucleotide sequence encoding a heavy chain as represented by an amino acid sequence of SEQ ID NO: 55 and the second nucleic acid sequence comprising a nucleotide sequence encoding a light chain as represented by an amino acid sequence of SEQ ID NO: 57;
5) the first nucleic acid sequence comprising a nucleotide sequence encoding a heavy chain as represented by an amino acid sequence of SEQ ID NO: 64 and the second nucleic acid sequence comprising a nucleotide sequence encoding a light chain as represented by an amino acid sequence of SEQ ID NO: 66;
6) the first nucleic acid sequence comprising a nucleotide sequence encoding a heavy chain as represented by an amino acid sequence of SEQ ID NO: 64 and the second nucleic acid sequence comprising a nucleotide sequence encoding a light chain as represented by an amino acid sequence of SEQ ID NO: 70; and/or
7) the first nucleic acid sequence comprising a nucleotide sequence encoding a heavy chain as represented by an amino acid sequence of SEQ ID NO: 76 and the second nucleic acid sequence comprising a nucleotide sequence encoding a light chain as represented by an amino acid sequence of SEQ ID NO: 78.

In some embodiments, the expression vector comprises:
1) the first nucleic acid sequence comprising a nucleotide sequence as represented by SEQ ID NO: 14 which encodes a heavy chain as represented by an amino acid sequence of SEQ ID NO: 13 and the second nucleic acid sequence comprising a nucleotide sequence as represented by SEQ ID NO: 16 which encodes a light chain as represented by an amino acid sequence of SEQ ID NO: 15;
2) the first nucleic acid sequence comprising a nucleotide sequence as represented by SEQ ID NO: 28 which encodes a heavy chain as represented by an amino acid sequence of SEQ ID NO: 27 and the second nucleic acid sequence comprising a nucleotide sequence as represented by SEQ ID NO: 30 which encodes a light chain as represented by an amino acid sequence of SEQ ID NO: 29;

3) the first nucleic acid sequence comprising a nucleotide sequence as represented by SEQ ID NO: 42 which encodes a heavy chain as represented by an amino acid sequence of SEQ ID NO: 41 and the second nucleic acid sequence comprising a nucleotide sequence as represented by SEQ ID NO: 44 which encodes a light chain as represented by an amino acid sequence of SEQ ID NO: 43;

4) the first nucleic acid sequence comprising a nucleotide sequence as represented by SEQ ID NO: 56 which encodes a heavy chain as represented by an amino acid sequence of SEQ ID NO: 55 and the second nucleic acid sequence comprising a nucleotide sequence as represented by SEQ ID NO: 58 which encodes a light chain as represented by an amino acid sequence of SEQ ID NO: 57;

5) the first nucleic acid sequence comprising a nucleotide sequence as represented by SEQ ID NO: 65 which encodes a heavy chain as represented by an amino acid sequence of SEQ ID NO: 64 and the second nucleic acid sequence comprising a nucleotide sequence as represented by SEQ ID NO: 67 which encodes a light chain as represented by an amino acid sequence of SEQ ID NO: 66;

6) the first nucleic acid sequence comprising a nucleotide sequence as represented by SEQ ID NO: 65 which encodes a heavy chain as represented by an amino acid sequence of SEQ ID NO: 64 and the second nucleic acid sequence comprising a nucleotide sequence as represented by SEQ ID NO: 71 which encodes a light chain as represented by an amino acid sequence of SEQ ID NO: 70; and/or 7) the first nucleic acid sequence comprising a nucleotide sequence as represented by SEQ ID NO: 77 which encodes a heavy chain as represented by an amino acid sequence of SEQ ID NO: 76 and the second nucleic acid sequence comprising a nucleotide sequence as represented by SEQ ID NO: 79 which encodes a light chain as represented by an amino acid sequence of SEQ ID NO: 78.

In one respect, the invention provides a cell comprising the expression vector composition or the expression vector.

In another respect, the invention provides a method of preparing the antibody or antigen-binding fragment thereof, comprising expressing the antibody or antigen-binding fragment thereof in the cell and separating the antibody or antigen-binding fragment thereof from the cell.

In yet another respect, the invention provides a pharmaceutical composition comprising the antibody or antigen-binding fragment thereof, and a pharmaceutically acceptable carrier.

In still yet another respect, the invention provides a kit comprising the antibody or antigen-binding fragment thereof. In one respect, the invention provides a bispecific antibody or a multispecific antibody comprising the light chain variable region and the heavy chain variable region.

In another respect, the invention provides a single chain antibody comprising the light chain variable region and the heavy chain variable region.

In yet another respect, the invention provides an antibody-drug conjugate comprising the light chain variable region and the heavy chain variable region.

In still yet another respect, the invention provides a method of treating a disease comprising administering to a subject in need a therapeutically effective amount of the antibody or antigen-binding fragment thereof, the pharmaceutical composition, the bispecific antibody or multispecific antibody, the single chain antibody, and/or the antibody-drug conjugate.

In some embodiment, the disease is cancer.

In some embodiment, the cancer is solid tumor or hematological cancer.

In some embodiment, the solid tumor is selected from multiple myeloma, melanoma, stomach cancer, pancreatic cancer, breast cancer, colon cancer, lung cancer, head and neck cancer, liver cancer, ovarian cancer, bladder cancer, renal cancer, salivary gland carcinoma, esophageal cancer, glioma, glioblastoma, thyroid cancer, thymic cancer, epithelial cancer, lymphoma, T and/or B cell lymphoma, gastrointestinal stromal tumor, soft tissue neoplasm, testicular cancer, endometrial carcinoma, prostate cancer, and/or brain cancer.

In some embodiment, the hematological cancer is leukemia.

In another respect, the invention provides use of the antibody or antigen-binding fragment thereof, the pharmaceutical composition, the bispecific antibody or multispecific antibody, the single chain antibody, and/or the antibody-drug conjugate for the manufacture of a medicament.

In some embodiment, the medicament is used for the treatment of cancer.

In some embodiment, the cancer is solid tumor or hematological cancer.

In some embodiment, the solid tumor is selected from multiple myeloma, melanoma, stomach cancer, pancreatic cancer, breast cancer, colon cancer, lung cancer, head and neck cancer, liver cancer, ovarian cancer, bladder cancer, renal cancer, salivary gland carcinoma, esophageal cancer, glioma, glioblastoma, thyroid cancer, thymic cancer, epithelial cancer, lymphoma, T and/or B cell lymphoma, gastrointestinal stromal tumor, soft tissue neoplasm, testicular cancer, endometrial carcinoma, prostate cancer, and/or brain cancer.

In some embodiment, the hematological cancer is leukemia.

In still another respect, the invention provides the antibody or antigen-binding fragment thereof, the pharmaceutical composition, the bispecific antibody or multispecific antibody, the single chain antibody, and/or the antibody-drug conjugate for use in the treatment of a disease.

In some embodiments, the disease is a cancer.

In some embodiments, the cancer is solid tumor or hematological cancer.

In some embodiments, the solid tumor is selected from multiple myeloma, melanoma, stomach cancer, pancreatic cancer, breast cancer, colon cancer, lung cancer, head and neck cancer, liver cancer, ovarian cancer, bladder cancer, renal cancer, salivary gland carcinoma, esophageal cancer, glioma, glioblastoma, thyroid cancer, thymic cancer, epithelial cancer, lymphoma, T and/or B cell lymphoma, gastrointestinal stromal tumor, soft tissue neoplasm, testicular cancer, endometrial carcinoma, prostate cancer, and/or brain cancer.

In some embodiment, the hematological cancer is leukemia.

In yet another respect, the invention provides a method of treating a disease comprising administering to a subject in need a therapeutically effective amount of the antibody or antigen-binding fragment thereof, the pharmaceutical composition, the bispecific antibody or multispecific antibody, the single chain antibody, and/or the antibody-drug conjugate.

In some embodiments, the disease is a disease related to CD39.

In one respect, the invention provides use of the antibody or antigen-binding fragment thereof, the pharmaceutical composition, the bispecific antibody or multispecific antibody, the single chain antibody, and/or the antibody-drug conjugate for the manufacture of a medicament.

In some embodiment, the medicament is used for the treatment of a disease related to CD39.

In another respect, the invention provides the antibody or antigen-binding fragment thereof, the pharmaceutical composition, the bispecific antibody or multispecific antibody, the single chain antibody, and/or the antibody-drug conjugate for use in the treatment of a disease.

In some embodiments, the disease is a disease related to CD39.

In still another respect, the invention provides a method of increasing T-cell activity in a cancer patient comprising administering to the cancer patient in need a therapeutically effective amount of the antibody or antigen-binding fragment thereof, the pharmaceutical composition, the bispecific antibody or multispecific antibody, the single chain antibody, and/or the antibody-drug conjugate.

In yet another respect, the invention provides a method of attenuating adenosine-mediated suppression of T-cell activity in a cancer patient comprising administering to the cancer patient in need a therapeutically effective amount of the antibody or antigen-binding fragment thereof, the pharmaceutical composition, the bispecific antibody or multispecific antibody, the single chain antibody, and/or the antibody-drug conjugate.

In one respect, the invention provides a method of increasing T cell activity in the tumor microenvironment of a patient comprising administering the cancer patient a therapeutically effective amount of the antibody or antigen-binding fragment thereof, the pharmaceutical composition, the bispecific antibody or multispecific antibody, the single chain antibody, and/or the antibody-drug conjugate.

In another respect, the invention provides a method of treating or preventing a tumor, which comprises:
(1) detecting CD39 polypeptide in a cell in the tumor microenvironment, optionally in a tumor tissue and/or the adjacent tissue, optionally in a tumor cell, and
(2) based on the measurement of cell expression of CD39 polypeptide in the tumor microenvironment, optionally, if the cell expression of CD39 polypeptide in the tumor microenvironment increased compared to the reference level of CD39 polypeptide, administering to a subject in need a therapeutically effective amount of the antibody or antigen-binding fragment thereof, the pharmaceutical composition, the bispecific antibody or multispecific antibody, the single chain antibody, and/or the antibody-drug conjugate.

In some embodiment, detecting CD39 polypeptide in the cell in the tumor microenvironment in step (1) comprises obtaining a biological sample from an individual, contacting the cell with an antibody binding to the CD39 polypeptide, and measuring the expression of CD39 in the cell, wherein the biological sample comprises a tumor tissue and/or the adjacent tissue.

TABLE 1

Description of the sequence listing of the invention

| SEQ ID NO: | Sequence Description | Sequence |
|---|---|---|
| 1. | huCD39 amino acid sequence | TQNKALPENVKYGIVLDAGSSHTSLYIYKWPAEKEND TGVVHQVEECRVKGPGISKFVQKVNEIGIYLTDCMER AREVIPRSQHQETPVYLGATAGMRLLRMESEELADRV LDVVERSLSNYPFDFQGARIITGQEEGAYGWITINYL LGKFSQKTRWFSIVPYETNNQETFGALDLGGASTQVT FVPQNQTIESPDNALQFRLYGKDYNVYTHSFLCYGKD QALWQKLAKDIQVASNEILRDPCFHPGYKKVVNVSDL YKTPCTKRFEMTLPFQQFEIQGIGNYQQCHQSILELF NTSYCPYSQCAFNGIFLPPLQGDFGAFSAFYFVMKFL NLTSEKVSQEKVTEMMKKFCAQPWEEIKTSYAGVKEK YLSEYCFSGTYILSLLLQGYHFTADSWEHIHFIGKIQ GSDAGWTLGYMLNLTNMIPAEQPLSTPLSHSTYVAHH HHHHHHHH |
| 2. | cynoCD39 amino acid sequence | MLFDSILSTVGLSKLVSVVSSPAAALSKSNVKTFCSK NILAILGFSSIIAVIALLAVGLTQNKALPENIKYGIV LDAGSSHTSLYIYKWPAEKENDTGVVHQVEECRVKGP GISKYVQKVNEIGIYLTDCMERAREVIPRSQHQETPV YLGATAGMRLLRMESEELADRVLDVVERSLSNYPFDF QGARIITGQEEGAYGWITINYLLGKFSQKTRWFSIVP YETNNQETFGALDLGGASTQITFVPQNQTTESPDNAL QFRLYGKDYNVYTHSFLCYGKDQALWQKLAKDIQVAS NEILRDPCFHPGYKKVVNVSDLYKTPCTKRFEMTLPF QQFEIQGIGNYQQCHQSVLELFNTSYCPYSQCAFNGI FLPPLQGDFGAFSAFYFVMNFLNLTSEKVSQEKVTEM MKKFCSQPWEEIKTSYAGVKEKYLSEYCFSGTYILSL LLQGYHFTADSWEHIHFIGKIQGSDAGWTLGYMLNLT NMIPAEQPLSTPLSHSTYVFLMVLFSLVLVIVAIIGL LIFHKPSYFWKDMV |
| 3. | 201 hIgG2 VH amino acid sequence | EVQLVESGGGLVKPGGSLKLSCAASGFTFSDYGMHWV RQAPEKGLEWVAYISSGSSIMYYADTVKGRFTISRDN AKNTLFLQMASLRSEDTAMYYCARDLYYDHVLDYWGQ GTTLTVSS |

TABLE 1-continued

Description of the sequence listing of the invention

| SEQ ID NO: | Sequence Description | Sequence |
|---|---|---|
| 4. | 201 hIgG2 VH nucleotide sequence | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGTGGCAGTAGTATCATGTACTATGCAGA CACAGTGAAGGGCCGATTCACCATCTCCAGAGACAAT GCCAAGAACACCCTGTTCCTGCAAATGGCCAGTCTGA GGTCTGAGGACACGGCCATGTATTATTGTGCAAGGGA CCTCTACTATGATCACGTCCTTGACTACTGGGGCCAA GGCACCACTCTCACAGTCTCCTCA |
| 5. | 201 hIgG2, h201H3.1 + h219L1.1 G2C, h201H3.1 + h201L1.1dmut G2C or M201 HuH1L1(D-E) G2C VH HCDR1 amino acid sequence | DYGMH |
| 6. | 201 hIgG2, h201H3.1 + h219L1.1 G2C, h201H3.1 + h201L1.1dmut G2C or M201 HuH1L1(D-E) G2C VH HCDR2 amino acid sequence | YISSGSSIMYYADTVKG |
| 7. | 201 hIgG2, h201H3.1 + h219L1.1 G2C, h201H3.1 + h201L1.1dmut G2C or M201 HuH1L1(D-E) G2C VH HCDR3 amino acid sequence | DLYYDHVLDY |
| 8. | 201 hIgG2 VL amino acid sequence | DIQMTQSPSSLSASLGERVSLTCRASQEIRGYLIWLQ QKPGGTIKRLIYAASTLDSGVPKRFSGSRSGSDYSLT ISSLESEDFADYYCLQYTSYPRTFGGGTKLEIK |
| 9. | 201 hIgG2 VL nucleotide sequence | GACATCCAGATGACCCAGTCTCCATCCTCCTTATCTG CCTCTCTGGGAGAAAGAGTCAGTCTCACTTGTCGGGC AAGTCAGGAAATTCGTGGTTACTTAATTTGGCTTCAG CAGAAACCAGGTGGAACTATTAAACGCCTGATCTACG CCGCATCCACTTTAGATTCTGGTGTCCCAAAGAGGTT CAGTGGCAGTAGGTCTGGGTCAGATTATTCTCTCACC ATCAGCAGCCTTGAGTCTGAAGATTTTGCAGACTATT ACTGTCTACAATATACTAGTTATCCTCGGACGTTCGG TGGAGGCACCAAGCTGGAAATCAAA |
| 10. | 201 hIgG2, h201H3.1 + h201L1.1dmut G2C orM201 HuH1L1(D-E) G2C VL LCDR1 amino acid sequence | RASQEIRGYLI |

TABLE 1-continued

Description of the sequence listing of the invention

| SEQ ID NO: | Sequence Description | Sequence |
|---|---|---|
| 11. | 201 hIgG2 VL LCDR2 amino acid sequence | AASTLDS |
| 12. | 201 hIgG2, h201H3.1 + h201L1.1dmut G2C or M201 HuH1L1(D-E) G2C VL LCDR3 amino acid sequence | LQYTSYPRT |
| 13. | 201 hIgG2 full length amino acid sequence of heavy chain | EVQLVESGGGLVKPGGSLKLSCAASGFTFSDYGMHWV RQAPEKGLEWVAYISSGSSIMYYADTVKGRFTISRDN AKNTLFLQMASLRSEDTAMYYCARDLYYDHVLDYWGQ GTTLTVSSASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |
| 14. | 201 hIgG2 full length nucleotide sequence of heavy chain | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGTGGCAGTAGTATCATGTACTATGCAGA CACAGTGAAGGGCCGATTCACCATCTCCAGAGACAAT GCCAAGAACACCCTGTTCCTGCAAATGGCCAGTCTGA GGTCTGAGGACACGGCCATGTATTATTGTGCAAGGGA CCTCTACTATGATCACGTCCTTGACTACTGGGGCCAA GGCACCACTCTCACAGTCTCCTCAGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC AGGATTGGCTGAACGGCAAGGAGTACAAGTGCAAGGT GTCCAACAAGGGCCTGCCAGCTCCTATCGAGAAGACC ATCTCCAAGACCAAGGGCCAGCCCAGAGAGCCTCAGG TGTACACACTGCCTCCTTCCCGGGAGGAGATGACCAA GAACCAGGTGTCCCTGACTTGCCTCGTGAAGGGATTC TACCCCTCCGACATCGCAGTCGAGTGGGAATCCAACG GCCAGCCCGAGAACAACTACAAGACCACCCCTCCTAT GCTGGACTCCGACGGCTCCTTCTTCCTGTACTCCAAG CTGACCGTGGACAAGTCCCGTTGGCAGCAGGGCAACG TGTTCTCTTGCAGCGTGATGCACGAGGCCCTGCACAA CCACTACACCCAGAAGAGCCTGTCCCTGTCTCCCGGC AAG |
| 15. | 201 hIgG2 full length amino acid sequence of light chain | DIQMTQSPSSLSASLGERVSLTCRASQEIRGYLIWLQ QKPGGTIKRLIYAASTLDSGVPKRFSGSRSGSDYSLT ISSLESEDFADYYCLQYTSYPRTFGGGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |

TABLE 1-continued

Description of the sequence listing of the invention

| SEQ ID NO: | Sequence Description | Sequence |
|---|---|---|
| 16. | 201 hIgG2 full length nucleotide sequence of light chain | GACATCCAGATGACCCAGTCTCCATCCTCCTTATCTG CCTCTCTGGGAGAAAGAGTCAGTCTCACTTGTCGGGC AAGTCAGGAAATTCGTGGTTACTTAATTTGGCTTCAG CAGAAACCAGGTGGAACTATTAAACGCCTGATCTACG CCGCATCCACTTTAGATTCTGGTGTCCCAAAGAGGTT CAGTGGCAGTAGGTCTGGGTCAGATTATTCTCTCACC ATCAGCAGCCTTGAGTCTGAAGATTTTGCAGACTATT ACTGTCTACAATATACTAGTTATCCTCGGACGTTCGG TGGAGGCACCAAGCTGGAAATCAAAAGAACCGTGGCC GCTCCTTCCGTGTTCATCTTCCCTCCCTCCGACGAGC AGCTGAAGAGCGGAACAGCCTCTGTCGTGTGCCTCCT GAACAACTTCTACCCCCGGGAGGCCAAGGTCCAGTGG AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |
| 17. | 216 hIgG2 VH amino acid sequence | EVQLVESGGGLVKPGGSLKLPCAASGFTFSDYGMHWV RQAPEKGLEWVAYISSGSSIIYYADTVKGRFTISRDN AKNTLFLQMTSLRSEDTAMYYCARDLYYDHVLDYWGQ GTTLTVAS |
| 18. | 216 hIgG2 VH nucleotide sequence | GAGGTGCAGCTGGTGGAGTCTGGGGGAGGCTTAGTGA AGCCTGGAGGGTCCCTGAAACTCCCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGTGGCAGTAGTATCATCTACTATGCAGA CACAGTGAAGGGCCGATTCACCATCTCCAGAGACAAT GCCAAGAACACCCTGTTCCTGCAAATGACCAGTCTGA GGTCTGAGGACACGGCCATGTATTACTGTGCAAGGGA CCTCTACTATGATCACGTCCTTGACTATTGGGGCCAA GGCACCACTCTCACAGTCGCCTCA |
| 19. | 216 hIgG2 VH HCDR1 amino acid sequence | DYGMH |
| 20. | 216 hIgG2 VH HCDR2 amino acid sequence | YISSGSSIIYYADTVKG |
| 21. | 216 hIgG2 VH HCDR3 amino acid sequence | DLYYDHVLDY |
| 22. | 216 hIgG2 VL amino acid sequence | DIQMTQSPSSLSASLGERVSLTCRASQEISGYLIWLQ QKPDGTIKRLIYAASTLDSGVPKRFSGNRSGSDYSLT ISSLESEDFADYYCLQYASYPRTFGGGTKLEIK |
| 23. | 216 hIgG2 VL nucleotide sequence | GACATCCAGATGACCCAGTCTCCATCCTCCTTATCTG CCTCTCTGGGAGAAAGAGTCAGTCTCACTTGTCGGGC AAGTCAGGAAATTAGTGGTTACTTAATCTGGCTTCAG CAGAAACCAGATGGAACTATTAAACGCCTGATCTACG CCGCATCCACTTTAGATTCTGGTGTCCCAAAAAGGTT CAGTGGCAATAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGCACCAAGCTGGAAATCAAA |
| 24. | 216 hIgG2 VL LCDR1 amino acid sequence | RASQEISGYLI |
| 25. | 216 hIgG2 VL LCDR2 amino acid sequence | AASTLDS |

TABLE 1-continued

Description of the sequence listing of the invention

| SEQ ID NO: | Sequence Description | Sequence |
|---|---|---|
| 26. | 216 hIgG2 VL LCDR3 amino acid sequence | LQYASYPRT |
| 27. | 216 hIgG2 full length amino acid sequence of heavy chain | EVQLVESGGGLVKPGGSLKLPCAASGFTFSDYGMHWV RQAPEKGLEWVAYISSGSSIIYYADTVKGRFTISRDN AKNTLFLQMTSLRSEDTAMYYCARDLYYDHVLDYWGQ GTTLTVASASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |
| 28. | 216 hIgG2 full length nucleotide sequence of heavy chain | GAGGTGCAGCTGGTGGAGTCTGGGGGAGGCTTAGTGA AGCCTGGAGGGTCCCTGAAACTCCCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGTGGCAGTAGTATCATCTACTATGCAGA CACAGTGAAGGGCCGATTCACCATCTCCAGAGACAAT GCCAAGAACACCCTGTTCCTGCAAATGACCAGTCTGA GGTCTGAGGACACGGCCATGTATTACTGTGCAAGGGA CCTCTACTATGATCACGTCCTTGACTATTGGGGCCAA GGCACCACTCTCACAGTCGCCTCAGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC AGGATTGGCTGAACGGCAAGGAGTACAAGTGCAAGGT GTCCAACAAGGGCCTGCCAGCTCCTATCGAGAAGACC ATCTCCAAGACCAAGGGCCAGCCCAGAGAGCCTCAGG TGTACACACTGCCTCCTTCCCGGGAGGAGATGACCAA GAACCAGGTGTCCCTGACTTGCCTCGTGAAGGGATTC TACCCCTCCGACATCGCAGTCGAGTGGGAATCCAACG GCCAGCCCGAGAACAACTACAAGACCACCCCTCCTAT GCTGGACTCCGACGGCTCCTTCTTCCTGTACTCCAAG CTGACCGTGGACAAGTCCCGTTGGCAGCAGGGCAACG TGTTCTCTTGCAGCGTGATGCACGAGGCCCTGCACAA CCACTACACCCAGAAGAGCCTGTCCCTGTCTCCCGGC AAG |
| 29. | 216 hIgG2 full length amino acid sequence of light chain | DIQMTQSPSSLSASLGERVSLTCRASQEISGYLIWLQ QKPDGTIKRLIYAASTLDSGVPKRFSGNRSGSDYSLT ISSLESEDFADYYCLQYASYPRTFGGGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 30. | 216 hIgG2 full length nucleotide sequence of light chain | GACATCCAGATGACCCAGTCTCCATCCTCCTTATCTG CCTCTCTGGGAGAAAGAGTCAGTCTCACTTGTCGGGC AAGTCAGGAAATTAGTGGTTACTTAATCTGGCTTCAG CAGAAACCAGATGGAACTATTAAACGCCTGATCTACG CCGCATCCACTTTAGATTCTGGTGTCCCAAAAAGGTT CAGTGGCAATAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGCACCAAGCTGGAAATCAAAAGAACCGTGGCC GCTCCTTCCGTGTTCATCTTCCCTCCCTCCGACGAGC |

TABLE 1-continued

Description of the sequence listing of the invention

| SEQ ID NO: | Sequence Description | Sequence |
|---|---|---|
| | | AGCTGAAGAGCGGAACAGCCTCTGTCGTGTGCCTCCT GAACAACTTCTACCCCGGGAGGCCAAGGTCCAGTGG AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |
| 31. | 217 hIgG2 VH amino acid sequence | EVQLVESGGGLVKPGGSLKLSCAASGFTFSDYGMHWV RQAPEKGLEWVAYISSGSSVIYYVDTVKGRFTISRDN AKNTLFLQMTSLRSEDTAMYYCARDLYYDHVLDSWGQ GTTLTVSS |
| 32. | 217 hIgG2 VH nucleotide sequence | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGCGGCAGTAGTGTCATCTACTATGTAGA CACAGTGAAGGGCCGATTCACCATCTCCAGAGACAAT GCCAAGAACACCCTGTTCCTGCAAATGACCAGTCTGA GGTCTGAGGACACGGCCATGTATTACTGTGCAAGGGA CCTCTACTATGATCACGTCCTTGACTCCTGGGGCCAA GGCACCACTCTCACAGTCTCCTCA |
| 33. | 217 hIgG2 VH HCDR1 amino acid sequence | DYGMH |
| 34. | 217 hIgG2 VH HCDR2 amino acid sequence | YISSGSSVIYYVDTVKG |
| 35. | 217 hIgG2 VH HCDR3 amino acid sequence | DLYYDHVLDS |
| 36. | 217 hIgG2 VL amino acid sequence | DIQMTQSPSSLSASLGERVSLTCRASQEIGGYLSWLQ QKPDGTIKRLIYAASTLDSGVPKRFSGSRSGSDYSLT ISSLESEDFADYYCLQYASYPRTFGGGTKLEIK |
| 37. | 217 hIgG2 VL nucleotide sequence | GACATCCAGATGACCCAGTCTCCATCCTCCTTATCTG CCTCTCTGGGAGAAAGAGTCAGTCTCACTTGTCGGGC AAGTCAGGAAATTGGTGGTTACTTAAGCTGGCTTCAG CAGAAACCAGATGGAACTATTAAACGCCTGATCTACG CCGCATCCACTTTAGATTCTGGTGTCCCAAAAAGGTT CAGTGGCAGTAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGCACCAAGCTGGAAATCAAA |
| 38. | 217 hIgG2 VL LCDR1 amino acid sequence | RASQEIGGYLS |
| 39. | 217 hIgG2 VL LCDR2 amino acid sequence | AASTLDS |
| 40. | 217 VL HCDR3 amino acid sequence | LQYASYPRT |
| 41. | 217 hIgG2 full length amino acid sequence of heavy chain | EVQLVESGGGLVKPGGSLKLSCAASGFTFSDYGMHWV RQAPEKGLEWVAYISSGSSVIYYVDTVKGRFTISRDN AKNTLFLQMTSLRSEDTAMYYCARDLYYDHVLDSWGQ GTTLTVSSASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC |

TABLE 1-continued

Description of the sequence listing of the invention

| SEQ ID NO: | Sequence Description | Sequence |
|---|---|---|
| | | VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |
| 42. | 217 hIgG2 full length nucleotide sequence of heavy chain | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCACTGGGTT CGTCAGGCTCCAGAGAAGGGGCTGGAGTGGGTTGCAT ACATTAGTAGCGGCAGTAGTGTCATCTACTATGTAGA CACAGTGAAGGGCCGATTCACCATCTCCAGAGACAAT GCCAAGAACACCCTGTTCCTGCAAATGACCAGTCTGA GGTCTGAGGACACGGCCATGTATTACTGTGCAAGGGA CCTCTACTATGATCACGTCCTTGACTCCTGGGGCCAA GGCACCACTCTCACAGTCTCCTCAGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC AGGATTGGCTGAACGGCAAGGAGTACAAGTGCAAGGT GTCCAACAAGGGCCTGCCAGCTCCTATCGAGAAGACC ATCTCCAAGACCAAGGGCCAGCCCAGAGAGCCTCAGG TGTACACACTGCCTCCTTCCCGGGAGGAGATGACCAA GAACCAGGTGTCCCTGACTTGCCTCGTGAAGGGATTC TACCCCTCCGACATCGCAGTCGAGTGGGAATCCAACG GCCAGCCCGAGAACAACTACAAGACCACCCCTCCTAT GCTGGACTCCGACGGCTCCTTCTTCCTGTACTCCAAG CTGACCGTGGACAAGTCCCGTTGGCAGCAGGGCAACG TGTTCTCTTGCAGCGTGATGCACGAGGCCCTGCACAA CCACTACACCCAGAAGAGCCTGTCCCTGTCTCCCGGC AAG |
| 43. | 217 hIgG2 full length amino acid sequence of light chain | DIQMTQSPSSLSASLGERVSLTCRASQEIGGYLSWLQ QKPDGTIKRLIYAASTLDSGVPKRFSGSRSGSDYSLT ISSLESEDFADYYCLQYASYPRTFGGGTKLEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 44. | 217 hIgG2 full length nucleotide sequence of light chain | GACATCCAGATGACCCAGTCTCCATCCTCCTTATCTG CCTCTCTGGGAGAAAGAGTCAGTCTCACTTGTCGGGC AAGTCAGGAAATTGGTGGTTACTTAAGCTGGCTTCAG CAGAAACCAGATGGAACTATTAAACGCCTGATCTACG CCGCATCCACTTTAGATTCTGGTGTCCCAAAAAGGTT CAGTGGCAGTAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGCACCAAGCTGGAAATCAAAAGAACCGTGGCC GCTCCTTCCGTGTTCATCTTCCCTCCCTCCGACGAGC AGCTGAAGAGCGGAACAGCCTCTGTCGTGTGCCTCCT GAACAACTTCTACCCCCGGGAGGCCAAGGTCCAGTGG AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |
| 45. | 219 hIgG2 VH amino acid sequence | EVQLVESGGGLVKPGGSLKLSCAASGFTFSDYGMHWV RQAPEKGLEWVAYISSGSSIRYYADTVKGRFTISRDN AKNTLFLQMTSLRSEDTAIYYCARDLYYDHVLDYWGQ GTTLTVSS |

TABLE 1-continued

Description of the sequence listing of the invention

| SEQ ID NO: | Sequence Description | Sequence |
|---|---|---|
| 46. | 219 hIgG2 VH nucleotide sequence | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCATTGGGTT CGTCAGGCTCCAGAGAAGGGGCTGGAGTGGGTTGCAT ACATTAGTAGTGGCAGTAGTATCCGCTACTATGCAGA CACAGTGAAGGGCCGATTCACCATCTCCAGAGACAAT GCCAAGAACACCCTGTTCCTGCAAATGACCAGTCTGC GGTCTGAGGACACGGCCATATATTACTGTGCAAGGGA CCTCTACTATGATCACGTCCTTGACTACTGGGGCCAA GGCACCACTCTCACAGTCTCCTCA |
| 47. | 219 hIgG2 VH HCDR1 amino acid sequence | DYGMH |
| 48. | 219 hIgG2 VH HCDR2 amino acid sequence | YISSGSSIRYYADTVKG |
| 49. | 219 hIgG2 VH HCDR3 amino acid sequence | DLYYDHVLDY |
| 50. | 219 hIgG2 VL amino acid sequence | DIQMTQSPSSLSASLGERVSLTCRASQEVSGYLNWLQ QKPDGTIKRLIYAASTLDSGVPKRFSGSRSGSDYSLT ISSLESEDFADYYCLQYASYPRTFGGGTKVEIK |
| 51. | 219 hIgG2 VL nucleotide sequence | GACATCCAGATGACCCAGTCTCCATCCTCCTTATCTG CCTCTCTGGGAGAAAGAGTCAGTCTCACTTGTCGGGC AAGTCAGGAAGTTAGTGGTTACTTAAACTGGCTTCAG CAGAAGCCAGATGGAACTATTAAACGCCTGATCTACG CCGCATCCACTTTAGATTCTGGTGTCCCAAAGAGGTT CAGTGGCAGTAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGTACCAAGGTGGAAATCAAG |
| 52. | 219 hIgG2 or h201H3.1 + h219L1.1 G2C VL LCDR1 amino acid sequence | RASQEVSGYLN |
| 53. | 219 hIgG2 VL LCDR2 amino acid sequence | AASTLDS |
| 54. | 219 hIgG2 or h201H3.1 + h219L1.1 G2C VL LCDR3 amino acid sequence | LQYASYPRT |
| 55. | 219 hIgG2 full length amino acid sequence of heavy chain | EVQLVESGGGLVKPGGSLKLSCAASGFTFSDYGMHWV RQAPEKGLEWVAYISSGSSIRYYADTVKGRFTISRDN AKNTLFLQMTSLRSEDTAIYYCARDLYYDHVLDYWGQ GTTLTVSSASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |

TABLE 1-continued

Description of the sequence listing of the invention

| SEQ ID NO: | Sequence Description | Sequence |
|---|---|---|
| 56. | 219 hIgG2 full length nucleotide sequence of heavy chain | GAGGTGCAGCTGGTGGAGTCTGGGGGAGGCTTAGTGA AGCCTGGAGGGTCCCTGAAACTCTCCTGTGCAGCCTC TGGATTCACTTTCAGTGACTATGGAATGCATTGGGTT CGTCAGGCTCCAGAGAAGGGGCTGGAGTGGGTTGCAT ACATTAGTAGTGGCAGTAGTATCCGCTACTATGCAGA CACAGTGAAGGGCCGATTCACCATCTCCAGAGACAAT GCCAAGAACACCCTGTTCCTGCAAATGACCAGTCTGC GGTCTGAGGACACGGCCATATATTACTGTGCAAGGGA CCTCTACTATGATCACGTCCTTGACTACTGGGGCCAA GGCACCACTCTCACAGTCTCCTCAGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC AGGATTGGCTGAACGGCAAGGAGTACAAGTGCAAGGT GTCCAACAAGGGCCTGCCAGCTCCTATCGAGAAGACC ATCTCCAAGACCAAGGGCCAGCCCAGAGAGCCTCAGG TGTACACACTGCCTCCTTCCCGGGAGGAGATGACCAA GAACCAGGTGTCCCTGACTTGCCTCGTGAAGGGATTC TACCCCTCCGACATCGCAGTCGAGTGGGAATCCAACG GCCAGCCCGAGAACAACTACAAGACCACCCCTCCTAT GCTGGACTCCGACGGCTCCTTCTTCCTGTACTCCAAG CTGACCGTGGACAAGTCCCGTTGGCAGCAGGGCAACG TGTTCTCTTGCAGCGTGATGCACGAGGCCCTGCACAA CCACTACACCCAGAAGAGCCTGTCCCTGTCTCCCGGC AAG |
| 57. | 219 hIgG2 full length amino acid sequence of light chain | DIQMTQSPSSLSASLGERVSLTCRASQEVSGYLNWLQ QKPDGTIKRLIYAASTLDSGVPKRFSGSRSGSDYSLT ISSLESEDFADYYCLQYASYPRTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 58. | 219 hIgG2 full length nucleotide sequence of light chain | GACATCCAGATGACCCAGTCTCCATCCTCCTTATCTG CCTCTCTGGGAGAAAGAGTCAGTCTCACTTGTCGGGC AAGTCAGGAAGTTAGTGGTTACTTAAACTGGCTTCAG CAGAAGCCAGATGGAACTATTAAACGCCTGATCTACG CCGCATCCACTTTAGATTCTGGTGTCCCAAAGAGGTT CAGTGGCAGTAGGTCTGGGTCAGATTATTCTCTCACC ATCAGCAGCCTTGAGTCTGAAGATTTTGCAGACTATT ACTGTCTACAATATGCTAGTTATCCTCGGACGTTCGG TGGAGGtACCAAGgTGGAAATcAAgAGAACCGTGGCC CGCTCTTCCGTGTTCATCTTCCCTCCCTCCGACGAGC AGCTGAAGAGCGGAACAGCCTCTGTCGTGTGCCTCCT GAACAACTTCTACCCCCGGGAGGCCAAGGTCCAGTGG AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |
| 59. | h201H3.1 + h219L1.1 G2C h201H3.1 + h201L1.1dmut G2C or M201 HuH1L1(D-E) G2C VL LCDR2 amino acid sequence | AASTLES |

TABLE 1-continued

Description of the sequence listing of the invention

| SEQ ID NO: | Sequence Description | Sequence |
|---|---|---|
| 60. | h201H3.1 + h219L1.1 G2C or h201H3.1 + h201L1.1dmut G2C VH amino acid sequence | QVQLVESGGGVVQPGRSLRLSCAASGFTFSDYGMHWV RQAPGKGLEWVAYISSGSSIMYYADTVKGRFTISRDN SKNTLYLQMNSLRAEDTAVYYCARDLYYDHVLDYWGQ GTTVTVSS |
| 61. | h201H3.1 + h219L1.1 G2C VH or h201H3.1 + h201L1.1dmut G2C VH nucleotide sequence | CAAGTGCAGCTCGTCGAAAGCGGAGGAGGCGTGGTGC AGCCCGGAAGGTCTCTGAGACTGAGCTGTGCTGCCAG CGGCTTCACTTTCAGCGACTACGGCATGCACTGGGTC AGACAAGCCCCCGGCAAGGGACTGGAATGGGTCGCTt acATCAGCTCCGGCAGCAGCATCATGTACTACGCCGA CacaGTGAAGGGAAGGTTCACAATCTCTAGGGACAAC AGCAAGAACACACTCTATCTGCAGATGAACTCCCTCA GAGCCGAGGATACAGCTGTGTACTACTGCGCTAGGGA TCTGTACTACGACCACGTGCTCGATTACTGGGGCCAA GGCACAACAGTGACAGTGAGCAGC |
| 62. | h201H3.1 + h219L1.1 G2C VL amino acid sequence | DIQMTQSPSSLSASVGDRVTITCRASQEVSGYLNWLQ QKPGKAIKRLIYAASTLESGVPSRFSGSRSGSDYTLT ISSLQPEDFATYYCLQYASYPRTFGQGTKVEIK |
| 63. | h201H3.1 + h219L1.1 G2C VL nucleotide sequence | GACATCCAGATGACTCAGAGCCCAAGCTCTCTGAGCG CCAGCGTGGGAGATAGGGTCACAATCACTTGTAGGGC CAGCCAAGAGGTGAGCGGCTATCTGAATTGGCTCCAG CAGAAACCCGGCAAGGCCATCAAGAGACTGATCTATG CCGCCAGCaCTCTGgAGTCCGGAGTGCCATCTAGGTT CAGCGGCAGCAGAAGCGGCAGCGACTACACTCTCACA ATCAGCTCCCTCCAGCCAGAAGACTTCGCCACTTACT ACTGTCTGCAGTATGCCAGCTACCCAAGGACTTTCGG ACAGGGTACCAAGGTGGAGATCAAA |
| 64. | h201H3.1 + h219L1.1 G2C or h201H3.1 + h201L1.1dmut G2C full length amino acid sequence of heavy chain | QVQLVESGGGVVQPGRSLRLSCAASGFTFSDYGMHWV RQAPGKGLEWVAYISSGSSIMYYADTVKGRFTISRDN SKNTLYLQMNSLRAEDTAVYYCARDLYYDHVLDYWGQ GTTVTVSSASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |
| 65. | h201H3.1 + h219L1.1 G2C or h201H3.1 + h201L1.1dmut G2C full length nucleotide sequence of heavy chain | CAAGTGCAGCTCGTCGAAAGCGGAGGAGGCGTGGTGC AGCCCGGAAGGTCTCTGAGACTGAGCTGTGCTGCCAG CGGCTTCACTTTCAGCGACTACGGCATGCACTGGGTC AGACAAGCCCCCGGCAAGGGACTGGAATGGGTCGCTT ACATCAGCTCCGGCAGCAGCATCATGTACTACGCCGA CACAGTGAAGGGAAGGTTCACAATCTCTAGGGACAAC AGCAAGAACACACTCTATCTGCAGATGAACTCCCTCA GAGCCGAGGATACAGCTGTGTACTACTGCGCTAGGGA TCTGTACTACGACCACGTGCTCGATTACTGGGGCCAA GGCACAACAGTGACAGTGAGCAGCGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC |

TABLE 1-continued

Description of the sequence listing of the invention

| SEQ ID NO: | Sequence Description | Sequence |
|---|---|---|
| | | AGGATTGGCTGAACGGCAAGGAGTACAAGTGCAAGGT
GTCCAACAAGGGCCTGCCAGCTCCTATCGAGAAGACC
ATCTCCAAGACCAAGGGCCAGCCCAGAGAGCCTCAGG
TGTACACACTGCCTCCTTCCCGGGAGGAGATGACCAA
GAACCAGGTGTCCCTGACTTGCCTCGTGAAGGGATTC
TACCCCTCCGACATCGCAGTCGAGTGGGAATCCAACG
GCCAGCCCGAGAACAACTACAAGACCACCCCTCCTAT
GCTGGACTCCGACGGCTCCTTCTTCCTGTACTCCAAG
CTGACCGTGGACAAGTCCCGTTGGCAGCAGGGCAACG
TGTTCTCTTGCAGCGTGATGCACGAGGCCCTGCACAA
CCACTACACCCAGAAGAGCCTGTCCCTGTCTCCCGGC
AAG |
| 66. | h201H3.1 + 1h29L1.1 G2C full length amino acid sequence of light chain | DIQMTQSPSSLSASVGDRVTITCRASQEVSGYLNWLQ
QKPGKAIKRLIYAASTLESGVPSRFSGSRSGSDYTLT
ISSLQPEDFATYYCLQYASYPRTFGQGTKVEIKRTVA
APSVFIFPPSDEQLKSGTASVVCLLNNFYPREAKVQW
KVDNALQSGNSQESVTEQDSKDSTYSLSSTLTLSKAD
YEKHKVYACEVTHQGLSSPVTKSFNRGEC |
| 67. | h201H3.1 + h219L1.1 G2C full length nucleotide sequence of light chain | GACATCCAGATGACTCAGAGCCCAAGCTCTCTGAGCG
CCAGCGTGGGAGATAGGGTCACAATCACTTGTAGGGC
CAGCCAAGAGGTGAGCGGCTATCTGAATTGGCTCCAG
CAGAAACCCGGCAAGGCCATCAAGAGACTGATCTATG
CCGCCAGCACTCTGGAGTCCGGAGTGCCATCTAGGTT
CAGCGGCAGCAGAAGCGGCAGCGACTACACTCTCACA
ATCAGCTCCCTCCAGCCAGAAGACTTCGCCACTTACT
ACTGTCTGCAGTATGCCAGCTACCCAAGGACTTTCGG
ACAGGGTACCAAGGTGGAGATCAAAAGAACCGTGGCC
GCTCCTTCCGTGTTCATCTTCCCTCCCTCCGACGAGC
AGCTGAAGAGCGGAACAGCCTCTGTCGTGTGCCTCCT
GAACAACTTCTACCCCGGGAGGCCAAGGTCCAGTGG
AAGGTGGACAACGCTCTGCAGAGCGGCAACTCTCAGG
AGAGCGTGACAGAGCAGGACTCCAAGGACTCCACCTA
CTCCCTGTCTTCCACCCTGACCCTGTCTAAGGCCGAC
TACGAGAAGCACAAGGTGTACGCTTGCGAGGTGCACA
CCAGGGACTGTCCTCTCCAGTGACCAAGTCCTTCAA
CCGCGGCGAGTGT |
| 68. | h201H3.1 + h201L1.1dmut G2CVL amino acid sequence | DIQMTQSPSSLSASVGDRVTITCRASQEIRGYLIWLQ
QKPGKAIKRLIYAASTLESGVPSRFSGSRSGSDYTLT
ISSLQPEDFATYYCLQYTSYPRTFGQGTKVEIK |
| 69. | h201H3.1 + h201L1.1dmut G2CVL nucleotide sequence | GACATCCAGATGACACAGTCCCCTAGCTCTCTGTCCG
CCAGCGTGGGAGATAGGGTCACAATCACTTGTAGGGC
CAGCCAAGAGATTAGGGGCTATCTGATCTGGCTGCAG
CAGAAACCCGGCAAGGCCATCAAGAGGCTGATCTACG
CCGCCAGCACTCTGGAGAGCGGAGTCCCAAGCAGATT
TTCCGGCAGCCGCTCCGGCAGCGATTACACTCTCACA
ATCAGCTCTCTGCAGCCAGAGGACTTCGCCACTTACT
ACTGTCTGCAGTACACAAGCTACCCAAGGACATTCGG
CCAAGGCACTAAGGTGGAGATCAAA |
| 70. | h201H3.1 + h201L1.1dmut G2C full length amino acid sequence of light chain | DIQMTQSPSSLSASVGDRVTITCRASQEIRGYLIWLQ
QKPGKAIKRLIYAASTLESGVPSRFSGSRSGSDYTLT
ISSLQPEDFATYYCLQYTSYPRTFGQGTKVEIKRTVA
APSVFIFPPSDEQLKSGTASVVCLLNNFYPREAKVQW
KVDNALQSGNSQESVTEQDSKDSTYSLSSTLTLSKAD
YEKHKVYACEVTHQGLSSPVTKSFNRGEC |
| 71. | h201H3.1 + h201L1.1dmut G2C full length nucleotide sequence of light chain | GACATCCAGATGACACAGTCCCCTAGCTCTCTGTCCG
CCAGCGTGGGAGATAGGGTCACAATCACTTGTAGGGC
CAGCCAAGAGATTAGGGGCTATCTGATCTGGCTGCAG
CAGAAACCCGGCAAGGCCATCAAGAGGCTGATCTACG
CCGCCAGCACTCTGGAGAGCGGAGTCCCAAGCAGATT
TTCCGGCAGCCGCTCCGGCAGCGATTACACTCTCACA
ATCAGCTCTCTGCAGCCAGAGGACTTCGCCACTTACT
ACTGTCTGCAGTACACAAGCTACCCAAGGACATTCGG
CCAAGGCACTAAGGTGGAGATCAAAAGAACCGTGGCC
GCTCCTTCCGTGTTCATCTTCCCTCCCTCCGACGAGC
AGCTGAAGAGCGGAACAGCCTCTGTCGTGTGCCTCCT
GAACAACTTCTACCCCGGGAGGCCAAGGTCCAGTGG |

TABLE 1-continued

Description of the sequence listing of the invention

| SEQ ID NO: | Sequence Description | Sequence |
|---|---|---|
| | | AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |
| 72. | M201 HuH1L1(D-E) G2C VH amino acid sequence | EVQLVESGGGLVQPGGSLRLSCAASGFTFSDYGMHWV RQAPGKGLEWVSYISSGSSIMYYADTVKGRFTISRDN AKNSLYLQMNSLRAEDTAVYYCARDLYYDHVLDYWGQ GTLLTVSS |
| 73. | M201 HuH1L1(D-E) G2C VH nucleotide sequence | GAGGTGCAGCTGGTGGAGAGCGGCGGCGGCCTGGTGC AGCCCGGCGGCAGCCTGAGACTGAGCTGCGCCGCCAG CGGCTTCACCTTCAGCGACTACGGCATGCACTGGGTG AGACAGGCCCCCGGCAAGGGCCTGGAGTGGGTGAGCT ACATCAGCAGCGGCAGCAGCATCATGTACTACGCCGA CACCGTGAAGGGCAGATTCACCATCAGCAGAGACAAC GCCAAGAACAGCCTGTACCTGCAGATGAACAGCCTGA GAGCCGAGGACACCGCCGTGTACTACTGCGCCAGAGA CCTGTACTACGACCACGTGCTGGACTACTGGGGCCAG GGCACCCTGCTGACCGTGAGCAGC |
| 74. | M201 HuH1L1(D-E) G2C VL amino acid sequence | DIQMTQSPSSLSASVGDRVTITCRASQEIRGYLIWLQ QKPGGAIKRLIYAASTLESGVPSRFSGSRSGTDFTLT ISSLQPEDFATYYCLQYTSYPRTFGGGTKVEIK |
| 75. | M201 HuH1L1(D-E) G2C VL nucleotide sequence | GACATCCAGATGACCCAGAGCCCCAGCAGCCTGAGCG CCAGCGTGGGCGACAGAGTGACCATCACCTGCAGAGC CAGCCAGGAGATCAGAGGCTACCTGATCTGGCTGCAG CAGAAGCCCGGCGGCGCCATCAAGAGACTGATCTACG CCGCCAGCACCCTGGAGAGCGGCGTGCCCAGCAGATT CAGCGGCAGCAGAAGCGGCACCGACTTCACCCTGACC ATCAGCAGCCTGCAGCCCGAGGACTTCGCCACCTACT ACTGCCTGCAGTACACCAGCTACCCCAGAACCTTCGG CGGCGGtACCAAGGTGGAGATCAAG |
| 76. | M201 HuH1L1(D-E) G2C full length amino acid sequence of heavy chain | EVQLVESGGGLVQPGGSLRLSCAASGFTFSDYGMHWV RQAPGKGLEWVSYISSGSSIMYYADTVKGRFTISRDN AKNSLYLQMNSLRAEDTAVYYCARDLYYDHVLDYWGQ GTLLTVSSASTKGPSVFPLAPCSRSTSESTAALGCLV KDYFPEPVTVSWNSGALTSGVHTFPAVLQSSGLYSLS SVVTVPSSNFGTQTYTCNVDHKPSNTKVDKTVERKCC VECPPCPAPPVAGPSVFLFPPKPKDTLMISRTPEVTC VVVDVSHEDPEVQFNWYVDGVEVHNAKTKPREEQFNS TFRVVSVLTVVHQDWLNGKEYKCKVSNKGLPAPIEKT ISKTKGQPREPQVYTLPPSREEMTKNQVSLTCLVKGF YPSDIAVEWESNGQPENNYKTTPPMLDSDGSFFLYSK LTVDKSRWQQGNVFSCSVMHEALHNHYTQKSLSLSPG K |
| 77. | M201 HuH1L1(D-E) G2C full length nucleotide sequence of heavy chain | GAGGTGCAGCTGGTGGAGAGCGGCGGCGGCCTGGTGC AGCCCGGCGGCAGCCTGAGACTGAGCTGCGCCGCCAG CGGCTTCACCTTCAGCGACTACGGCATGCACTGGGTG AGACAGGCCCCCGGCAAGGGCCTGGAGTGGGTGAGCT ACATCAGCAGCGGCAGCAGCATCATGTACTACGCCGA CACCGTGAAGGGCAGATTCACCATCAGCAGAGACAAC GCCAAGAACAGCCTGTACCTGCAGATGAACAGCCTGA GAGCCGAGGACACCGCCGTGTACTACTGCGCCAGAGA CCTGTACTACGACCACGTGCTGGACTACTGGGGCCAG GGCACCCTGCTGACCGTGAGCAGCGCTAGCACCAAGG GACCCTCCGTGTTTCCTCTGGCTCCTTGCTCCAGATC TACCTCCGAGTCTACCGCCGCTCTGGGTTGTCTGGTG AAGGACTACTTCCCCGAGCCAGTGACCGTGTCTTGGA ACAGCGGAGCTCTGACATCCGGAGTGCACACCTTTCC AGCCGTGCTGCAGTCTTCCGGCCTGTATTCTCTGTCC TCCGTGGTGACCGTGCCTTCTTCCAACTTCGGCACCC AGACCTACACTTGCAACGTGGACCACAAGCCCTCCAA CACCAAGGTGGACAAGACCGTGGAGCGCAAGTGTTGC GTCGAGTGCCCTCCTTGCCCAGCTCCTCCAGTGGCCG GACCTTCTGTGTTTCTGTTCCCCCCTAAGCCTAAGGA CACCCTGATGATCTCCCGGACCCCAGAAGTGACTTGC |

TABLE 1-continued

Description of the sequence listing of the invention

| SEQ ID NO: | Sequence Description | Sequence |
|---|---|---|
| | | GTGGTGGTGGACGTGTCTCACGAGGACCCCGAGGTGC AGTTCAATTGGTACGTGGACGGCGTGGAGGTGCACAA CGCTAAGACCAAGCCCAGGGAGGAGCAGTTCAACTCC ACCTTCCGGGTGGTGTCAGTGCTGACAGTGGTGCACC AGGATTGGCTGAACGGCAAGGAGTACAAGTGCAAGGT GTCCAACAAGGGCCTGCCAGCTCCTATCGAGAAGACC ATCTCCAAGACCAAGGGCCAGCCCAGAGAGCCTCAGG TGTACACACTGCCTCCTTCCCGGGAGGAGATGACCAA GAACCAGGTGTCCCTGACTTGCCTCGTGAAGGGATTC TACCCCTCCGACATCGCAGTCGAGTGGGAATCCAACG GCCAGCCCGAGAACAACTACAAGACCACCCCTCCTAT GCTGGACTCCGACGGCTCCTTCTTCCTGTACTCCAAG CTGACCGTGGACAAGTCCCGTTGGCAGCAGGGCAACG TGTTCTCTTGCAGCGTGATGCACGAGGCCCTGCACAA CCACTACACCCAGAAGAGCCTGTCCCTGTCTCCCGGC AAG |
| 78. | M201 HuH1L1(D-E) G2C full length amino acid sequence of light chain | DIQMTQSPSSLSASVGDRVTITCRASQEIRGYLIWLQ QKPGGAIKRLIYAASTLESGVPSRFSGSRSGTDFTLT ISSLQPEDFATYYCLQYTSYPRTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 79. | M201 HuH1L1(D-E) G2C full length nucleotide sequence of light chain | GACATCCAGATGACCCAGAGCCCCAGCAGCCTGAGCG CCAGCGTGGGCGACAGAGTGACCATCACCTGCAGAGC CAGCCAGGAGATCAGAGGCTACCTGATCTGGCTGCAG CAGAAGCCCGGCGGCGCCATCAAGAGACTGATCTACG CCGCCAGCACCCTGGAGAGCGGCGTGCCCAGCAGATT CAGCGGCAGCAGAAGCGGCACCGACTTCACCCTGACC ATCAGCAGCCTGCAGCCCGAGGACTTCGCCACCTACT ACTGCCTGCAGTACACCAGCTACCCCAGAACCTTCGG CGGCGGtACCAAGGTGGAGATCAAGAGAACCGTGGCC GCTCCTTCCGTGTTCATCTTCCCTCCCTCCGACGAGC AGCTGAAGAGCGGAACAGCCTCTGTCGTGTGCCTCCT GAACAACTTCTACCCCCGGGAGGCCAAGGTCCAGTGG AAGGTGGACAACGCTCTGCAGAGCGGCAACTCTCAGG AGAGCGTGACAGAGCAGGACTCCAAGGACTCCACCTA CTCCCTGTCTTCCACCCTGACCCTGTCTAAGGCCGAC TACGAGAAGCACAAGGTGTACGCTTGCGAGGTGACAC ACCAGGGACTGTCCTCTCCAGTGACCAAGTCCTTCAA CCGCGGCGAGTGT |

DETAILED DESCRIPTION

Definitions

Figure 1:
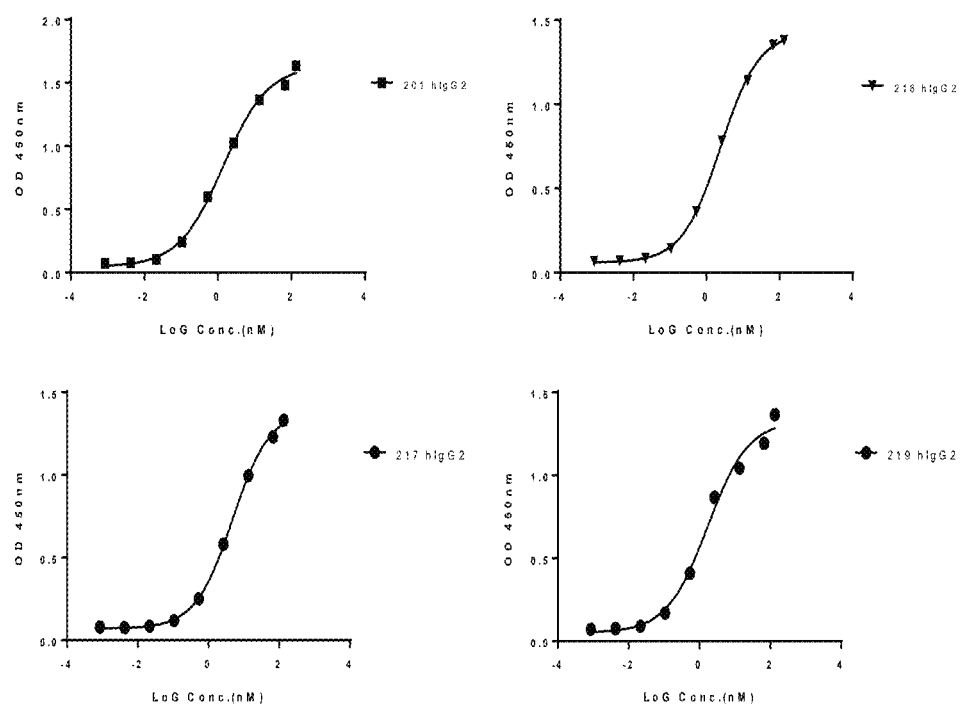
FIG. 1 shows the binding ability assay of chimeric CD39 antibody and soluble huCD39 protein.

In order that the present description may be more readily understood, certain terms are firstly defined. Additional definitions are set forth throughout the detailed description.

Human CD39, also known as NTPdaseI, ENTPD1, ATP-Dase and vascular ATP diphosphohydrolase, International Enzymology Commission number of EC 3.6.1.5, exhibits ATPase activity. CD39 hydrolyzes extracellular ATP and ADP to AMP, and AMP is further converted to adenosine by 5-prime nucleotidase. The amino acid sequence of the human CD39 mature polypeptide chain is shown in Genbank under accession number of P49961.

The term "antibody" as used herein may include whole antibodies and any antigen binding fragments (i.e., "antigen-binding portions") or single chains thereof. An "antibody" refers, in one embodiment, to a glycoprotein or an antigen binding portion thereof comprising at least two heavy (H) chains and two light (L) chains inter-connected by disulfide bonds. Each heavy chain is comprised of a heavy chain variable region (abbreviated herein as VH) and a heavy chain constant region. In some naturally occurring IgG, IgD and IgA antibodies, the heavy chain constant region is comprised of three domains, CH1, CH2 and CH3. In some naturally occurring antibodies, each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), and regions that are more conserved, termed framework regions (FR), both of which are intermingled arrangement. Herein, the CDRs of the VH region are abbreviated as HCDRs, that is, the three CDRs of the VH region can be abbreviated as HCDR1, HCDR2, and HCDR3; the CDRs of the VL region are abbreviated as LCDR, that is, the three CDRs of the VL region can be abbreviated as LCDR1, LCDR2, LCDR3. Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system (C1q).

The heavy chain of an antibody may or may not contain a terminal lysine (K), or a terminal glycine and lysine (GK). Thus, any of the heavy chain sequences and heavy chain constant region sequences provided herein can end in either GK or K, or lack K or GK, regardless of what the last amino acid of the sequence provides. This is because the terminal lysine and sometimes glycine and lysine are cleaved during expression of the antibody.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate binding nonspecifically. As used herein, an antibody that "binds specifically" to an antigen refers to an antibody that binds to the antigen and substantially identical antigens with high affinity, which means having a $K_D$ of $10^{-7}$M or less, preferably $10^{-8}$M or less, even more preferably $5\times10^{-9}$ M or less, and most preferably between $10^{-8}$ M and $10^{-10}$M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% or greater sequence identity to the sequence of the given antigen. An immunoglobulin may be from any of the commonly known isotypes, including but not limited to IgA, secretory IgA, IgG and IgM. The IgG isotype is divided in subclasses in some species: IgG1, IgG2, IgG3 and IgG4 in humans, and IgG1, IgG2a, IgG2b and IgG3 in mice. In certain embodiments, the anti-CD39 antibodies described herein are of the human IgG1 or IgG2 subtype. Immunoglobulins, e.g., human IgG1, exist in several allotypes, which differ from each other in at most a few amino acids. "Antibody" may include, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human CD39). It has been shown that the antigen-binding function of an antibody can be performed by fragments of a full-length antibody. Examples of binding fragments encompassed within the term "antigen-binding portion" of an antibody, e.g., an anti-CD39 antibody described herein, include (i) a Fab fragment, which is a monovalent fragment consisting of the VL, VH, CL and CH1 domains; (ii) a F(ab')$_2$ fragment, which is a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) or (vii) a combination of two or more isolated CDRs which may optionally be linked by a synthetic linker. Furthermore, although the two domains of the Fv fragment, VL and VH, are encoded by different genes, they can be linked, using recombinant methods, by a synthetic linker that enables them to be made as a single protein chain in which the VL and VH regions pair to form monovalent molecules known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" of an antibody. These and other potential constructs are described at Chan & Carter (2010) *Nat. Rev. Immunol.* 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "amino acid sequence of conservative modifications form" refers to the amino acid modifications that do not significantly affect or alter the binding characteristics of the antibody containing the amino acid sequence, and the modifications include amino acid substitutions, additions and deletions. Modifications can be introduced into an antibody of the invention by standard techniques, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function using the functional assays described herein. Preferably, the conservative modifications are no more than one or two in number.

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "monoclonal antibody," as used herein, refers to an antibody that displays a single binding specificity and affinity for a specific epitope or a composition of antibodies in which all antibodies display a single binding specificity and affinity for a specific epitope. Typically such monoclonal antibodies will be derived from a single antibody encoding cell or nucleic acid, and will be propagated without intentionally introducing any sequence alterations. Accordingly, the term "human monoclonal antibody" refers to a monoclonal antibody that has variable and optional constant regions derived from human germ line immunoglobulin sequences. In one embodiment, human monoclonal antibodies are produced by a hybridoma, for example, obtained by fusing a B cell derived from a transgenic or transchromosomal non-human animal (e.g., a transgenic mouse having a genome comprising a human heavy chain transgene and a light chain transgene), with an immortalized cell.

The term "recombinant human antibody," as used herein, includes all human antibodies that are prepared, expressed, produced or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, produced or isolated by any other means that involve splicing of human immunoglobulin gene sequences to other DNA sequences. Such recombinant human antibodies comprise variable and constant regions that utilize specific human germline immunoglobulin sequences and are encoded by the germline genes, but include subsequent rearrangements and mutations that occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for an exogenous antigen. In addition to rearrangement, the variable region can be further modified by multiple single amino acid changes (referred to as somatic mutation or hypermutation) to increase the affinity of the antibody to the exogenous antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germ line immunoglobulin sequences. Furthermore, if the antibody contains a constant region, the constant region is also derived from human germ line immunoglobulin sequences. The antibodies described herein may include amino acid residues not encoded by human germ line immunoglobulin sequences (e.g., mutations introduced by random or site-specific mutagenesis in vitro or by somatic mutation in vivo). However, the term "human antibody", as used herein, is not intended to include antibodies in which CDR sequences derived from the germ line of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of an antibody in humanized form, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a specific antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

A "modified heavy chain constant region" refers to a heavy chain constant region comprising the constant domains CH1, hinge, CH2, and CH3, wherein one or more of the constant domains are from a different isotype (e.g. IgG1, IgG2, IgG3, IgG4). In some embodiments, the modified constant region includes a human IgG2 CH1 domain and a human IgG2 hinge fused to a human IgG1 CH2 domain and a human IgG1 CH3 domain. In certain embodiments, such modified constant regions also include amino acid modifications within one or more of the domains relative to the wild type amino acid sequence.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants in a specific isotype group, which variants differ in a few amino acids (see, e.g., Jefferis et al. (2009) mAbs 1: 1). Antibodies described herein may be of any allotype.

Unless specified otherwise herein, all amino acid numbers are according to the EU index of the Kabat system (Kabat, E. A., et al. (1991) Sequences of Proteins of Immunological Interest, Fifth Edition, U.S. Department of Health and Human Services, NIH Publication No. 91-3242).

The terms "an antibody recognizing an antigen" and "an antibody specific for an antigen" are used interchangeably herein with the term "an antibody which binds specifically to an antigen."

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated hagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating receptors (FcγRI, FcγRIII, and FcγRIV in mice; FcγRIA, FcγRIIA, and FcγRIIIA in humans) and one inhibitory receptor (FcγRIIB) Various properties of human FcγRs are summarized in Table A. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but does not express the inhibitory FcγRIIB in mice and humans. Human IgG1 binds to most human Fc receptors and is considered that the types of activating Fc receptors which it binds to are equivalent to murine IgG2a.

TABLE A

Characteristics of human FcγRs

| Fcγ | Allelic variants | Affinity for human IgG | Isotype preference | Cellular distribution |
| --- | --- | --- | --- | --- |
| FcγRI | None described | High ($K_D$ ~10 nM) | IgG1 = 3 > 4 >> 2 | Monocytes, macrophages, activated neutrophils, dentritic cells |
| FcγRIIA | H131 | Low to medium | IgG1 > 3 > 2 > 4 | Neutrophils, monocytes, |
|  | R131 | Low | IgG1 > 3 > 4 > 2 | macrophages, eosinophils, dentritic cells, platelets |
| FcγRIIIA | V158 | Medium | IgG1 = 3 >> 4 > 2 | NK cell, monocytes, |
|  | F158 | Low | IgG1 = 3 >> 4 > 2 | macrophages, mast cells, eosinophils, dentritic cell |
| FcγRIIB | I232 | Low | IgG1 = 3 = 4 > 2 | B cells, monocytes, |
|  | T232 | Low | IgG1 = 3 = 4 > 2 | macrophages, dentritic cells, mast cells |

A "hinge", "hinge domain" or "hinge region" or "antibody hinge region" refers to the domain of a heavy chain constant region that links the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. The term "hinge" includes wildtype hinges, as well as variants thereof (e.g., non-naturally-occurring hinges or modified hinges). For example, the term "IgG2 hinge" includes wildtype IgG2 hinge, and variants having 1, 2, 3, 4, 5, 1-3, 1-5, 3-5 and/or at most 5, 4, 3, 2, or 1 mutations, e.g., substitutions, deletions or additions.

The term "CH1 domain" refers to the heavy chain constant region linking the variable domain to the hinge in a heavy chain constant domain. The term "CH1 domain" includes wildtype CH1 domains, as well as variants thereof (e.g., non-naturally-occurring CH1 domains or modified CH1 domains). For example, the term "CH1 domain" includes wildtype CH1 domains and variants thereof having 1, 2, 3, 4, 5, 1-3, 1-5, 3-5 and/or at most 5, 4, 3, 2, or 1 mutations, e.g., substitutions, deletions or additions.

Exemplary CH1 domains include CH1 domains with mutations that change a biological activity of an antibody, such as ADCC, CDC or half-life period. Modifications to the CH1 domain that affect a biological activity of an antibody are provided herein.

The term "CH2 domain" refers to the heavy chain constant region linking the hinge in a heavy chain constant domain to the CH3 domain. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants thereof having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that change a biological activity of an antibody, such as ADCC, CDC or half-life.

The term "CH3 domain" refers to the heavy chain constant region that is C-terminal to the CH2 domain in a heavy chain constant domain. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants thereof having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that change a biological activity of an antibody, such as ADCC, CDC or half-life period. Modifications to the CH3 domain that affect a biological activity of an antibody are provided herein.

A "CL domain" refers to the constant domain of a light chain. The term "CL domain" includes wildtype CL domains and variants thereof.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof.

Native sequence Fc includes the various allotypes of Fcs (see, e.g., Jefferis et al. (2009) mAbs 1: 1).

The term "epitope" or "antigenic determinant" refers to a site on an antigen (e.g., CD39) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained when exposing to denaturing solvents, whereas epitopes formed by tertiary folding are typically lost when treating with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation analysis, wherein overlapping or contiguous peptides (e.g., from CD39) are tested for reactivity with a given antibody (e.g., anti-CD39 antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

The term "epitope mapping" refers to the process of identification of the molecular determinants on the antigen involved in antibody-antigen recognition.

The term "binds to the same epitope" with reference to two or more antibodies means that the antibodies bind to the same segment of amino acid residues, as determined by a given method. Techniques for determining whether antibodies bind to the "same epitope on CD39" of the antibodies described herein include, for example, epitope mapping methods, such as, x-ray analyses of crystals of antigen: antibody complexes, which provide atomic resolution of the epitope, and hydrogen/deuterium exchange mass spectrometry (HDX-MS). Other methods that monitor the binding of the antibody to antigen fragments (e.g. proteolytic fragments) or to mutated variations of the antigen where loss of binding due to a modification of an amino acid residue in the antigen sequence is often considered an indication of an epitope component (e.g. alanine scanning mutagenesis—Cunningham & Wells (1985) Science 244: 1081). In addition, computational combinatorial methods for epitope mapping can also be used. These methods rely on the ability of the antibody of interest from combinatorial phage display peptide libraries to affinity isolate specific short peptides.

Antibodies that "compete with another antibody for binding to a target" refer to antibodies that inhibit (partially or completely inhibit) the binding of another antibody to the target. Whether the two antibodies compete with each other for binding to a target, i.e., whether and to what extent one antibody inhibits the binding of another antibody to a target, may be determined using known competition experiments, such as those described in the Examples. In certain embodiments, an antibody competes with another antibody, and inhibit at least 10%, 20%, 30%, 40%, 50%, 60%, 70%, 80%, 90% or 100% of the binding. The extent of inhibition or competition may be different depending on which antibody is the "blocking antibody" (i.e., the cold antibody that is incubated first with the target). Competition assays can be conducted as described, for example, in Ed Harlow and David Lane, Cold Spring Harb Pro toe; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, the overlapping epitope or the adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich analysis (see Harlow and Lane, Antibodies: A Laboratory Manual, Cold Spring Harbor Press (1988)); solid phase direct label MA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$M, such as approximately less than $10^{-8}$M, $10^{-9}$M or $10^{-10}$ M or even lower when determined by, e.g., surface plasmon resonance (SPR) technology in a BIACORE® 2000 surface plasmon resonance instrument using the predetermined antigen, e.g., recombinant human CD39, as the analyte and the antibody as the ligand, or Scatchard analysis of binding of the antibody to antigen positive cells, and (ii) binds to the predetermined antigen with an affinity that is at least two-times greater than its affinity for binding to a non-specific antigen (e.g., BSA, casein) other than the predetermined antigen or a closely-related antigen. Accordingly, unless otherwise indicated, an antibody that "specifically binds to human CD39" refers to an antibody that binds to soluble or cell bound human CD39 with a $K_D$ of $10^{-7}$M or less, such as approximately less than $10^{-8}$M, $10^{-9}$M or $10^{-10}$ M or even lower. An antibody that "cross-reacts with cynomolgus CD39" refers to an antibody that binds to cynomolgus CD39 with a $K_D$ of $10^{-7}$M or less, such as less than $10^{-8}$M, $10^{-9}$M or $10^{-10}$ M or even lower. In certain embodiments, antibodies that do not cross-react with CD39 from a non-human species exhibit essentially undetectable binding against these proteins in standard binding assays.

The term "Kassoc" or "Ka", as used herein, is intended to refer to the association rate constant of a specific antibody-antigen interaction, whereas the term "Kdis" or "Kd" as used herein, is intended to refer to the dissociation rate constant of a specific antibody-antigen interaction. The term "$K_D$", as used herein, is intended to refer to the equilibrium dissociation constant, which is obtained from the ratio of Kd to Ka (i.e., Kd/Ka) and is expressed as a molar concentration (M). $K_D$ values of antibodies can be determined using methods well established in the art. A preferred method for determining the $K_D$ of an antibody is to analyze by using surface plasmon resonance, preferably using a biosensor system such as a Biacore® surface plasmon resonance system or flow cytometry and Scatchard.

The term "EC50" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be a single chain or a double chain, and may be cDNA. Also provided are "conservative sequence modifications" of the sequences set forth in SEQ ID NOs described herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs described herein by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD39 antibody is preferably replaced with another amino acid residue from the same side chain family. Methods of identifying nucleotide and amino acid conservative substitutions that do not eliminate antigen binding are well-known in the art (see, e.g., Brummell et al., Biochem. 32: 1180-1187 (1993); Kobayashi et al. Protein Eng. 12(10): 879-884 (1999); and Burks et al. Proc. Natl. Acad. Sci. USA 94:412-417 (1997)). Alternatively, in another embodiment, mutations can be introduced randomly along all or part of an anti-CD39 antibody encoding sequence, such as by saturation mutagenesis, and the resulting modified anti-CD39 antibodies can be screened through improved binding activity.

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial identity exists when the segments will hybridize under selective hybridization conditions, to the complement of the chain.

For polypeptides, the term "substantial identity" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The identity % between two sequences is a function of the number of identical positions shared by the sequences when the sequences are optimally aligned (i.e., identity %=number of identical positions/total number of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. (48): 444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform searches against public databases to, for example, identify related sequences. Such searches can be performed with the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences identical to the nucleic acid molecules described herein. BLAST protein searches can be performed with the XBLAST program, score=50, wordlength=3 to obtain amino acid sequences identical to the protein molecules described herein. To obtain gapped alignments for comparison purposes, Gapped BLAST can be used as described in Altschul et al., (1997) Nucleic Acids Res. 25(17):3389-3402. When using BLAST and Gapped BLAST programs, the default parameters of the respective programs (e.g., XBLAST and NBLAST) can be used. See www.ncbi.nlm.nih.gov.

These nucleic acids may be present in whole cells, in a cell lysate, or in a partially purified or substantially pure form. The nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For encoding sequences, these mutations may affect amino acid sequence as desired. Specifically, DNA sequences substantially identical to or derived from native V, D, J, constant, switches and other such sequences described herein are contemplated.

The term "vector," as used herein, is intended to refer to a nucleic acid molecule capable of transporting another nucleic acid to which it has been linked. One type of vector is "plasmid," which refers to a circular double chains DNA loop into which other DNA segments may be linked. Another type of vector is a viral vector, wherein other DNA segments may be linked into the viral genome. Some vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell when introduced into the host cell, and thereby are replicated along with the host genome. Moreover, some vectors are capable of directing the expression of genes to which they are operatively linked. Such vectors are referred to herein as "recombinant expression vectors" (or simply, "expression vectors"). In general, expression vectors used in recombinant DNA techniques are often in the form of plasmids. In the present description, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the specific subject cell but to the progeny of such a cell. Since certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be CD39 or a fragment thereof.

An "immune response" refers to a biological response in a vertebrate for exogenous agents, such response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement), the action results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or inhibition of a Treg cell.

An "immunomodulator" or "immunoregulator" refers to an agent, e.g., a component of a signaling pathway, which may be involved in modulating, regulating, or modifying an immune response. "Modulating," "regulating," or "modifying" an immune response refers to any changes in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. The immunomodulator may be located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

An increased ability of stimulating an immune response, or the immune system, can result from an enhanced agonist activity of T cell co-stimulatory receptors and/or an enhanced antagonist activity of inhibitory receptors. An increased ability of stimulating an immune response or the immune system may be reflected by a time increase of the EC50 or maximal level of activity in an assay that measures an immune response, e.g., an assay that measures changes in cytokine or chemokine release, cytolytic activity (determined directly on target cells or indirectly via detecting CD 107a or granzymes) and proliferation. The ability of stimulating an immune response or the immune system activity may be enhanced by at least 10%, 30%, 50%, 75%, 2 times, 3 times, 5 times or more.

"Immunotherapy" refers to the treatment of a subject afflicted with, or at risk of contracting or suffering a recurrence of, a disease by a method comprising inducing, enhancing, suppressing or otherwise modifying an immune response.

"Immuno stimulating therapy" or "immuno stimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"T effector" ("Teff") cells refers to T cells (e.g., CD4+ and CD8+ T cells) as well as T helper (Th) cells with cytolytic activities, which secrete cytokines and activate and direct other immune cells, but does not include regulatory T cells (Treg cells).

As used herein, the term "linkage" refers to the association of two or more molecules. The linkage can be covalent or non-covalent. The linkage also can be genetic (i.e., recombinantly fused). Such linkages can be achieved using a wide variety of art recognized techniques, such as chemical coupling and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, but not limited, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

In the context herein, when referring to the CD39 polypeptide, "inhibit", "neutralize" or "neutralizing" (e.g., "neutralize CD39", "neutralize the activity of CD39" or "neutralize the enzymatic activity of CD39", etc.) refers to a process in which the ATP hydrolysis activity (ATPase) of CD39 is inhibited. This particularly comprises the inhibition of CD39-mediated generation of AMP and/or ADP, i.e., the inhibition of CD39-mediated catabolism of ATP to AMP and/or ADP. This can be measured for example in a cellular assay that measures the capacity of a test compound to inhibit the conversion of ATP to AMP and/or ADP, either directly or indirectly. For example, disappearance of ATP and/or generation of AMP can be assessed, as described herein.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can particularly involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

As used herein, "cancer" refers a broad group of diseases characterized by the uncontrolled growth of abnormal cells in the body. Since unregulated cell division may result in the formation of malignant tumors or cells, they would invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

A "hematological malignancy" includes lymphoma, leukemia, myeloma or lymphoid malignancy, as well as cancers of the spleen and lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia, acute myelogenous leukemia, chronic myelogenous leukemia, and acute lymphoblastic leukemia. Hematological malignancies further include myelomas, such as, but not limited to, multiple myeloma and smoldering multiple myeloma. Other hematological and/or B cell- or T-cell-related cancers are encompassed by the term hematological malignancy.

The term "effective dose" or "effective dosage" is defined as an amount sufficient to achieve or at least partially achieve a desired effect. A "therapeutically effective dose" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective dose" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to those skilled in the art, such as in human subjects during clinical trials, in animal model systems predictive of efficacy in humans, or by assaying the activity of the agent in in-vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective dose or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective dose or dosage of the drug completely inhibits cell growth or tumor growth, i.e., preferably inhibits cell growth or tumor growth by 100%. The ability of a compound to inhibit tumor growth can be evaluated using the assays described infra. Alternatively, this characteristic of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

The terms "patient" and "subject" refer to any human or non-human animal that receives either prophylactic or therapeutic treatment. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

EXAMPLES

Example 1: Screening and Identifying of CD39 Antibody

C57/BL6 mice were immunized with human CD39 extracellular domain recombinant protein (huCD39). The first immunization (intraperitoneal injection) was performed with an emulsion of 50 µg of huCD39 protein and complete Freund's adjuvant, the second immunization (subcutaneous injection) was performed with an emulsion of 25 µg of huCD39 protein and incomplete Freund's adjuvant, the third immunization (intraperitoneal injection) was performed with an emulsion of 25 µg of huCD39 protein and incomplete Freund's adjuvant, and the fourth immunization (subcutaneous injection) was performed with an emulsion of 25 µg of huCD39 protein and incomplete Freund's adjuvant. Finally, a final booster immunization (intraperitoneal injection) was performed with 50 µg of huCD39 protein. A fraction of immunized spleen cells was fused with SP2/0 cells to prepare hybridoma cells by electrofusion after four days of this booster. Primary screening was performed by ELISA and flow cytometry, furthermore, enzyme viability blocking activity was screened with a 293T/17 cell line expressing huCD39 (293T/17-huCD39), and screened by the reversal of CD4+ T cell proliferation inhibition. At last, four murine-derived antibodies with CD39 enzyme activity blocking ability were obtained.

Example 2: The Binding of Chimeric Antibodies to huCD39 Detected by Indirect ELISA The Fv region of the four mouse-derived antibodies obtained in Example 1 was fused with the human IgG2 Fc region and constructed into the pcDNA3.1 vector. Then transfected 293F cells to express the antibody proteins, and the antibodies were purified by ProteinA affinity chromatography. Four chimeric antibodies 201 hIgG2, 216 hIgG2, 217 hIgG2 and 219 hIgG2 were obtained, and the sequence descriptions of four chimeric antibodies are detailed in Table I-1. The affinity of the chimeric antibodies was detected by indirect ELISA: 1 µg/mL of huCD39 recombinant protein (Yiqiao Shenzhou, Sino Biological) was coated on ELISA plates (Coning, Inc.) and incubated overnight at 4° C. The next day, the plates were washed 5 times with PBS buffer and blocked with 200 µL/well of 2% skimmed milk powder for 1 h. A certain dose range of chimeric CD39 antibody was incubated for 1 h at room temperature; then washed 5 times with PBST washing buffer (PBS, 0.05% Tween 20). 100 µL of HRP-labeled secondary antibody was added to each well and the plates were incubated for 30 min at room temperature. The plates were washed 5 times again and TMB (Life Technologies) was added for color development for 5 to 10 min. At last, 1N HCl was added to terminate the reaction, and the OD value was measured at 450 nm. GraphPad Prism software was used to generate data plots and the affinity data was counted (FIG. 1). As shown in Table 1, the $EC_{50}$ values of the binding activities of the four chimeric antibodies 201 hIgG2, 216 hIgG2, 217 hIgG2 and 219 hIgG2 were all at the level of $10^{-9}$M.

TABLE I-1

| No. | | Variable region amino acid sequence | Variable region nucleotide sequence | Amino acid sequence | Nucleotide sequence |
|---|---|---|---|---|---|
| 201 hIgG2 | Heavy chain | SEQ ID NO: 3 | SEQ ID NO: 4 | SEQ ID NO: 13 | SEQ ID NO: 14 |
| | Light chain | SEQ ID NO: 8 | SEQ ID NO: 9 | SEQ ID NO: 15 | SEQ ID NO: 16 |
| 216 hIgG2 | Heavy chain | SEQ ID NO: 17 | SEQ ID NO: 18 | SEQ ID NO: 27 | SEQ ID NO: 28 |
| | Light chain | SEQ ID NO: 22 | SEQ ID NO: 23 | SEQ ID NO: 29 | SEQ ID NO: 30 |
| 217 hIgG2 | Heavy chain | SEQ ID NO: 31 | SEQ ID NO: 32 | SEQ ID NO: 41 | SEQ ID NO: 42 |
| | Light chain | SEQ ID NO: 36 | SEQ ID NO: 37 | SEQ ID NO: 43 | SEQ ID NO: 44 |
| 219 hIgG2 | Heavy chain | SEQ ID NO: 45 | SEQ ID NO: 46 | SEQ ID NO: 55 | SEQ ID NO: 56 |
| | Light chain | SEQ ID NO: 50 | SEQ ID NO: 51 | SEQ ID NO: 57 | SEQ ID NO: 58 |

TABLE 1

Affinity of chimeric antibodies

| Antibody | Bottom | Top | $EC_{50}$(nM) |
|---|---|---|---|
| 201 hIgG2 | 0.046 | 1.636 | 1.395 |
| 216 hIgG2 | 0.060 | 1.427 | 2.426 |
| 217 hIgG2 | 0.070 | 1.391 | 4.801 |
| 219 hIgG2 | 0.052 | 1.330 | 1.690 |

Figure 2:
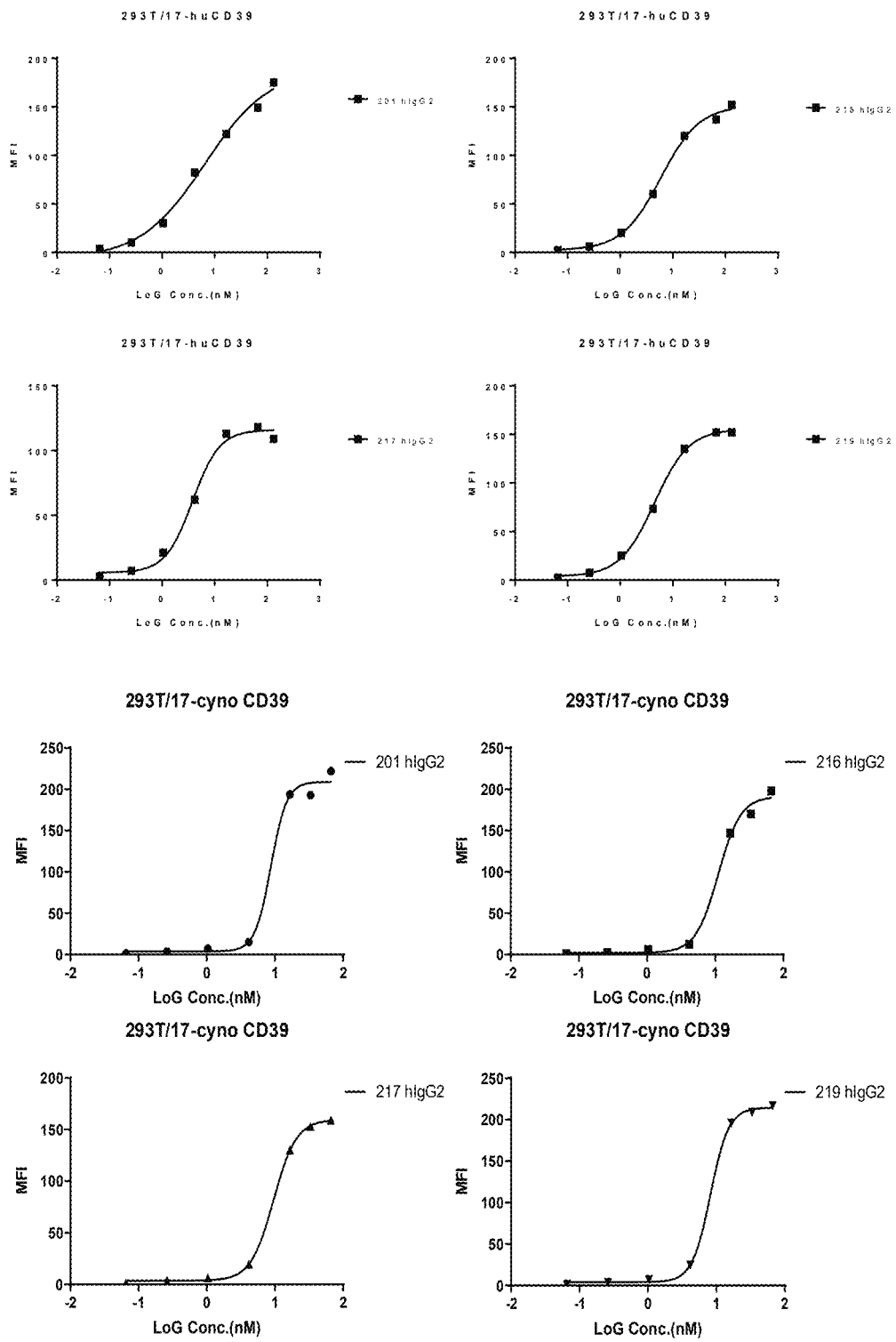
FIG. 2 shows the binding ability assay of chimeric CD39 antibody and natural CD39 protein.

Example 3: The Binding of Chimeric Antibodies to Natural CD39 on the Cell Surface Detected by Flow Cytometry Flow cytometry assay: recombinant host cell line 293T/17-huCD39 cells expressing huCD39 and recombinant host cell line 293T/17-cyno CD39 cells expressing cyno CD39 were used to evaluate the binding ability of the chimeric antibody to the natural CD39 protein on the cell surface. The recombinant cells were resuspended in PBS buffer, and $2 \times 10^6$ cells were added to a 96-well U-plate. The chimeric antibody in a certain gradient dilution range incubated for 1 h at 4° C. in a refrigerator or on ice, centrifuged at 1500 rpm for 3 min at 4° C., washed three times with PBS buffer, and then incubated for 30 min at 4° C. in the refrigerator or on ice with diluted Alexa Fluor 488-labeled goat anti-human polyclonal antibody (pAb): Goat anti-Human IgG (H+L) Cross-Adsorbed Secondary Antibody, Alexa Fluor 488 (thermo). Finally the cells were washed three times with PBS as described above and analyzed in MACSQuant flow cytometry. GraphPad Prism software was used to generate data plots and count affinity data (FIG. 2). The results are shown in Table 2, and the $EC_{50}$ values of each chimeric antibody of 293T/17-huCD39 and 293T/17-cyno CD39 was at the level of $10^{-9}$M.

TABLE 2

Affinity of chimeric antibodies to huCD39 antigen on the cell surface

| Antibody | 293T/17-huCD39 | | | 293T/17-cyno CD39 | | |
|---|---|---|---|---|---|---|
| | Bottom | Top | $EC_{50}$(nM) | Bottom | Top | $EC_{50}$(nM) |
| 201 hIgG2 | −6.241 | 189.0 | 6.560 | 3.232 | 209.1 | 8.685 |
| 216 hIgG2 | 2.171 | 151.3 | 5.915 | 1.813 | 191.4 | 11.030 |
| 217 hIgG2 | 5.802 | 116.0 | 3.799 | 2.998 | 159.6 | 9.490 |
| 219 hIgG2 | 3.810 | 155.5 | 4.511 | 3.332 | 214.5 | 8.159 |

Figure 3:
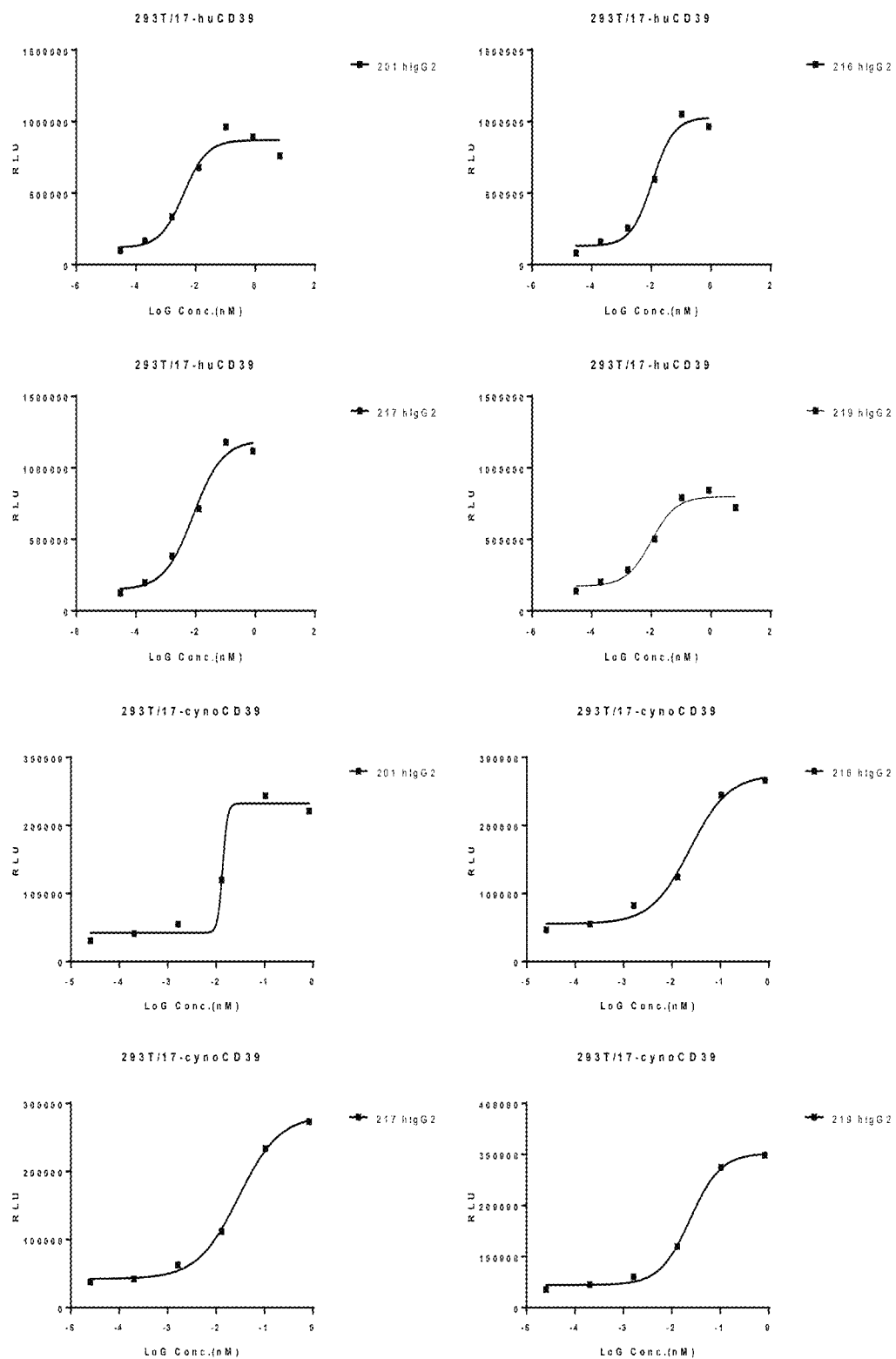
FIG. 3 shows the blocking ability of chimeric CD39 antibody against ATPase activity on cell surface.

Example 4: Blocking of ATPase Activity on Cell Surface by Chimeric CD39 Antibodies The method is based on 293T/17-huCD39 and 293T/17-cyno CD39 cell lines (pLVX-EF1α-IRES-Puro vector linked with the huCD39 or cyno CD39 gene was transfected with 293T/17 cells, and cell clones stably expressing huCD39 or cyno CD39 were obtained by puromycin screening) to detect the blocking ability of enzyme activity on cell surface by CD39 antibody, and the biochemical activity of the chimeric antibody was confirmed. 293T/17-huCD39 and 293T/17-cyno CD39 cells were digested with trypsin and the cell density was adjusted to $1.6 \times 10^5$ cells/mL, and 50 µL/well was added to the 96-well plate. 50 µL/well of a certain gradient range of antibody was added to the cell wells respectively, and incubated at 37° C. for 1 h. 100 µL of ATP at a concentration of 50 µM was added to each well and incubated at 37° C. for 0.5 h. The mixture was centrifuged at 1500 rpm for 3 min, and a certain volume of culture supernatant was transferred to a transparent 96-well flat-bottom plate (Costar, 3912). Finally, the corresponding volume of CellTiter Glo reagent was added at a ratio of 1:1 according to the Promega instructions, and after equilibration for 5 min at room temperature, luminescence values were read on a Perkin-Elmer Envision microplate reader to determine cellular CD39 enzyme activity by measuring ATP levels. Data plots were generated and enzyme kinetic data were tallied using GraphPad Prism software (FIG. 3). The results are shown in Table 3. All antibodies could inhibit the ATPase activity of CD39 on cell surface, and $EC_{50}$ values of the blocking activity of all four chimeric antibodies were at the level of $10^{-11}$ (Table 3).

Example 5: Humanization of Antibodies

The CDR transplantation method was applied to humanize the two mouse-derived antibodies obtained in Example 1. On the basis of analysis of the sequence identity and structural similarity between the two mouse-derived antibodies and the human-derived antibodies, the CDRs of the mouse-derived antibodies were modified and transplanted to a series of human-derived antibody framework regions respectively. Three humanized antibodies were obtained through screening, and three humanized antibodies were named as h201H3.1+h219L1.1 G2C, h201H3.1+h201L1.1dmut G2C, M201 HuH1L1(D-E) G2C. The sequence descriptions of the three humanized antibodies are detailed in Table 1-2. The humanized antibodies were constructed into pcDNA3.1 vector, and transfected with 293F cells to express the antibody proteins, and the antibodies were purified by ProteinA affinity chromatography.

TABLE I-2

| No. | | Variable region amino acid sequence | Variable region nucleotide sequence | Amino acid sequence | Nucleotide sequence |
|---|---|---|---|---|---|
| h201H3.1 + h219 L1.1 G2C | Heavy chain | SEQ ID NO: 60 | SEQ ID NO: 61 | SEQ ID NO: 64 | SEQ ID NO: 65 |
| | Light chain | SEQ ID NO: 62 | SEQ ID NO: 63 | SEQ ID NO: 66 | SEQ ID NO: 67 |
| h201H3.1 + h201 L1.1d mut G2C | Heavy chain | SEQ ID NO: 60 | SEQ ID NO: 61 | SEQ ID NO: 64 | SEQ ID NO: 65 |
| | Light chain | SEQ ID NO: 68 | SEQ ID NO: 69 | SEQ ID NO: 70 | SEQ ID NO: 71 |
| M201 HuH1L1 (D-E) G2C | Heavy chain | SEQ ID NO: 72 | SEQ ID NO: 73 | SEQ ID NO: 76 | SEQ ID NO: 77 |
| | Light chain | SEQ ID NO: 74 | SEQ ID NO: 75 | SEQ ID NO: 78 | SEQ ID NO: 79 |

Example 6: The Binding of Humanized Antibodies to CD39 Detected by Indirect ELISA The affinity of humanized antibodies detected by indirect ELISA: 1 µg/mL huCD39 recombinant protein was coated on ELISA plates (Coning) and incubated overnight at 4° C. The next day, washed 5 times with PBS buffer and blocked

TABLE 3

Blocking ability of chimeric CD39 antibodies against ATPase activity on cell surface

Figure 4:
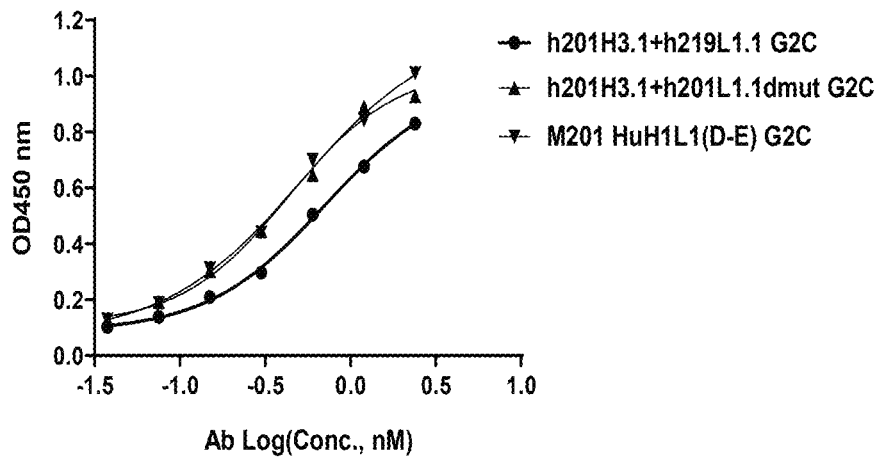
FIG. 4 shows the binding ability assay of humanized CD39 antibody and soluble huCD39 protein.

| Antibody | 293T/17-huCD39 | | | 293T/17-cyno CD39 | | |
|---|---|---|---|---|---|---|
| | Bottom | Top | $EC_{50}$(nM) | Bottom | Top | $EC_{50}$(nM) |
| 201 hIgG2 | 119247 | 870919 | 0.004 | 42339 | 232384 | 0.014 |
| 216 hIgG2 | 1280183 | 1028832 | 0.011 | 55613 | 274761 | 0.024 |
| 217 hIgG2 | 146730 | 1193309 | 0.008 | 42237 | 282537 | 0.029 |
| 219 hIgG2 | 172101 | 799649 | 0.010 | 44475 | 302601 | 0.024 | with 200 μL/well of 2% skim milk powder for 1 h. A certain dose range of CD39 humanized antibody was added, and incubated for 1 h at room temperature. Then, washed 5 times with PBST washing buffer (PBS, 0.05% Tween 20), 100 μL HRP-labeled secondary antibody was added to each well, and incubated for 30 min at room temperature. The plates were washed 5 times again, and TMB (Life Technologies) was added for color development for 5 to 10 min. Finally, 1N HCl was added to terminate the reaction, and the OD value was measured at 450 nm. GraphPad Prism software was used to generate data plots and count the affinity data (FIG. 4). The results are shown in Table 4. The $EC_{50}$ values of the binding activity of the three humanized antibodies were all at the level of $10^{-10}$ M.

TABLE 4

Affinity of humanized antibodies

| Antibody | Bottom | Top | $EC_{50}$(nM) |
|---|---|---|---|
| h201H3.1 + h219L1.1 G2C | 0.085 | 0.991 | 0.709 |
| h201H3.1 + h201L1.1d mut G2C | 0.109 | 1.030 | 0.433 |
| M201 HuH1L1(D-E) G2C | 0.068 | 1.180 | 0.514 |

Figure 5:
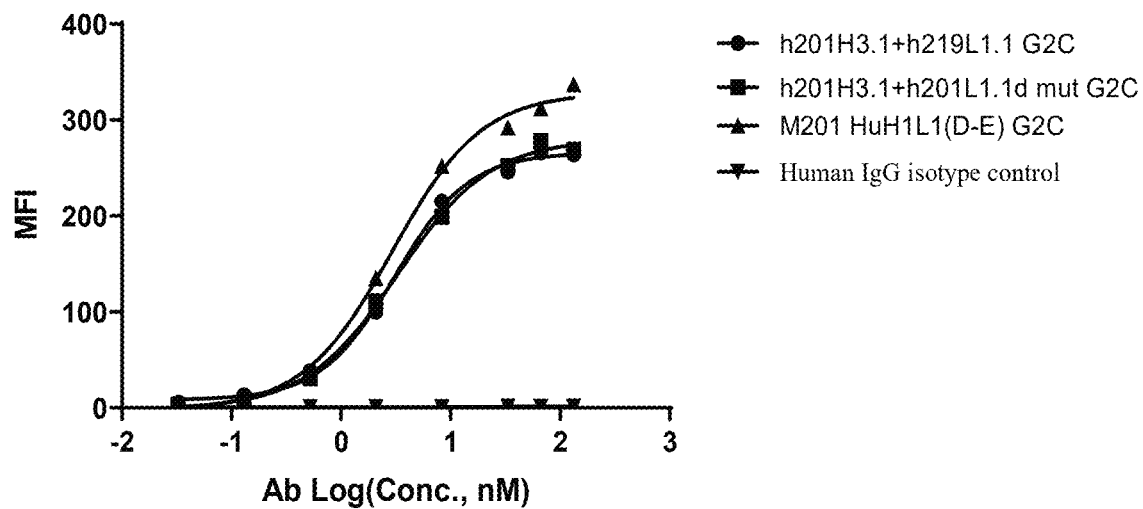
FIG. 5 shows the binding ability assay of humanized CD39 antibody and huCD39 protein on the cell surface.

Example 7: The Binding of Humanized Antibodies to Natural CD39 on the Cell Surface Detected by Flow Cytometry Flow cytometry assay: recombinant host cell line 293T/17-huCD39 cells expressing huCD39 were used to evaluate the binding ability of the humanized antibody to the natural CD39 protein on the cell surface. The recombinant cells were resuspended in PBS buffer, $2\times10^6$ cells were added to a 96-well U-plate, and a certain gradient dilution range of the humanized antibody was incubated for 1 h at 4° C. in a refrigerator or on ice. The mixture was centrifuged at 1500 rpm for 3 min at 4° C., and washed three times with PBS buffer. Then, incubated for 30 min at 4° C. in the refrigerator or on ice with diluted Alexa Fluor 488-labeled goat anti-human polyclonal antibody (pAb): Goat anti-Human IgG (H+L) Cross-Adsorbed Secondary Antibody, Alexa Fluor 488 (thermo), and finally the cells were washed three times with PBS as described above and analyzed in MACSQuant flow cytometry. Data plots were generated and affinity data were counted using GraphPad Prism software (FIG. 5). The results are shown in Table 5, and the $EC_{50}$ values of 293T/17-huCD39 humanized antibody were all at the level of $10^{-9}$M.

TABLE 5

Affinity of humanized antibodies to huCD39 antigen on the cell surface

| | 293T/17-huCD39 | | |
|---|---|---|---|
| Antibody | Bottom | Top | $EC_{50}$(nM) |
| h201H3.1 + h219L1.1 G2C | 8.182 | 266.0 | 3.097 |
| h201H3.1 + h201L1.1d mut G2C | −1.331 | 280.2 | 3.311 |
| M201 HuH1L1(D-E) G2C | −2.155 | 328.7 | 2.939 |

Figure 6:
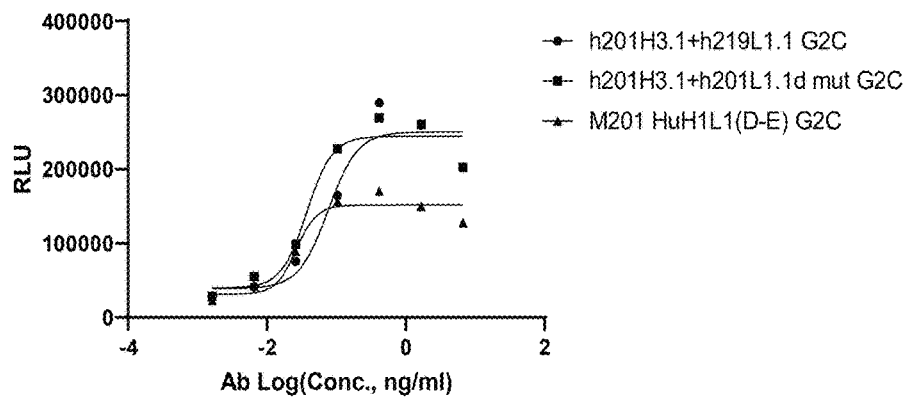
FIG. 6 shows the blocking ability of humanized CD39 antibody against ATPase activity on cell surface.

Example 8: Blocking of ATPase Activity on Cell Surface by Humanized CD39 Antibody The method was based on the 293T/17-huCD39 cell line to detect the ability of CD39 antibody to block cell surface enzyme activity and to confirm the biochemical activity of the humanized antibody. 293T/17-huCD39 cells were digested with trypsin and the cell density was adjusted to $1.6\times10^5$ cells/ml, and 50 μL/well was added to a 96-well plate. 50 μl of antibody in a gradient range of was added to the cell wells, and incubated for 1 h at 37° C. 100 μL of ATP at a concentration of 50 μM was added to each well and incubated for 0.5 h at 37° C., centrifuged at 1500 rpm for 3 min and a volume of culture supernatant was transferred to an opaque 96-well flat-bottom plate (Costar, 3912). Finally, the corresponding volume of CellTiter Glo reagent was added at a ratio of 1:1 according to Promega instructions. After equilibration for 5 min at room temperature, luminescence values were read on a Perkin-Elmer Envision microplate reader and cellular CD39 enzyme activity was determined by measuring ATP levels. Data plots were generated and enzyme kinetic data were tallied using GraphPad Prism software (FIG. 6). The results are shown in Table 6, all antibodies could inhibit the ATPase activity of cell surface CD39, and the $EC_{50}$ values of blocking activity of all three humanized antibodies were in the level of $10^{-11}$ (Table 6).

TABLE 6

Blocking ability of humanized CD39 antibody against ATPase activity on cell surface

| | 293T/17-huCD39 | | |
|---|---|---|---|
| Antibody | Bottom | Top | $EC_{50}$(nM) |
| h201H3.1 + h219L1.1 G2C | 38846 | 250500 | 0.077 |
| h201H3.1 + h201L1.1d mut G2C | 39640 | 244514 | 0.038 |
| M201 HuH1L1(D-E) G2C | 31278 | 151674 | 0.026 |

Figure 7:
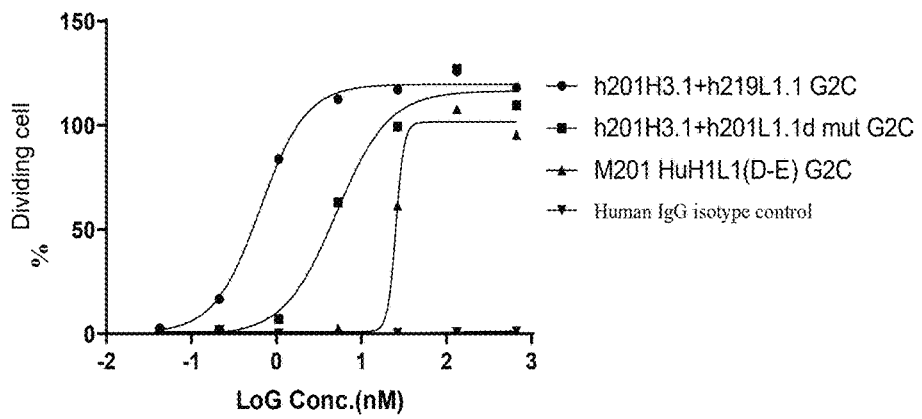
FIG. 7 shows the reversal effect of humanized CD39 antibody against ATP-mediated proliferation inhibition of human CD4+ T cell.
Figure 8:
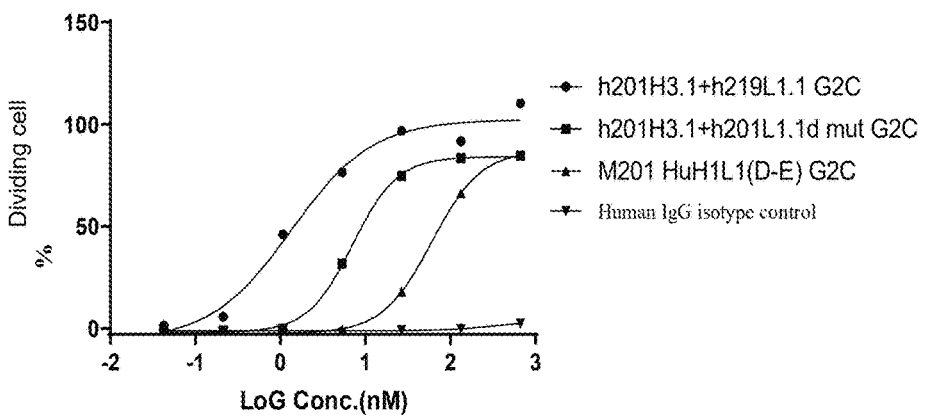
FIG. 8 shows the reversal effect of humanized CD39 antibody against ATP-mediated proliferation inhibition of human CD8+ T cell.
Figure 9:
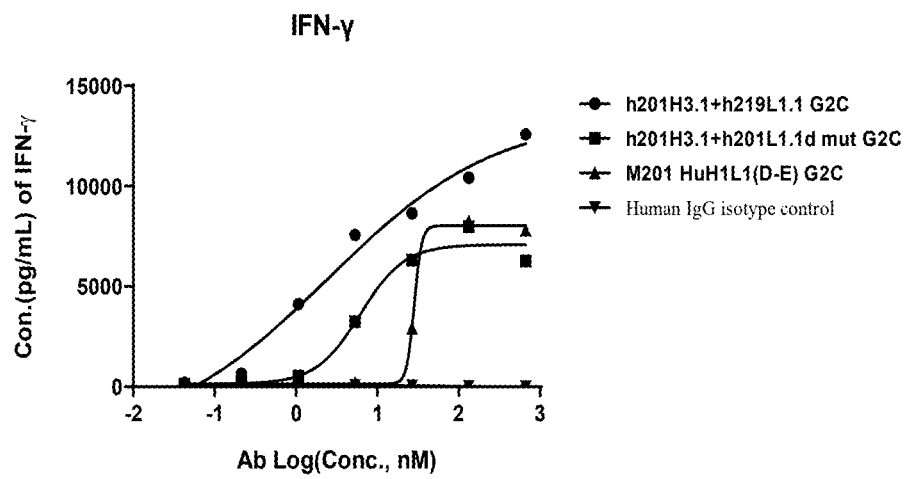
FIG. 9 shows the ability of humanized CD39 antibody to reverse the release of IFN-γ from CD4+ T cell.

Example 9: Reversal Effect of CD39 Humanized Antibody Against ATP-Mediated Proliferation Inhibition of Human CD4+T and CD8+ T Cell The method is based on the in vitro released ATP-mediated proliferation inhibition of CD4+T and CD8+ T cells by CD39 humanized antibody and IFN-γ levels in cell culture supernatants were detected by ELISA. PBMCs from human peripheral blood were recovered, and after labeled with 5 μM CFSE, adjusted the cell concentration to $1*10^6$/mL. Anti-CD28 at a final concentration of 0.5 μg/mL and human IL-2 at a final concentration of 5 ng/mL were added at 100 μL/well to a 96-well plate previously coated with 2 ug/mL anti-CD3. Gradient diluted CD39 antibody was added and incubated at 37° C. for 1 h; then ATP at a final concentration of 20-100 μM was added. After 6-7 days of incubation at 37° C., CD4+T and CD8+ T cells were collected for proliferation detection by flow cytometry (Miltenyi, Miltenyi). The supernatant was also collected to detect IFN-γ level by ELISA. CD4+T and CD8+ T cell proliferation (FIG. 7 and FIG. 8) and IFN-γ level data (FIG. 9) were counted using GraphPad Prism software. The results are shown in Table 7 that the CD39 humanized antibody viability was at the level of $10^{-8}$ to $10^{-10}$ M (Table 7).

TABLE 7

Reversal effect of CD39 antibody against ATP-mediated proliferation inhibition of human CD4+ T and CD8+ T cell

| Antibody | CD4+ T | | | CD8+ T | | |
|---|---|---|---|---|---|---|
| | Bottom | Top | $EC_{50}(nM)$ | Bottom | Top | $EC_{50}(nM)$ |
| h201H3.1 + h219L1.1 G2C | 0.371 | 119.7 | 0.646 | −6.060 | 102.3 | 1.349 |
| h201H3.1 + h201L1.1d mut G2C | −0.780 | 116.6 | 5.081 | −1.997 | 84.1 | 7.084 |
| M201 HuH1L1(D-E) G2C | 0.973 | 101.6 | 25.480 | −2.474 | 87.2 | 60.430 |

The levels of IFN-γ in cell supernatants were measured using an ELISA assay kit (Dakewe, Dakewe), and the results are shown in Table 8. The $EC_{50}$ values of IFN-γ secretion from T cells stimulated by three humanized antibodies were at the level of $10^{-8}$ to $10^{-9}$M.

TABLE 8

Ability of humanized CD39 antibody to reverse IFN-γ release from CD4 + T cell

| Antibody | Bottom | Top | ECso(nM) |
|---|---|---|---|
| h201H3.1 + h219L1.1 G2C | −2793 | 13557 | 2.455 |
| h201H3.1 + h201L1.1d mut G2C | 140 | 7087 | 6.157 |
| M201 HuH1L1(D-E) G2C | 146 | 8031 | 28.420 |

Example 10: Humanized CD39 Antibody-Mediated Endocytosis Assay of CD39

Figure 10:
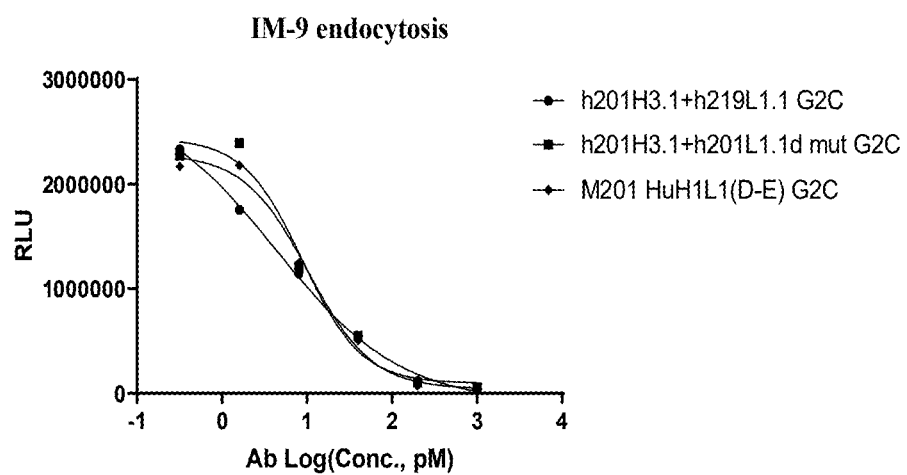
FIG. 10 shows the endocytosis of CD39 mediated by humanized CD39 antibody.

Fab-ZAP saporin reagent (Advanced Targeting Systems) was used to detect the endocytosis effect mediated by humanized CD39 antibody on IM-9 cells. The antibody was gradient diluted to a certain dose range with 40 nM Fab-ZAP human reagent (Advanced Targeting Systems) and incubated at room temperature for 30 min to make Fab-ZAP bind to the antibody to be tested to form an antibody premix. 50 μL of this antibody premix was added to IM-9 cell wells of 10,000 cells/well, incubated for 3 days at 37° C. with 5% $CO_2$, lysed by adding CTG reagent (Promega) for 2 min, and then equilibrated at room temperature for 5 min. The luminescence values were measured with an Enspire enzyme marker (Perkin Elmer). The cell growth curves were calculated by GraphPad Prism software. The results are shown in Table 9 and FIG. 10. All three humanized antibodies mediated CD39 endocytosis in a dose-dependent manner, and the $IC_{50}$ values of each antibody were at the level of $10^{-11}$~$10^{-22}$M.

TABLE 9

CD39 endocytosis effect mediated by humanized CD39 antibodies

| Antibody | Bottom | Top | $IC_{50}(pM)$ |
|---|---|---|---|
| h201H3.1 + h219L1.1 G2C | −97751 | 2846167 | 4.299 |
| h201H3.1 + h201L1.1d mut G2C | 96175 | 2439511 | 8.901 |
| M201 HuH1L1 (D-E) G2C | 40891 | 2289436 | 10.300 |

Example 11: Activation Effect of Humanized CD39 Antibody Against DC Cells

Figure 11:
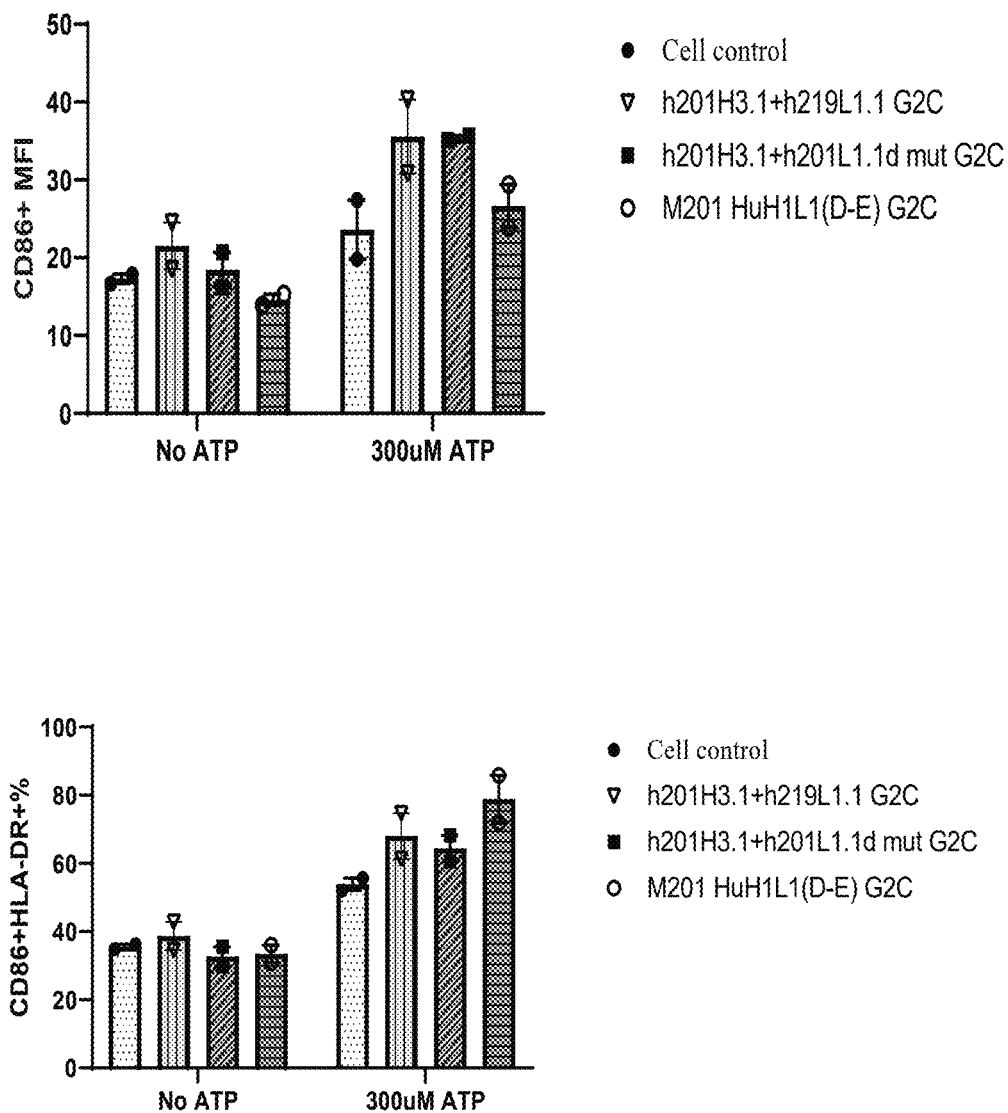
FIG. 11 shows the activation effect of humanized CD39 antibody against DC cell.

This method was used to determine the activation effect of CD39 humanized antibody against DC cells mainly through detecting the expression levels of cell surface molecules CD86 and HLA-DR in DCs by flow cytometry. Monocytes were recovered and resuspended, and cell density was adjusted to $5*10^5$/mL. The cells were cultured in the plates, and stimulated with 1640+10% FBS medium containing M-CSF (50 ng/mL) and IL-4 (long/mL) at 37° C. for 6 days to obtain DC cells. After 6 days, cell supernatant was discarded and 1 μg/mL of humanized CD39 antibody was added, and the cells were incubated at 37° C. for 1 h, and then incubated overnight with or without a certain concentration of ATP. After 24 h, the cells were collected for FACS to detect the expression of CD86 and HLA-DR, and the statistical data was generated by GraphPad Prism software. The results are shown in FIG. 11 that humanized CD39 antibodies enhanced ATP-induced single expression of the cell surface molecule CD86 and co-expression of CD86 and HLA-DR in DCs cells.

Example 12: Pharmacodynamics Evaluation of Humanized CD39 Antibody on MOLP-8 Model MOLP-8 (human multiple myeloma cells) was diluted with PBS stromal gum at a ratio of 1:1. 6-8 week old female CB-17 SCID mice (purchased from Beijing Viton Lever Laboratory Animal Technology Co., Ltd.) were subcutaneously inoculated with $1\times10^7$ cells, and each of groups has 26 mice. After subcutaneous inoculation, the mice were grouped when the tumor growth volume reached 300 $mm^3$ (the largest and smallest animals were excluded from each group) and injected intraperitoneally (I.P.) with PBS, antibody h201H3.1+h201L1.1d mut G2C and M201 HuH1L1 (D-E) G2C at a dose of 30 mg/kg once/week (QW), as shown in Table 10.

TABLE 10

Route of administration, dose and regimen

| No. | Number | Route of administration | Treatment | Dosing amount | Dosing frequency | Dosing cycle |
|---|---|---|---|---|---|---|
| G1 | 26 | I.P. | PBS | N/A | QW | 1 week |
| G2 | 26 | I.P. | h201H3.1 + h201L1.1d mut G2C | 30 mg/kg | QW | 1 week |
| G3 | 26 | I.P. | M201 HuH1L1(D-E) GC | 30 mg/kg | QW | 1 week |

Figure 12:
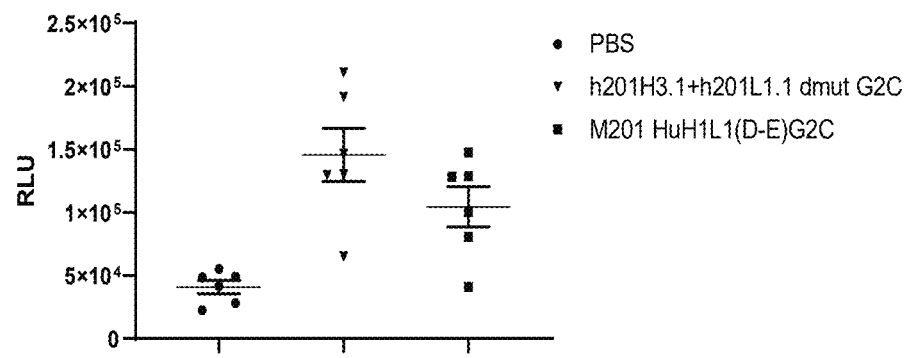
FIG. 12 shows the pharmacodynamics evaluation of humanized CD39 antibody on MOLP-8 xenograft model.
Figure 12:
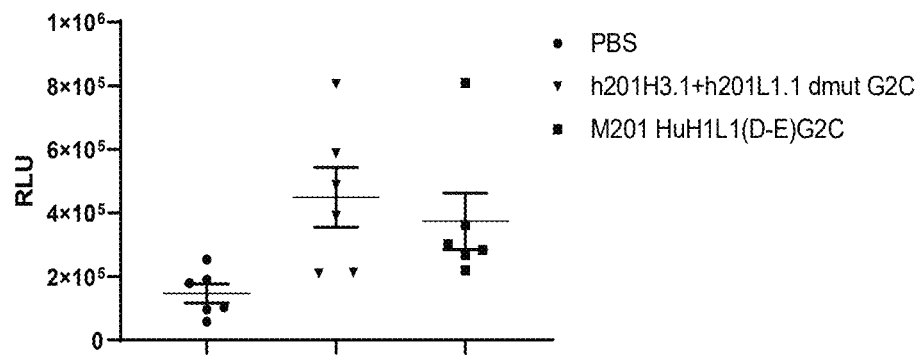
Figure 12:
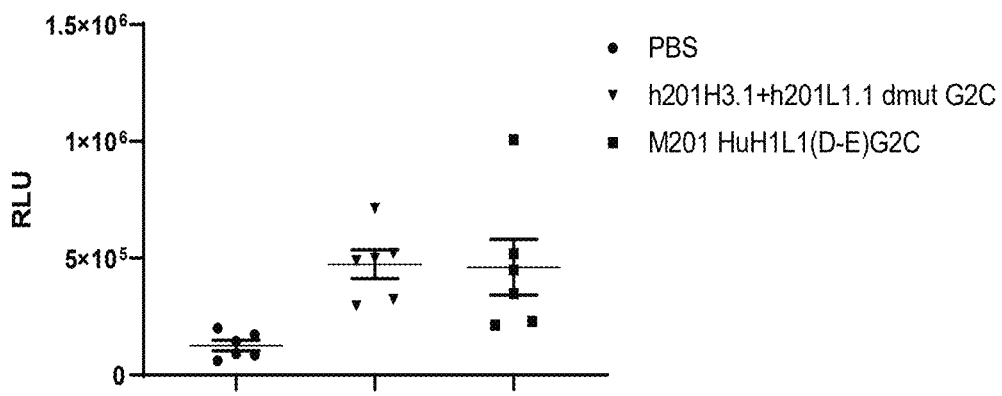

On the first, third, and seventh day after drug administration, tumor tissues from 6 mice were taken to prepare into single cell suspensions for enzyme activity assay. The tumor tissues were cut into small pieces and digested with enzymes. After incubation at 37° C. for 40 min, the undigested tissue pieces were removed by filtration with a 70 μm filter and the single cell suspension was collected. $5*10^4$ cells were spread in a 96-well plate, and a final concentration of 25 μM ATP solution was added, incubated at 37° C. for 30 min, and a certain volume of culture supernatant was transferred to a tranparent 96-well flat-bottom plate (Costar, 3912). Finally, the appropriate volume of CellTiter Glo reagent at a ratio of 1:1 was added according to the Promega instructions. After equilibration for 5 min at room temperature, the luminescence values were read on a Perkin-Elmer Envision enzyme marker to determine the enzymatic activity of CD39 humanized antibody on MOLP-8 tumor cells by measuring ATP levels. The results were shown in FIG. 12 that both humanized antibodies had enzymatic activity blocking effects on MOLP-8 tumor cells at first, third and seventh day after administration.

Example 13: Growth Inhibition of MOLP-8 Xenograft Tumor Model by Humanized Antibody MOLP-8 (human multiple myeloma cells) were diluted with PBS stromal gum at a ratio of 1:1 to obtain the cells of $1×10^8$. 6-8 week old female CB-17 SCID mice (purchased from Beijing Viton Lever Laboratory Animal Technology Co., Ltd.) were subcutaneously inoculated with 0.1 mL for each. The mice were randomly grouped in each group of 12, i.e. 6 males and 6 females in each group. Each group was administered with 30 mg/kg dose of intraperitoneal (I.P.) PBS, antibodies h201H3.1+h201L1.1d mut G2C and M201 HuH1L1(D-E) G2C, twice/week (BIW) at seventh day after subcutaneous inoculation, and the detailed description was shown in Table 11.

TABLE 11

Route of administration, dose and regimen

| | | | | Dosage | |
|---|---|---|---|---|---|
| No. | Number | Treatment | Dosing frequency | Dosing amount (mg/kg) | Route of administration |
| 1 | 12 (6 female 6 male) | PBS | BIW | N/A | I.P. |
| 2 | 12 (6 female 6 male) | h201H3.1 + h201L1.1d mut G2C | BIW | 30 | I.P. |
| 3 | 12 (6 female 6 male) | M201 HuH1L1(D-E) G2C | BIW | 30 | I.P. |

The body weight and tumor size of the mice were measured twice a week. Tumor size calculation formula: tumor volume $(mm^3)=0.5×$(tumor long diameter×tumor short diameter$^2$).

Figure 13:
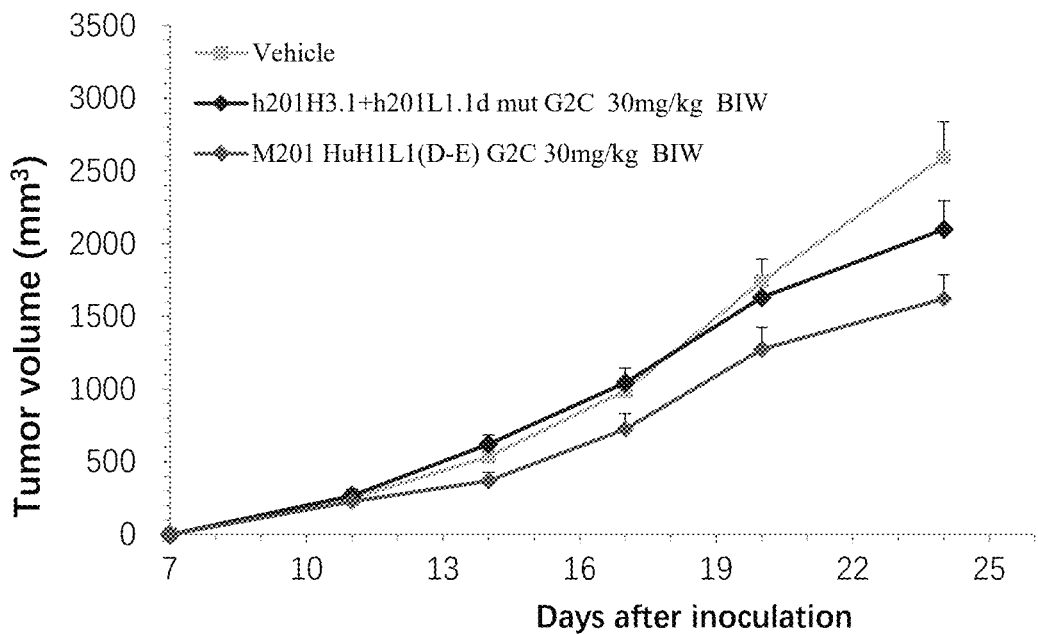
FIG. 13 shows the tumor growth inhibition effect of humanized CD39 antibody against MOLP-8 in MOLP-8 xenograft model.

The tumor growth curve was plotted according to the tumor volume. As seen in FIG. 13, both antibodies h201H3.1+h201L1.1d mut G2C and M201 HuH1L1(D-E) G2C inhibited MOLP-8 tumor growth.

Example 14: Growth Inhibition of IM-9 Xenograft Tumor Model by Humanized Antibodies IM-9 (human peripheral blood B lymphocytes) were diluted with PBS stromal gum at a ratio of 1:1 to obtain the cells of $1×10^8$ cells/ml. 6-8 week old female CB-17 SCID mice (purchased from Beijing Viton Lever Laboratory Animal Technology Co., Ltd.) were subcutaneously inoculated with 0.1 mL for each. The mice were grouped in each group of 12, females. After subcutaneous inoculation, each group were injected intraperitoneally (I.P.) with PBS, antibodies h201H3.1+h201L1.1d mut G2C and M201 HuH1L1(D-E) G2C at a dose of 30 mg/kg, twice/week (BIW), when the tumor growth volume reached 50-70 $mm^3$ groups (inclusion criteria: mean tumor volume±3SD range, or tumor volume coefficient of variation CV≤30% (CV=standard deviation/mean)). The detailed description was shown in Table 12.

TABLE 12

Route of administration, dose and regimen

| | | | | Dosage | |
|---|---|---|---|---|---|
| No. | Number | Treatment | Dosing frequency | Dosing amount (mg/kg) | Route of administration |
| 1 | 10 (female) | PBS | BIW | N/A | I.P. |
| 2 | 10 (female) | h201H3.1 + h201L1.1d mut G2C | BIW | 30 | I.P. |
| 3 | 10 (female) | M201 HuH1L1(D-E) G2C | BIW | 30 | I.P. |

The body weight and tumor size of the mice were measured twice a week. Tumor size calculation formula: tumor volume $(mm^3)=0.5×$(tumor long diameter×tumor short diameter$^2$)

Figure 14:
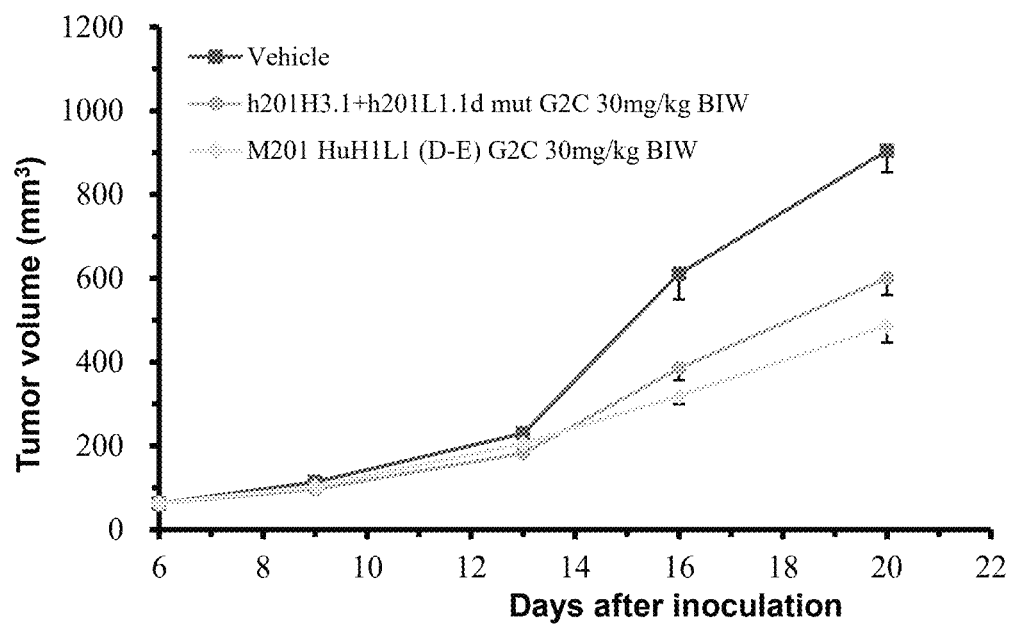
FIG. 14 shows the tumor growth inhibition effect of humanized CD39 antibody against IM-9 in IM-9 xenograft tumor model.

The tumor growth curve was plotted according to the tumor volume. As seen in FIG. 14, both antibodies h201H3.1+h201L1.1d mut G2C and M201 HuH1L1(D-E) G2C were effective in inhibiting IM-9 tumor growth.

What is claimed is:

1. An antibody or antigen-binding fragment thereof comprising a heavy chain variable region that comprises sequences of HCDR1, HCDR2, HCDR3; and a light chain variable region that comprises sequences of LCDR1, LCDR2, LCDR3, wherein:
   (a) the HCDR1 comprises an amino acid sequence of SEQ ID NO: 5;
   (b) the HCDR2 comprises an amino acid sequence of SEQ ID NO: 6;
   (c) the HCDR3 comprises an amino acid sequence of SEQ ID NO: 7;
   (d) the LCDR1 comprises an amino acid sequence of SEQ ID NO: 10;
   (e) the LCDR2 comprises an amino acid sequence of SEQ ID NO: 59 or 11; and
   (f) the LCDR3 comprises an amino acid sequence of SEQ ID NO: 12.

2. The antibody or antigen-binding fragment thereof of claim 1, wherein:
   (i) the heavy chain variable region (VH) comprises an amino acid sequence with at least 85% identity to an amino acid sequence selected from a group consisting of SEQ ID NOs: 3, 60 and 72, and comprises HCDR1 comprising SEQ ID NO: 5, HCDR2 comprising SEQ ID NO: 6, and HCDR3 comprising SEQ ID NO: 7; and
   (ii) the light chain variable region (VL) comprises an amino acid sequence with at least 85% identity to an amino acid sequence selected from a group consisting of SEQ ID NOs: 8, 68 and 74, and comprises LCDR1 comprising SEQ ID NO: 10, LCDR2 comprising SEQ ID NO: 59 or 11, and LCDR3 comprising SEQ ID NO: 12.

3. The antibody or antigen-binding fragment thereof of claim 1, comprising:
   1) a heavy chain variable region (VH) that comprises an amino acid sequence with at least 85% identity to an amino acid sequence of SEQ ID NO: 60 and comprises HCDR1 comprising SEQ ID NO: 5, HCDR2 comprising SEQ ID NO: 6, and HCDR3 comprising SEQ ID NO: 7, and a light chain variable region (VL) that comprises an amino acid sequence with at least 85% identity to an amino acid sequence of SEQ ID NO: 68 and comprises LCDR1 comprising SEQ ID NO: 10, LCDR2 comprising SEQ ID NO: 59, and LCDR3 comprising SEQ ID NO: 12; or
   2) a heavy chain variable region (VH) that comprises an amino acid sequence with at least 85% identity to an amino acid sequence of SEQ ID NO: 72 and comprises HCDR1 comprising SEQ ID NO: 5, HCDR2 comprising SEQ ID NO: 6, and HCDR3 comprising SEQ ID NO: 7, and a light chain variable region (VL) that comprises an amino acid sequence with at least 85% identity to an amino acid sequence of SEQ ID NO: 74 and comprises LCDR1 comprising SEQ ID NO: 10, LCDR2 comprising SEQ ID NO: 59, and LCDR3 comprising SEQ ID NO: 12; or 3) a heavy chain variable region (VH) that comprises an amino acid sequence with at least 85% identity to an amino acid sequence of SEQ ID NO: 3 and comprises HCDR1 comprising SEQ ID NO: 5, HCDR2 comprising SEQ ID NO: 6, and HCDR3 comprising SEQ ID NO: 7, and a light chain variable region (VL) that comprises an amino acid sequence with at least 85% identity to an amino acid sequence of SEQ ID NO: 8 and comprises LCDR1 comprising SEQ ID NO: 10, LCDR2 comprising SEQ ID NO: 11, and LCDR3 comprising SEQ ID NO: 12.

4. The antibody or antigen-binding fragment thereof of claim 1, comprising:
   1) a heavy chain variable region (VH) comprising an amino acid sequence of SEQ ID NO: 60, and a light chain variable region (VL) comprising an amino acid sequence of SEQ ID NO: 68; or
   2) a heavy chain variable region (VH) comprising an amino acid sequence of SEQ ID NO: 72, and a light chain variable region (VL) comprising an amino acid sequence of SEQ ID NO: 74; or
   3) a heavy chain variable region (VH) comprising an amino acid sequence of SEQ ID NO: 3, and a light chain variable region (VL) comprising an amino acid sequence of SEQ ID NO: 8.

5. The antibody or antigen-binding fragment thereof of claim 1, further comprising a heavy chain constant region that is an IgG.

6. The antibody or antigen-binding fragment thereof of claim 5, wherein the heavy chain constant region of the antibody is selected from IgG1, IgG2 or IgG4.

7. The antibody or antigen-binding fragment thereof of claim 1, wherein the antibody is a monoclonal antibody, a chimeric antibody, a humanized antibody, a human engineered antibody, a human antibody, Fv, a single chain antibody (scFv), Fab, Fab', Fab'-SH or F(ab')$_2$.

8. The antibody or antigen-binding fragment thereof of claim 1, comprising a heavy chain and a light chain, wherein:
   (I) the heavy chain comprises an amino acid sequence with at least 85% identity to an amino acid sequence selected from a group of SEQ ID NOs: 13, 64 and 76, and comprises HCDR1 comprising SEQ ID NO: 5, HCDR2 comprising SEQ ID NO: 6, and HCDR3 comprising SEQ ID NO: 7; and
   (II) the light chain comprises an amino acid sequence with at least 85% identity to an amino acid sequence selected from a group of SEQ ID NOs: 15, 70 and 78, and comprises LCDR1 comprising SEQ ID NO: 10, LCDR2 comprising SEQ ID NO: 59 or 11, and LCDR3 comprising SEQ ID NO: 12.

9. The antibody or antigen-binding fragment thereof of claim 1, comprising:
   1) a heavy chain that comprises an amino acid sequence with at least 85% identity to an amino acid sequence of SEQ ID NO: 64 and comprises HCDR1 comprising SEQ ID NO: 5, HCDR2 comprising SEQ ID NO: 6, and HCDR3 comprising SEQ ID NO: 7, and a light chain that comprises an amino acid sequence with at least 85% identity to an amino acid sequence of SEQ ID NO: 70 and comprises LCDR1 comprising SEQ ID NO: 10, LCDR2 comprising SEQ ID NO: 59, and LCDR3 comprising SEQ ID NO: 12; or
   2) a heavy chain that comprises an amino acid sequence with at least 85% identity to an amino acid sequence of SEQ ID NO: 76 and comprises HCDR1 comprising SEQ ID NO: 5, HCDR2 comprising SEQ ID NO: 6, and HCDR3 comprising SEQ ID NO: 7, and a light chain that comprises an amino acid sequence with at least 85% identity to an amino acid sequence of SEQ ID NO: 78 and comprises LCDR1 comprising SEQ ID NO: 10, LCDR2 comprising SEQ ID NO: 59, and LCDR3 comprising SEQ ID NO: 12; or
   3) a heavy chain that comprises an amino acid sequence with at least 85% identity to an amino acid sequence of SEQ ID NO: 13 and comprises HCDR1 comprising SEQ ID NO: 5, HCDR2 comprising SEQ ID NO: 6, and HCDR3 comprising SEQ ID NO: 7, and a light chain that comprises an amino acid sequence with at least 85% identity to an amino acid sequence of SEQ ID NO: 15 and comprises LCDR1 comprising SEQ ID NO: 10, LCDR2 comprising SEQ ID NO: 11, and LCDR3 comprising SEQ ID NO: 12.

10. The antibody or antigen-binding fragment thereof of claim 1, comprising:
    1) a heavy chain that comprises an amino acid sequence of SEQ ID NO: 64, and a light chain that comprises an amino acid sequence of SEQ ID NO: 70; or
    2) a heavy chain that comprises an amino acid sequence of SEQ ID NO: 76, and a light chain that comprises an amino acid sequence of SEQ ID NO: 78; or
    3) a heavy chain that comprises an amino acid sequence of SEQ ID NO: 13, and a light chain that comprises an amino acid sequence of SEQ ID NO: 15.

11. The antibody or antigen-binding fragment thereof of claim 1, which is an antagonist of CD39.

12. The antibody or antigen-binding fragment thereof of claim 11, wherein the CD39 is human CD39 or machin CD39.

13. The antibody or antigen-binding fragment thereof of claim 1, which may reduce the ATP enzyme (ATPase) activity of CD39.

14. A pharmaceutical composition comprising the antibody or antigen-binding fragment thereof of claim 1, and a pharmaceutically acceptable carrier.

15. A kit comprising the antibody or antigen-binding fragment thereof of claim 1.

16. A method of treating a disease comprising administering to a subject in need a therapeutically effective amount of the antibody or antigen-binding fragment thereof of claim 1.

17. The method of claim 16, wherein the disease is a disease related to CD39.

18. The method of claim 16, wherein the disease is cancer.

19. The method of claim 18, wherein the cancer is solid tumor or hematological cancer.

20. The method of claim 19, wherein the solid tumor is selected from multiple myeloma, melanoma, stomach cancer, pancreatic cancer, breast cancer, colon cancer, lung cancer, head and neck cancer, liver cancer, ovarian cancer, bladder cancer, renal cancer, salivary gland carcinoma, esophageal cancer, glioma, glioblastoma, thyroid cancer, thymic cancer, epithelial cancer, lymphoma, T and/or B cell lymphoma, gastrointestinal stromal tumor, soft tissue neoplasm, testicular cancer, endometrial carcinoma, prostate cancer, and/or brain cancer.

* * * * *